US007955596B2

(12) United States Patent
Jones et al.

(10) Patent No.: US 7,955,596 B2
(45) Date of Patent: Jun. 7, 2011

(54) B. ANTHRACIS PREVENTION AND TREATMENT: MUTANT B. ANTHRACIS LACKING LUXS ACTIVITY AND FURANONE INHIBITION OF GROWTH, AI-2 QUORUM SENSING, AND TOXIN PRODUCTION

(75) Inventors: Marcus B. Jones, Rockville, MD (US); Martin J. Blaser, New York, NY (US); Thomas Wood, Tolland, CT (US); Dacheng Ren, Ithaca, NY (US)

(73) Assignees: New York University, New York, NY (US); University of Connecticut, Farmington, CT (US)

( * ) Notice: Subject to any disclaimer, the term of this patent is extended or adjusted under 35 U.S.C. 154(b) by 384 days.

(21) Appl. No.: 12/044,135

(22) Filed: Mar. 7, 2008

(65) Prior Publication Data

US 2008/0299153 A1    Dec. 4, 2008

Related U.S. Application Data

(62) Division of application No. 10/823,396, filed on Apr. 12, 2004, now Pat. No. 7,365,184.

(60) Provisional application No. 60/462,254, filed on Apr. 11, 2003, provisional application No. 60/462,255, filed on Apr. 11, 2003.

(51) Int. Cl.
*A01N 63/00* (2006.01)
*A61K 39/00* (2006.01)
*A61K 39/02* (2006.01)
*C12N 1/12* (2006.01)
*C12N 15/74* (2006.01)
*C12N 15/75* (2006.01)

(52) U.S. Cl. ............... 424/93.46; 424/93.2; 424/184.1; 424/200.1; 424/234.1; 435/485; 435/483; 435/252.31

(58) Field of Classification Search ........................ None
See application file for complete search history.

(56) References Cited

OTHER PUBLICATIONS

Bourgogne, A.D., et al., *Bacillus anthracis* harbors a functional orthologue of luxS, a gene essential for antoinducer-2 activity. Abstr. 101st General Meeting of the American Society for Microbiology, Orlando, FL., USA, May 20-24, 2001, p. 127.
Jones, M.B., et al., "luxS-mediated quorum-sensing in *Bacillus anthracis*" Abstr. 103rd General Meeting of the American Society for Microbiology, Washington, D.C., USA, May 18-22, 2003, p. I-024.
Jones, M.B., et al., "Detection of a luxS-signaling molecule in *Bacillus anthracis*" Infect. Immun. Jul. 2003, vol. 71, No. 7, pp. 3914-3919, see Materials and Methods and Results.
Adjei, et al. Pharmaceutical Research 1990; 7:565-569 and 63:135-144 (leuprolide acetate), "Pulmonary delivery of peptide drugs: effect of particle size on bioavailability of leuprolide acetate in healthy male volunteers."###.
Bassler, Wright and Silverman. Mol. Microbiol. 1994; 13:273-286, "Multiple signaling systems controlling expression of luminescence in Vibrio harveyi: sequence and function of genes encoding a second sensory pathway."
Benoist & Chambon, Nature 1981; 290:304-310I, "Sequence requirements of the SV40 early promotor region."
Braquet, et al. J. Cardiovascular Pharmacology 1989;13 (sup5): 143-146 (endothelin-1) "Effect of endothelin-1 on blood pressure and bronchopulmonary system of the guinea pig."
Brinster RL, et al., Nature 1982; 296:39-42, "Regulation of metallothionein—thymidine kinase fusion plasmids injected into mouse eggs."
Chang Tk et al., (1993) Cancer Res. 53:1043-1050, "Differential activation of cyclophosphamide and ifosphamide by cytochromes P-450 2B and 3A in human liver microsomes."
Chen at al., Nature 2001; 415:545-549, Chen, X., S. Schauder, N. Potler, A. Dorsselaer, I. Pelczer, B. Bassler, and F. M. Hughson. 2001. "Structural identification of a bacterial quorum-sensing signal containing boron." Nature 415:545-549.
Cote et al., Proc. Natl. Acad. Sci. USA 1983;80:2026-2030, "Generation of Human Monoclonal Antibodies Reactive with Cellular Antigens."
Debs RJ, et al. J. Immunol. 1988; 140:3482-3488 (interferon-and tumor necrosis factor ) "Lung-specific delivery of cytokines induces sustained pulmonary and systemic immunomodulation in rats."
Greenberg, Hastings and Ulitzur. Arch. Microbiol. 1979; 120:87-91, "Not found on Medline, please provide reference."
Greener, et al., Strategies in Mol. Biol. 1995 7:32, "Not found on Medline, please provide reference."
Guerot-Fleury, A., et al. Gene. 1995;167:335-336, "Antibiotic resistance cassettes for *Bacillus* reference."
Guerot-Fleury, A., et al. Gene. 1995;167:335-336, "Antibiotic resistance cassettes for *Bacillus subtilis*."
Hermes et al., Proc. Natl. Acad. Sci. USA 1990;87:696-700, "Searching Sequence Space by Definably Random Mutagenesis: Improving the Catalytic Potency of an Enzyme."
Hood et al., Immunology, Second Ed., 1984, Benjamin/Cummings: Menlo Park, California, p. 384, Book.

(Continued)

*Primary Examiner* — S. Devi
(74) *Attorney, Agent, or Firm* — Fish & Richardson P.C.

(57) ABSTRACT

The present invention pertains to the discovery that *B. anthracis* possesses a luxS gene that encodes a functional LuxS polypeptide, and that *B. anthracis* synthesizes a functional AI-2 quorum-sensing molecule. The invention provides mutant *B. anthracis* bacteria lacking the function of the luxS gene, which do not produce a functional AI-2 molecule and have growth defects compared to wild-type *B. anthracis*. The invention also concerns methods for inhibiting the growth of *B. anthracis*, or for preventing or treating *B. anthracis* infection, by inhibiting the activity of the *B. anthracis* LuxS polypeptide, or by exposure of the *B. anthracis* to furanone. In particular, the invention concerns the use of furanone, a compound that inhibits AI-2-mediated quorum-sensing, to inhibit the growth of *B. anthracis*, to inhibit *B. anthracis* toxin production, particularly that of protective antigen, and to prevent or treat *B. anthracis* infection. The invention also provides methods to prevent *B. anthracis* infection, or enhance an immune response to *B. anthracis* infection, by administering a vaccine comprising a *B. anthracis* cell in which the luxS gene is mutated.

11 Claims, 22 Drawing Sheets

OTHER PUBLICATIONS

Hubbard, et al. (1989) Annals of Internal Medicine, vol. III, pp. 206-212 (1-antitrypsin), Book chapter Note: Can be provided upon request.
Huse WD et al., Science 1989; 246:1275-1281, "Generation of a large combinatorial library of the immunoglobulin repertoire in phage lambda."
Jernigan JA, et al., Emer. Inf. Dis. 2001;7:933-933, "Bioterrorism-related inhalation anthrax: the first 10 cases reported in the United States."
Kohler G & Milstein C, Nature 1975; 256:495-497, "Continuous cultures of fused cells secreting antibody of predefined specificity."
Kozbor et al., Immunology Today 1983;4:72.
Loeffler DA et al (1992) Cytom. 13: 169-174, "Analysis of distribution of tumor-and preneoplasia-infiltrating lymphocytes using simultaneous Hoechst 33342 labeling and immunophenotyping."
Marshall, K. In: Modern Pharmaceutics Edited by G.S. Banker and C.T. Rhodes, Chapter 10, 1979 Book, Note: Can be provided upon request.
Mock, M., and A. Fouet. Annu. Rev. Microbiol 2001;55:647-671Mock, M., and A. Fouet. 2001, "Anthrax. Annu. Rev. Microbiol. 55:647-671".
Morrison et al., J. Bacteriol. 1984; 159:870, "Isolation of transformation-deficient Streptococcus pneumoniae mutants defective in control of competence, using insertion-duplication mutagenesis with the erythromycin resistance determinant of pAM beta 1."
Neuberger et al., Nature 1984;312:604-608, "Recombinant antibodies possessing novel effector functions".
Nielsen PE et al., Science 1991, 254:1497, "Sequence-selective recognition of DNA by strand displacement with thymine-substituted polyamide."
Provinciali M, et al., (1992) J. Immunol. Meth. 155:19-24, "Optimization of cytotoxic assay by target cell retention of the fluorescent dye carboxyfluorescein diacetate (CFDA) and comparison with conventional 51CR release assay."
Ren, D. et al., Environ. Microbiol. 2001;3:731-736, "Inhibition of biofilm formation and swarming of *Escherichia coli* by (5Z)-4-bromo-5-(bromomethylene)-3-butyl-2(5H)-furanone."
Ren, D. et al., Let. Appl. Microbil. 2002;34:293-299, "Inhibition of biofilm formation and swarming of *Bacillus subtilis* by (5Z)-4-bromo-5-(bromomethylene)-3-butyl-2(5H)-furanone."
Rivoltini L et al., (1992) Can. Immunol. Immunother. 34: 241-251, "Phenotypic and functional analysis of lymphocytes infiltrating paediatric tumours, with a characterization of the tumour phenotype."
Scientific American 1980;242:74-94.
Sirard, Mock and Foeut. J. Bacteriol. 1994;176:5188-92, "The three *Bacillus anthracis* toxin genes are coordinately regulated by bicarbonate and temperature."
Takeda S et al., Nature 1985;314-452-454, "Construction of chimaeric processed immunoglobulin genes containing mouse variable and human constant region sequences."
Villa-Komaroff L et al., proc. Natl. Acad. Sci. USA 1978;75:3727-3731, "A Bacterial Clone Synthesizing Proinsulin."
Vollenweider I et al., (1992) J. Immunol. Meth. 149:133-135, "Comparison of four DNA staining fluorescence dyes for measuring cell proliferation of lymphokine-activated killer (LAK) cells."
Wagner, et al., Proc. Natl. Acad. Sci. USA 1981; 78:1441-1445.
Yamamoto T, et al., Cell 1980;22:787-797, "Identification of a functional promoter in the long terminal repeat of *Rous sarcoma* virus."
Rudinger, "Characteristics of the amino acids as components of a peptide hormone sequence", Peptide Hormones, Edited by J. A. Parsons, National Institute for Medical Research, Mill Hill, London University Park Press, pp. 1-7, (1976).
Houghten et al. "New Approaches to Immunization", Vaccines86, Cold Spring Harbor Laboratory, p. 21-25, (1986).

| 1   | ATGCCATCAG | TAGAAAGCTT | TGAATTAGAT | CATACGATTG | TAAAGGCACC |
| 51  | TTATGTAAGA | CATTGCGGAG | TTCACAATGT | AGGTAGTGAC | GGTATTGTAA |
| 101 | ATAAATTCGA | TATTCGTTTT | TGCCAACCGA | ATAAACAAGC | AATGAAACCA |
| 151 | GATGTTATTC | ATACGTTAGA | ACATTTATTA | GCATTTAATT | TACGTAAATA |
| 201 | TATTGATCGT | TATCCACATT | TTGATATTAT | CGATATTTCA | CCAATGGGCT |
| 251 | GCCAAACAGG | ATACTACCTT | GTAGTAAGCG | AACACCGAC | AGTTCGAGAA |
| 301 | ATCATTGATT | TATTAGAATT | AACATTAAAA | GATGCGGTTC | AAATTACAGA |
| 351 | AATTCCAGCT | GCAAATGAAA | CACAATGTGG | TCAAGCGAAG | CTTCACGATT |
| 401 | TAGAAGGAGC | AAAACGCTTA | ATGAACTTCT | GGTTAAGCCA | AGATAAAGAT |
| 451 | GAACTTGAGA | AAGTATTTGG | ATAA |

FIGURE 1

| 1 | MPSVESFELD | HTIVKAPYVR | HCGVHNVGSD | GIVNKFDIRF | 40 |
| 41 | CQPNKQAMKP | DVIHTLEHLL | AFNLRKYIDR | YPHFDIIDIS | 80 |
| 81 | PMGCQTGYYL | VVSGTPTVRE | IIDLLELTLK | DAVQITEIPA | 120 |
| 121 | ANETQCGQAK | LHDLEGAKRL | MNFWLSQDKD | ELEKVFG | 157 |

FIGURE 2

```
1    ATGCCTTCAG TAGAAAGTTT TGAGCTTGAT CATAATGCGG TTGTTGCTCC
51   ATATGTAAGA CATTGCGGCG TGCATAAAGT GGGAACAGAC GGCGTTGTAA
101  ATAAATTTGA CATTCGTTTT TGCCAGCCAA ATAAACAGGC GATGAAGCCT
151  GACACCATTC ACACACTCGA GCATTTGCTC GCGTTTACGA TTCGTTCTCA
201  CGCTGAGAAA TACGATCATT TTGATATCAT TGATATTTCT CCAATGGGCT
251  GCCAGACAGG CTATTATCTA GTTGTGAGCG GAGAGCCGAC ATCAGCGGAA
301  ATCGTTGATC TGCTTGAAGA CACAATGAAG GAAGCGGTAG AGATTACAGA
351  AATACCTGCT GCGAATGAAA AGCAGTGCGG CCAAGCGAAG CTTCATGATC
401  TGGAAGGCGC TAAACGTTTA ATGCGTTTCT GGCTTTCACA GGATAAAGAA
451  GAATTGCTAA AAGTATTTGG C
```

FIGURE 15

|  |  | 15 minutes post-exposure | | 30 minutes post-exposure | | |
|---|---|---|---|---|---|---|
| Locus | Common Name | 10μg/ml | 20μg/ml | 2.5μg/ml | 10μg/ml | 20μg/ml |
| Genes down-regulated | | | | | | |
| BA5583 | CTP synthase | -2.57 | -1.62 | -2.7 | -4.8 | -3.2 |
| BA0885 | S-layer protein Sap | -1.99 | -1.64 | -3.4 | -5.1 | -3.8 |
| BA1295 | immune inhibitor A metalloprotease | -2.37 | -1.84 | -5.7 | -3.3 | -3.3 |
| BA1449 | peptidase, M23/M37 family | -5.03 | -2.92 | -2.4 | -3.4 | -2.4 |
| BA2918 | hypothetical protein | -4.20 | -2.95 | -2.7 | -4.5 | -3.0 |
| BA5415 | cell division ABC transporter, permease protein FtsX | -4.60 | -3.09 | -2.6 | -3.1 | -2.8 |
| BA0796 | conserved hypothetical protein | -5.58 | -3.49 | -2.4 | -3.6 | -3.0 |
| Genes up-regulated | | | | | | |
| BA1639 | germination protein gerN | 3.64 | 5.41 | 2 | 2.1 | 2.6 |
| BA2239 | conserved hypothetical protein | 6.07 | 6.08 | 4.8 | 4.5 | 4.4 |
| BA1232 | enoyl-(acyl-carrier-protein) reductase | 3.43 | 2.90 | 5.6 | 4.5 | 4.8 |

FIGURE 19

SEQUENCE LISTING

<160> NUMBER OF SEQ ID NOS: 20

<210> SEQ ID NO 1
<211> LENGTH: 474
<212> TYPE: DNA
<213> ORGANISM: Bacillus anthracis

<400> SEQUENCE: 1

```
atgccatcag tagaaagctt tgaattagat catacgattg taaaggcacc ttatgtaaga      60
cattgcggag ttcacaatgt aggtagtgac ggtattgtaa ataaattcga tattcgtttt     120
tgccaaccga ataaacaagc aatgaaacca gatgttattc atacgttaga acatttatta     180
gcatttaatt tacgtaaata tattgatcgt tatccacatt ttgatattat cgatatttca     240
ccaatgggct gccaaacagg atactacctt gtagtaagcg gaacaccgac agttcgagaa     300
atcattgatt tattagaatt aacattaaaa gatgcggttc aaattacaga aattccagct     360
gcaaatgaaa cacaatgtgg tcaagcgaag cttcacgatt tagaaggagc aaaacgctta     420
atgaacttct ggttaagcca agataaagat gaacttgaga aagtatttgg ataa           474
```

<210> SEQ ID NO 2
<211> LENGTH: 157
<212> TYPE: PRT
<213> ORGANISM: Bacillus anthracis

<400> SEQUENCE: 2

```
Met Pro Ser Val Glu Ser Phe Glu Leu Asp His Thr Ile Val Lys Ala
1               5                   10                  15

Pro Tyr Val Arg His Cys Gly Val His Asn Val Gly Ser Asp Gly Ile
            20                  25                  30

Val Asn Lys Phe Asp Ile Arg Phe Cys Gln Pro Asn Lys Gln Ala Met
        35                  40                  45

Lys Pro Asp Val Ile His Thr Leu Glu His Leu Leu Ala Phe Asn Leu
    50                  55                  60

Arg Lys Tyr Ile Asp Arg Tyr Pro His Phe Asp Ile Ile Asp Ile Ser
65                  70                  75                  80

Pro Met Gly Cys Gln Thr Gly Tyr Tyr Leu Val Val Ser Gly Thr Pro
                85                  90                  95
```

```
Thr Val Arg Glu Ile Ile Asp Leu Leu Glu Leu Thr Leu Lys Asp Ala
            100                 105                 110

Val Gln Ile Thr Glu Ile Pro Ala Ala Asn Glu Thr Gln Cys Gly Gln
            115                 120                 125

Ala Lys Leu His Asp Leu Glu Gly Ala Lys Arg Leu Met Asn Phe Trp
130                 135                 140

Leu Ser Gln Asp Lys Asp Glu Leu Glu Lys Val Phe Gly
145                 150                 155

<210> SEQ ID NO 3
<211> LENGTH: 171
<212> TYPE: PRT
<213> ORGANISM: Escherichia coli

<400> SEQUENCE: 3

Met Pro Leu Leu Asp Ser Phe Thr Val Asp His Thr Arg Met Glu Ala
1               5                   10                  15

Pro Ala Val Arg Val Ala Lys Thr Met Asn Thr Pro His Gly Asp Ala
            20                  25                  30

Ile Thr Val Phe Asp Leu Arg Phe Cys Val Pro Asn Lys Glu Val Met
            35                  40                  45

Pro Glu Arg Gly Ile His Thr Leu Glu His Leu Phe Ala Gly Phe Met
50                  55                  60

Arg Asn His Leu Asn Gly Asn Gly Val Glu Ile Asp Ile Ser Pro
65                  70                  75                  80

Met Gly Cys Arg Thr Gly Phe Tyr Met Ser Leu Ile Gly Thr Pro Asp
                85                  90                  95

Glu Gln Arg Val Ala Asp Val Trp Lys Ala Ala Met Glu Asp Val Leu
            100                 105                 110

Lys Val Gln Asp Gln Asn Gln Ile Pro Glu Leu Asn Val Tyr Gln Cys
            115                 120                 125

Gly Thr Tyr Gln Met His Ser Leu Gln Glu Ala Gln Asp Ile Ala Arg
            130                 135                 140

Ser Ile Leu Glu Arg Asp Val Arg Ile Asn Ser Asn Glu Glu Leu Ala
145                 150                 155                 160

Leu Pro Lys Glu Lys Leu Gln Glu Leu His Ile
                165                 170

<210> SEQ ID NO 4
<211> LENGTH: 172
<212> TYPE: PRT
<213> ORGANISM: Vibrio harveyi

<400> SEQUENCE: 4

Met Pro Leu Leu Asp Ser Phe Thr Val Asp His Thr Arg Met Asn Ala
1               5                   10                  15

Pro Ala Val Arg Val Ala Lys Thr Met Gln Thr Pro Lys Gly Asp Thr
            20                  25                  30

Ile Thr Val Phe Asp Leu Arg Phe Thr Ala Pro Asn Lys Asp Ile Leu
            35                  40                  45

Ser Glu Lys Gly Ile His Thr Leu Glu His Leu Tyr Ala Gly Phe Met
50                  55                  60

Arg Asn His Leu Asn Gly Asp Ser Val Glu Ile Ile Asp Ile Ser Pro
65                  70                  75                  80

Met Gly Cys Arg Thr Gly Phe Tyr Met Ser Leu Ile Gly Thr Pro Ser
                85                  90                  95

Glu Gln Gln Val Ala Asp Ala Trp Ile Ala Ala Met Glu Asp Val Leu
```

```
            100                 105                 110
Lys Val Glu Asn Gln Asn Lys Ile Pro Glu Leu Asn Glu Tyr Gln Cys
        115                 120                 125

Gly Thr Ala Ala Met His Ser Leu Asp Glu Ala Lys Gln Ile Ala Lys
        130                 135                 140

Asn Ile Leu Glu Val Gly Val Ala Val Asn Lys Asn Asp Glu Leu Ala
145                 150                 155                 160

Leu Pro Glu Ser Met Leu Arg Glu Leu Arg Ile Asp
                165                 170

<210> SEQ ID NO 5
<211> LENGTH: 172
<212> TYPE: PRT
<213> ORGANISM: Vibrio cholerae

<400> SEQUENCE: 5

Met Pro Leu Leu Asp Ser Phe Thr Val Asp His Thr Arg Met Asn Ala
1               5                   10                  15

Pro Ala Val Arg Val Ala Lys Thr Met Gln Thr Pro Lys Gly Asp Thr
                20                  25                  30

Ile Thr Val Phe Asp Leu Arg Phe Thr Met Pro Asn Lys Asp Ile Leu
            35                  40                  45

Ser Glu Arg Gly Ile His Thr Leu Glu His Leu Tyr Ala Gly Phe Met
        50                  55                  60

Arg Asn His Leu Asn Gly Ser Gln Val Glu Ile Ile Asp Ile Ser Pro
65                  70                  75                  80

Met Gly Cys Arg Thr Gly Phe Tyr Met Ser Leu Ile Gly Ala Pro Thr
                85                  90                  95

Glu Gln Gln Val Ala Gln Ala Trp Leu Ala Ala Met Gln Asp Val Leu
            100                 105                 110

Lys Val Glu Ser Gln Glu Gln Ile Pro Glu Leu Asn Glu Tyr Gln Cys
        115                 120                 125

Gly Thr Ala Ala Met His Ser Leu Glu Glu Ala Lys Ala Ile Ala Lys
        130                 135                 140

Asn Val Ile Ala Ala Gly Ile Ser Val Asn Arg Asn Asp Glu Leu Ala
145                 150                 155                 160

Leu Pro Glu Ser Met Leu Asn Glu Leu Lys Val His
                165                 170

<210> SEQ ID NO 6
<211> LENGTH: 171
<212> TYPE: PRT
<213> ORGANISM: Yersinia pestis

<400> SEQUENCE: 6

Met Pro Leu

```
Glu Gln Arg Val Ala Asp Ala Trp Lys Ala Met Ala Asp Val Leu
            100                 105                 110

Lys Val Thr Asp Gln Arg Lys Ile Pro Glu Leu Asn Glu Tyr Gln Cys
        115                 120                 125

Gly Thr Tyr His Met His Ser Leu Glu Glu Ala Gln Ser Ile Ala Lys
    130                 135                 140

Asp Ile Leu Asp Arg Asp Val Arg Ile Asn His Asn Glu Glu Leu Ala
145                 150                 155                 160

Leu Pro Lys Glu Lys Leu Thr Glu Leu His Ile
                165                 170

<210> SEQ ID NO 7
<211> LENGTH: 167
<212> TYPE: PRT
<213> ORGANISM: Haemophilus influenzae

<400> SEQUENCE: 7

Met Pro Leu Leu Asp Ser Phe Lys Val Asp His Thr Lys Met Asn Ala
1               5                   10                  15

Pro Ala Val Arg Ile Ala Lys Thr Met Leu Thr Pro Lys Gly Asp Asn
            20                  25                  30

Ile Thr Val Phe Asp Leu Arg Phe Cys Ile Pro Asn Lys Glu Ile Leu
        35                  40                  45

Ser Pro Lys Gly Ile His Thr Leu Glu His Leu Phe Ala Gly Phe Met
    50                  55                  60

Arg Asp His Leu Asn Gly Asp Ser Ile Glu Ile Asp Ile Ser Pro
65                  70                  75                  80

Met Gly Cys Arg Thr Gly Phe Tyr Met Ser Leu Ile Gly Thr Pro Asn
                85                  90                  95

Glu Gln Lys Val Ser Glu Ala Trp Leu Ala Ser Met Gln Asp Val Leu
            100                 105                 110

Gly Val Gln Asp Gln Ala Ser Ile Pro Glu Leu Asn Ile Tyr Gln Cys
        115                 120                 125

Gly Ser Tyr Thr Glu His Ser Leu Glu Asp Ala His Glu Ile Ala Lys
    130                 135                 140

Asn Val Ile Ala Arg Gly Ile Gly Val Asn Lys Asn Glu Asp Leu Ser
145                 150                 155                 160

Leu Asp Asn Ser Leu Leu Lys
                165

<210> SEQ ID NO 8
<211> LENGTH: 168
<212> TYPE: PRT
<213> ORGANISM: Neisseria meningitidis

<400> SEQUENCE: 8

Met Pro Leu Leu Asp Ser Phe Lys Val Asp His Thr Arg Met His Ala
1               5                   10                  15

Pro Ala Val Arg Val Ala Lys Thr Met Thr Thr Pro Lys Gly Asp Thr
            20                  25                  30

Ile Thr Val Phe Asp Leu Arg Phe Cys Val Pro Asn Lys Glu Ile Leu
        35                  40                  45

Pro Glu Lys Gly Ile His Thr Leu Glu His Leu Phe Ala Gly Phe Met
    50                  55                  60

Arg Asp His Leu Asn Gly Asn Gly Val Glu Ile Ile Asp Ile Ser Pro
65                  70                  75                  80
```

Met Gly Cys Arg Thr Gly Phe Tyr Met Ser Leu Ile Gly Thr Pro Ser
                85                  90                  95

Glu Gln Gln Val Ala Asp Ala Trp Leu Ala Ser Met Gln Asp Val Leu
            100                 105                 110

Asn Val Lys Asp Gln Ser Lys Ile Pro Glu Leu Asn Glu Tyr Gln Cys
        115                 120                 125

Gly Thr Tyr Gln Met His Ser Leu Ala Glu Ala Gln Gln Ile Ala Gln
    130                 135                 140

Asn Val Leu Ala Arg Lys Val Ala Val Asn Lys Asn Glu Glu Leu Thr
145                 150                 155                 160

Leu Asp Glu Gly Leu Leu Asn Ala
                165

<210> SEQ ID NO 9
<211> LENGTH: 164
<212> TYPE: PRT
<213> ORGANISM: Campylobacter jejuni

<400> SEQUENCE: 9

Met Pro Leu Leu Asp Ser Phe Lys Val Asp His Thr Lys Met Pro Ala
1               5                   10                  15

Pro Ala Val Arg Leu Ala Lys Val Met Lys Thr Pro Lys Gly Asp Asp
            20                  25                  30

Ile Ser Val Phe Asp Leu Arg Phe Cys Ile Pro Asn Lys Asp Ile Met
        35                  40                  45

Ser Glu Lys Gly Thr His Thr Leu Glu His Leu Phe Ala Gly Phe Met
    50                  55                  60

Arg Asp His Leu Asn Ser Asn Ser Val Glu Ile Ile Asp Ile Ser Pro
65                  70                  75                  80

Met Gly Cys Arg Thr Gly Phe Tyr Met Ser Leu Ile Gly Thr Pro Asp
                85                  90                  95

Glu Lys Ser Ile Ala Lys Ala Trp Glu Ala Ala Met Lys Asp Val Leu
            100                 105                 110

Ser Val Ser Asp Gln Ser Lys Ile Pro Glu Leu Asn Ile Tyr Gln Cys
        115                 120                 125

Gly Thr Cys Ala Met His Ser Leu Asp Glu Ala Lys Gln Ile Ala Gln
    130                 135                 140

Lys Val Leu Asn Leu Gly Ile Ser Ile Ile Asn Asn Lys Glu Leu Lys
145                 150                 155                 160

Leu Glu Asn Ala

<210> SEQ ID NO 10
<211> LENGTH: 152
<212> TYPE: PRT
<213> ORGANISM: E. faecalis

<400> SEQUENCE: 10

Met Ala Arg Val Glu Ser Phe Glu Leu Asp His Asn Thr Val Lys Ala
1               5                   10                  15

Pro Tyr Val Arg Leu Ala Gly Thr Glu Gln Asn Gly Asp Ala Leu Val
            20                  25                  30

Glu Lys Tyr Asp Leu Arg Phe Leu Gln Pro Asn Lys Asp Ala Leu Pro
        35                  40                  45

Thr Gly Ala Leu His Thr Leu Glu His Leu Leu Ala Val Asn Met Arg
    50                  55                  60

Asp Glu Leu Lys Gly Ile Ile Asp Ile Ser Pro Met Gly Cys Arg Thr
65                  70                  75                  80

```
Gly Phe Tyr Met Ile Met Trp Asp Gln His Ser Pro Gln Glu Ile Arg
                85                  90                  95

Asp Ala Leu Val Asn Val Leu Asn Lys Val Ile Asn Thr Glu Val Val
                100                 105                 110

Pro Ala Val Ser Ala Lys Glu Cys Gly Asn Tyr Lys Asp His Ser Leu
                115                 120                 125

Phe Ala Ala Lys Glu Tyr Ala Lys Ile Val Leu Asp Gln Gly Ile Ser
                130                 135                 140

Leu Asp Pro Phe Glu Arg Ile Leu
145                 150

<210> SEQ ID NO 11
<211> LENGTH: 156
<212> TYPE: PRT
<213> ORGANISM: Staphylococcus aureus

<400> SEQUENCE: 11

Met Thr Lys Met Asn Val Glu Ser Phe Asn Leu Asp His Thr Lys Val
1               5                   10                  15

Val Ala Pro Phe Ile Arg Leu Ala Gly Thr Met Glu Gly Leu Asn Gly
                20                  25                  30

Asp Val Ile His Lys Tyr Asp Ile Arg Phe Lys Gln Pro Asn Lys Glu
                35                  40                  45

His Met Asp Met Pro Gly Leu His Ser Leu Glu His Leu Met Ala Glu
            50                  55                  60

Asn Ile Arg Asn His Ser Asp Lys Val Val Asp Leu Ser Pro Met Gly
65                  70                  75                  80

Cys Gln Thr Gly Phe Tyr Val Ser Phe Ile Asn His Asp Asn Tyr Asp
                85                  90                  95

Asp Val Leu Asn Ile Val Glu Ala Thr Leu Asn Asp Val Leu Asn Ala
                100                 105                 110

Thr Glu Val Pro Ala Cys Asn Glu Val Gln Cys Gly Trp Ala Ala Ser
                115                 120                 125

His Ser Leu Glu Gly Ala Lys Thr Ile Ala Gln Ala Phe Leu Asp Lys
            130                 135                 140

Arg Asn Glu Trp His Asp Val Phe Gly Thr Gly Lys
145                 150                 155

<210> SEQ ID NO 12
<211> LENGTH: 155
<212> TYPE: PRT
<213> ORGANISM: Helicobacter pylori

<400> SEQUENCE: 12

Met Lys Thr Pro Lys Met Asn Val Glu Ser Phe Asn Leu Asp His Thr
1               5                   10                  15

Lys Val Lys Ala Pro Tyr Val Arg Val Ala Asp Arg Lys Lys Gly Val
                20                  25                  30

Asn Gly Asp Leu Ile Val Lys Tyr Asp Val Arg Phe Lys Gln Pro Asn
                35                  40                  45

Gln Asp His Met Asp Met Pro Ser Leu His Ser Leu Glu His Leu Val
            50                  55                  60

Ala Glu Ile Ile Arg Asn His Ala Ser Tyr Val Val Asp Trp Ser Pro
65                  70                  75                  80

Met Gly Cys Gln Thr Gly Phe Tyr Leu Thr Val Leu Asn His Asp Asn
                85                  90                  95
```

Tyr Thr Glu Ile Leu Glu Val Leu Glu Lys Thr Met Gln Asp Val Leu
                100                 105                 110

Lys Ala Thr Glu Val Pro Ala Ser Asn Glu Lys Gln Cys Gly Trp Ala
            115                 120                 125

Ala Asn His Thr Leu Glu Gly Ala Lys Asp Leu Ala Arg Ala Phe Leu
        130                 135                 140

Asp Lys Arg Ala Glu Trp Ser Glu Val Gly Val
145                 150                 155

<210> SEQ ID NO 13
<211> LENGTH: 157
<212> TYPE: PRT
<213> ORGANISM: Bacillus subtilis

<400> SEQUENCE: 13

Met Pro Ser Val Glu Ser Phe Glu Leu Asp His Asn Ala Val Val Ala
1               5                   10                  15

Pro Tyr Val Arg His Cys Gly Val His Lys Val Gly Thr Asp Gly Val
            20                  25                  30

Val Asn Lys Phe Asp Ile Arg Phe Cys Gln Pro Asn Lys Gln Ala Met
        35                  40                  45

Lys Pro Asp Thr Ile His Thr Leu Glu His Leu Leu Ala Phe Thr Ile
    50                  55                  60

Arg Ser His Ala Glu Lys Tyr Asp His Phe Asp Ile Ile Asp Ile Ser
65                  70                  75                  80

Pro Met Gly Cys Gln Thr Gly Tyr Tyr Leu Val Val Ser Gly Glu Pro
                85                  90                  95

Thr Ser Ala Glu Ile Val Asp Leu Leu Glu Asp Thr Met Lys Glu Ala
            100                 105                 110

Val Glu Ile Thr Glu Ile Pro Ala Ala Asn Glu Lys Gln Cys Gly Gln
        115                 120                 125

Ala Lys Leu His Asp Leu Glu Gly Ala Lys Arg Leu Met Arg Phe Trp
    130                 135                 140

Leu Ser Gln Asp Lys Glu Glu Leu Leu Lys Val Phe Gly
145                 150                 155

<210> SEQ ID NO 14
<211> LENGTH: 158
<212> TYPE: PRT
<213> ORGANISM: Bacillus halodurans

<400> SEQUENCE: 14

Met Pro Thr Val Glu Ser Phe Glu Leu Asp His Thr Ile Val Lys Ala
1               5                   10                  15

Pro Phe Val Arg Pro Cys Gly Thr His Lys Val Gly Thr Asn Gly Glu
            20                  25                  30

Val Asn Lys Phe Asp Ile Arg Phe Phe Gln Pro Asn Lys Gln Ala Met
        35                  40                  45

Lys Pro Asp Val Ile His Thr Leu Glu His Leu Leu Ala Leu Asn Ile
    50                  55                  60

Arg Lys Phe Ala Glu Ala Tyr Asp His Phe Asp Val Ile Asp Leu Ser
65                  70                  75                  80

Pro Met Gly Cys Gln Thr Gly Pro Tyr Leu Ile Met Ser Gly Lys Pro
                85                  90                  95

Thr Val Glu Glu Ile Ile Asp Val Leu Glu Gln Thr Met Lys Tyr Ser
            100                 105                 110

Leu Glu Leu Glu Glu Val Pro Ala Ala Asn Glu Lys Gln Cys Gly Gln

```
                    115                 120                 125
Ala Lys Leu His Asp Leu Asp Gly Ala Lys Leu Met Thr Tyr Trp
130                 135                 140

Leu Ser His Glu Lys Asp Ser Leu Thr Lys Val Phe Glu Ser
145                 150                 155

<210> SEQ ID NO 15
<211> LENGTH: 155
<212> TYPE: PRT
<213> ORGANISM: Listeria monocytogenes

<400> SEQUENCE: 15

Met Ala Glu Lys Met Asn Val Glu Ser Phe Asn Leu Asp His Thr Lys
1               5                   10                  15

Val Lys Ala Pro Phe Val Arg Leu Ala Gly Thr Lys Val Gly Val His
                20                  25                  30

Gly Asp Glu Ile Tyr Lys Tyr Asp Val Arg Phe Lys Gln Pro Asn Lys
            35                  40                  45

Glu His Met Glu Met Pro Ala Leu His Ser Leu Glu His Leu Met Ala
        50                  55                  60

Glu Leu Ala Arg Asn His Thr Asp Lys Leu Val Asp Ile Ser Pro Met
65                  70                  75                  80

Gly Cys Gln Thr Gly Phe Tyr Val Ser Phe Ile Asn His Ser Asp Tyr
                85                  90                  95

Asp Asp Ala Leu Glu Ile Ile Ala Thr Thr Leu Thr Asp Val Leu Val
            100                 105                 110

Ala Thr Glu Val Pro Ala Cys Asn Glu Val Gln Cys Gly Trp Ala Ala
        115                 120                 125

Ser His Ser Leu Glu Gly Ala Lys Ala Leu Ala Glu Glu Phe Leu Ala
    130                 135                 140

Lys Arg Ser Glu Trp Lys Asn Val Phe Gly Glu
145                 150                 155

<210> SEQ ID NO 16
<211> LENGTH: 171
<212> TYPE: PRT
<213> ORGANISM: Clostridium botulinum

<400> SEQUENCE: 16

Met Val Lys Val Glu Ser Phe Ser Leu Asp His Thr Lys Val Lys Ala
1               5                   10                  15

Pro Phe Val Arg Lys Cys Gly Thr Gln Lys Gly Glu Met Gly Asp Thr
                20                  25                  30

Ile Thr Lys Phe Asp Leu Arg Phe Ser Gln Pro Asn Glu Glu Glu Met
            35                  40                  45

Pro Thr Gly Ala Val His Thr Leu Glu His Leu Leu Ala Gly Tyr Met
        50                  55                  60

Arg Glu Lys Met Asp Asn Ile Ile Asp Ile Ser Pro Met Gly Cys Arg
65                  70                  75                  80

Thr Gly Phe Tyr Leu Ile Ala Trp Gly Glu Val Glu Val Asp Thr Ile
                85                  90                  95

Ile Glu Ala Leu Asn Tyr Ser Leu Asn Lys Val Ile Glu Thr Glu Glu
            100                 105                 110

Val Pro Ala Thr Asn Ala Val Gln Cys Gly Asn Tyr Arg Asp His Ser
        115                 120                 125

Leu Phe Ser Ala Lys Glu Tyr Ala Lys His Val Leu Asn Gln Gly Ile
    130                 135                 140
```

```
Ser Asn Glu Val Phe Arg Glx Tyr Gln Arg Ala Tyr Arg Gln Tyr Pro
145                 150                 155                 160

Tyr Ser Lys Thr Glx Gln Phe Lys Tyr Glx Thr
                165                 170
```

<210> SEQ ID NO 17
<211> LENGTH: 160
<212> TYPE: PRT
<213> ORGANISM: Streptococcus pyogenes

<400> SEQUENCE: 17

```
Met Thr Lys Glu Val Ile Val Glu Ser Phe Glu Leu Asp His Thr Ile
1               5                   10                  15

Val Lys Ala Pro Tyr Val Arg Leu Ile Ser Glu Glu Phe Gly Pro Lys
                20                  25                  30

Gly Asp Arg Ile Thr Asn Phe Asp Val Arg Leu Val Gln Pro Asn Gln
            35                  40                  45

Asn Ser Ile Glu Thr Ala Gly Leu His Thr Ile Glu His Leu Leu Ala
50                  55                  60

Lys Leu Ile Arg Gln Arg Ile Asp Gly Met Ile Asp Cys Ser Pro Phe
65                  70                  75                  80

Gly Cys Arg Thr Gly Phe His Leu Ile Met Trp Gly Lys His Ser Ser
                85                  90                  95

Thr Asp Ile Ala Lys Val Ile Lys Ser Ser Leu Glu Glu Ile Ala Thr
            100                 105                 110

Gly Ile Thr Trp Glu Asp Val Pro Gly Thr Thr Leu Glu Ser Cys Gly
        115                 120                 125

Asn Tyr Lys Asp His Ser Leu Phe Ala Ala Lys Glu Trp Ala Gln Leu
130                 135                 140

Ile Ile Asp Gln Gly Ile Ser Asp Asp Pro Phe Ser Arg His Val Ile
145                 150                 155                 160
```

<210> SEQ ID NO 18
<211> LENGTH: 160
<212> TYPE: PRT
<213> ORGANISM: Streptococcus pneumoniae

<400> SEQUENCE: 18

```
Met Ser Lys Glu Val Ile Val Glu Ser Phe Glu Leu Asp His Thr Ile
1               5                   10                  15

Val Lys Ala Pro Tyr Val Arg Leu Ile Gly Glu Glu Thr Gly Pro Lys
                20                  25                  30

Gly Asp Ile Ile Ser Asn Tyr Asp Ile Arg Leu Val Gln Pro Asn Glu
            35                  40                  45

Asp Ser Ile Pro Thr Ala Gly Leu His Thr Ile Glu His Leu Leu Ala
50                  55                  60

Lys Leu Ile Arg Thr Arg Ile Asp Gly Met Ile Asp Cys Ser Pro Phe
65                  70                  75                  80

Gly Cys Arg Thr Gly Phe His Met Ile Met Trp Gly Arg His Thr Ser
                85                  90                  95

Ala Lys Ile Ala Ala Val Ile Lys Asp Ser Leu Lys Glu Ile Ala Glu
            100                 105                 110

Thr Thr Thr Trp Glu Asp Val Pro Gly Thr Thr Ile Glu Ser Cys Gly
        115                 120                 125

Asn Tyr Lys Asp His Ser Leu Phe Ser Ala Lys Glu Trp Ala Lys Leu
130                 135                 140
```

```
Ile Leu Glu Gln Gly Ile Ser Asp Asp Ala Phe Glu Arg His Val Ile
145                 150                 155                 160

<210> SEQ ID NO 19
<211> LENGTH: 171
<212> TYPE: PRT
<213> ORGANISM: Salmonella typhimurium

<400> SEQUENCE: 19

Met Pro Leu Leu Asp Ser Phe Ala Val Asp His Thr Arg Met Gln Ala
1               5                   10                  15

Pro Ala Val Arg Val Ala Lys Thr Met Asn Thr Pro His Gly Asp Ala
                20                  25                  30

Ile Thr Val Phe Asp Leu Arg Phe Cys Ile Pro Asn Lys Glu Val Met
                35                  40                  45

Pro Glu Lys Gly Ile His Thr Leu Glu His Leu Phe Ala Gly Phe Met
        50                  55                  60

Arg Asp His Leu Asn Gly Asn Gly Val Glu Ile Ile Asp Ile Ser Pro
65                  70                  75                  80

Met Gly Cys Arg Thr Gly Phe Tyr Met Ser Leu Ile Gly Thr Pro Asp
                85                  90                  95

Glu Gln Arg Val Ala Asp Ala Trp Lys Ala Ala Met Ala Asp Val Leu
                100                 105                 110

Lys Val Gln Asp Gln Asn Gln Ile Pro Glu Leu Asn Val Tyr Gln Cys
            115                 120                 125

Gly Thr Tyr Gln Met His Ser Leu Ser Glu Ala Gln Asp Ile Ala Arg
        130                 135                 140

His Ile Leu Glu Arg Asp Val Arg Val Asn Ser Asn Lys Glu Leu Ala
145                 150                 155                 160

Leu Pro Lys Glu Lys Leu Gln Glu Leu His Ile
                165                 170

<210> SEQ ID NO 20
<211> LENGTH: 471
<212> TYPE: DNA
<213> ORGANISM: Bacillus subtilis

<400> SEQUENCE: 20
atgccttcag tagaaagttt tgagcttgat cataatgcgg ttgttgctcc atatgtaaga      60
cattgcggcg tgcataaagt gggaacagac ggcgttgtaa ataaatttga cattcgtttt     120
tgccagccaa ataaacaggc gatgaagcct gacaccattc acacactcga gcatttgctc     180
gcgtttacga ttcgttctca cgctgagaaa tacgatcatt ttgatatcat tgatatttct     240
ccaatgggct gccagacagg ctattatcta gttgtgagcg gagagccgac atcagcggaa     300
atcgttgatc tgcttgaaga cacaatgaag gaagcggtag agattacaga aatacctgct     360
gcgaatgaaa agcagtgcgg ccaagcgaag cttcatgatc tggaaggcgc taaacgttta     420
atgcgtttct ggctttcaca ggataaagaa gaattgctaa aagtatttgg c              471
```

B. ANTHRACIS PREVENTION AND TREATMENT: MUTANT B. ANTHRACIS LACKING LUXS ACTIVITY AND FURANONE INHIBITION OF GROWTH, AI-2 QUORUM SENSING, AND TOXIN PRODUCTION

This application is a divisional of U.S. application Ser. No. 10/823,396 filed Apr. 12, 2004, now U.S. Pat. No. 7,365,184, which claims priority to U.S. Provisional Application Ser. No. 60/462,254 filed Apr. 11, 2003, and U.S. Provisional Application Ser. No. 60/462,255 filed Apr. 11, 2003, which are incorporated by reference herein in their entirety.

The research leading to this invention was supported, in part, by Grant No. RO1 GM 63270 awarded by the National Institutes of Health. Accordingly, the United States government may have certain rights to this invention.

FIELD OF THE INVENTION

The present invention pertains to the discovery that *B. anthracis* possesses a luxS gene that encodes a functional LuxS polypeptide, and that *B. anthracis* synthesizes a functional AI-2 quorum-sensing molecule. The invention provides mutant *B. anthracis* bacteria lacking a functional luxS gene, which do not produce a functional AI-2 molecule and have growth defects compared to wild-type *B. anthracis*. The invention also concerns methods for inhibiting the growth of *B. anthracis*, or for preventing or treating *B. anthracis* infection, by inhibiting the activity of the *B. anthracis* LuxS polypeptide, or by inhibiting the activity of the AI-2 quorum-sensing molecule. In particular, the invention concerns the use of furanones, especially furanones designated furanone 1-5 herein, to inhibit AI-2-mediated quorum-sensing, inhibit the growth of *B. anthracis*, inhibit anthrax toxin production, and prevent or treat *B. anthracis* infection. The invention further provides methods to prevent or treat *B. anthracis* infection by administration of a furanone to inhibit the expression or activity of protective antigen. The invention also provides methods to prevent or treat *B. anthracis* infection, or enhance an immune response to *B. anthracis* infection, by administering a vaccine comprising a *B. anthracis* cell in which the luxS gene is mutated.

BACKGROUND OF THE INVENTION

Quorum-sensing is the regulation of bacterial gene expression in response to change in cell density. Bacteria that utilize quorum-sensing signaling pathways synthesize signaling molecules (auto-inducers), which have been found in nature as N-homoserine lactones or small peptides (Miller and Bassler. Ann. Rev. Microbiol. 2001; 55:165-169). Auto-inducer levels are directly proportional to the size of the bacterial population (Fuqua, Parsek and Greenberg. Annu. Rev. Gen. 2002; 3:685-695), and at threshold levels, as detectable by bacterial cell receptors, auto-inducer binding alters bacterial gene expression (Miller and Bassler, supra). Quorum-sensing-based regulation of gene expression is critical for the pathogenesis of clinically important bacterial infections, such as those due to *Pseudomonas aeruginosa* in patients with cystic fibrosis (Erickson et al. Infect. Immun. 2001; 7:1783-1790), or *Vibrio cholerae* (Miller et al. Cell. 2002; 110:303-314).

Quorum-sensing has been well-characterized in *Vibrio harveyi*, bioluminescent bacteria that freely live in the ocean floor sediment or on the exterior of fish (Ramaiah et al. J. Appl. Microbiol. 2002; 93:108-116). The luminescence genes are expressed only when the *V. harveyi* populations are at high cell density, under the control of the lux quorum-sensing system. The luxCDABE operon, whose expressed polypeptides confer luminescence, is regulated by signaling pathways that are stimulated by the auto-inducer ligands, AI-1 (AHL) and AI-2. Synthesis of AI-1 requires the product of the luxM gene. AI-1 diffuses freely through the cell wall into the extracellular milieu, and when sufficient quantities are recognized by its sensor histidine kinase, LuxN, a hybrid two-component system-signaling cascade is initiated (Miller and Bassler, supra).

The *Vibrio harveyi* lux cascade also is regulated by another auto-inducer molecule, AI-2, which is predicted to be a furanosyl borate diester and synthesized by the product of the luxS gene. The luxS gene product converts S-ribosylhomocysteine to 4,5-dihydroxyl-2,3-pentanedione (DPD), catalyzing AI-2 formation (Chen et al. Nature 2001; 415:545-549). *V. harveyi* strain BB170, in which luxN is mutated, is unable to detect AI-1 molecules, and may be used to detect AI-2 or AI-2-like molecules in its milieu (Bassler, Wright and Silverman. Mol. Microbiol. 1994; 13:273-286).

Anthrax

*B. anthracis*, a gram-positive, non-motile, spore-forming bacterium, is the etiological agent of anthrax. Spores from *B. anthracis* are extremely resistant to a wide range of adverse environmental conditions, such as heat, ultraviolet and ionizing radiation, and chemical agents (Mock and Fouet. Annu. Rev. Microbiol. 2001; 55:647-671). *B. anthracis* Ames strain is very lethal, 100 spores is equal to one $LD_{50}$ (50% lethal dose). With the emergence of *B. anthracis* spores as a weapon of terror (Jernigan et al. Emer. Inf. Dis. 2001; 7:933-933), it is essential to develop new vaccines to prevent and new therapies to control *B. anthracis* infections. The anthrax vaccine currently licensed for human use in the United States is composed of a sterile culture supernatant of an attenuated pXO1+, pXO2 *B. anthracis* strain containing various amounts of the "protective antigen" discussed infra. This undefined nature of the components and the requirement for six immunizations over 18 months followed by annual boosters (3) suggest the need for an improved, alternative vaccines or treatments.

Recent data have shown that a furanone, (5Z)-4-bromo-5-(bromomethylene)-3-butyl-2(5H)-furanone, has the ability to inhibit AI-2-mediated quorum-sensing in *E. coli* and *V. harveyi* (Ren, Sims and Wood. Environ. Microbiol. 2001; 3:731-736), as well as swarming and biofilm formation by *B. subtilis* (Ren, Sims and Wood. Let. Appl. Microbil. 2002; 34:293-299). This furanone has been shown to directly inhibit both the AI-1 and AI-2-mediated quorum-sensing pathways (Ren, Sims and Wood. Environ. Microbiol. 2001; 3:731-736). Several natural furanones have been shown to reduce the growth rate of Gram-positive bacteria such as *Staphylococcus aureus* and *Staphylococcus epidermidis*, but to have no effect on mammalian cells (WO 99/53915 to Kjelleberg).

"Protective antigen" or "PA" is one of the three proteins making up the *B. anthracis* toxin, the agent which infects many mammalian species and may cause death. PA's role in the pathogenesis of *B. anthracis* infection is to bind to the anthrax toxin receptor (ATR) receptor in sensitive eukaryotic cells, thereby facilitating the translocation of the other two enzymatic toxin components, edema factor (EF) and lethal factor (LF), across the target cell membrane. PA associated with LF causes death when injected, whereas PA associated with EF produces edema. As PA is essential for infection of the target cell, methods to inhibit the expression of the PA gene (pag) or the function of the PA protein would be useful therapeutics to prevent or treat *B. anthracis* infection.

It has now been discovered that *B. anthracis* possesses a luxS gene that encodes a functional LuxS polypeptide, and that *B. anthracis* synthesizes a functional AI-2 molecule. It has also been found that mutant *B. anthracis* bacteria lacking the function of the luxS gene do not produce a functional AI-2 molecule and have growth defects compared to wild-type *B. anthracis*. It has also been discovered that a furanone, a compound that inhibits AI-2-mediated quorum-sensing, inhibits the growth of *B. anthracis*. The present invention therefore provides methods for inhibiting the growth of *B. anthracis* by inhibiting the activity of the *B. anthracis* LuxS polypeptide, or by inhibiting the activity of the AI-2 quorum-sensing molecule. Accordingly, the present invention provides methods for the prevention or treatment of *B. anthracis* infection by inhibiting the activity of the LuxS polypeptide and/or of AI-2 activity.

The present invention provides an advantage since live vaccines have a substantially greater probability of success in providing protection for the host against a subsequent invasion of a virulent wild strain than killed vaccines or subunit vaccines

SUMMARY OF THE INVENTION

The present invention is directed to an isolated nucleic acid molecule encoding a *B. anthracis* LuxS polypeptide. In preferred embodiments, the isolated nucleic acid encoding a *B. anthracis* LuxS polypeptide encodes a polypeptide comprising an amino acid sequence that is a least 90% identical to the amino acid sequence set forth in SEQ ID NO: 2. In particularly preferred embodiments, the isolated nucleic acid molecule encoding a *B. anthracis* LuxS polypeptide encodes a polypeptide comprising the amino acid sequence set forth in SEQ ID NO: 2. In preferred embodiments, the isolated nucleic acid molecule encoding a *B. anthracis* LuxS polypeptide comprises a nucleotide sequence that is at least 80% identical to the nucleotide sequence set forth in SEQ ID NO: 1. In particularly preferred embodiments, the isolated nucleic acid molecule encoding a *B. anthracis* LuxS polypeptide comprises the nucleotide sequence set forth in SEQ ID NO: 1.

The present invention is also directed to expression vectors comprising the nucleic acid molecules of the invention operatively associated with an expression control sequence, as well as host cells comprising such expression vectors. In exemplified embodiments, the host cells are *E. coli* cells.

The present invention is further directed to an isolated *B. anthracis* LuxS polypeptide. In preferred embodiments, the isolated *B. anthracis* LuxS polypeptide comprises an amino acid sequence that is a least 90% identical to the amino acid sequence set forth in SEQ ID NO: 2. In particularly preferred embodiments, the isolated *B. anthracis* LuxS polypeptide comprises the amino acid sequence set forth in SEQ ID NO: 2.

The present invention is also directed to a *B. anthracis* cell in which the luxS gene of the cell is mutated. For example, the invention contemplates a *B. anthracis* cell in which the luxS gene is mutated by removal of the nucleotide sequence set forth in SEQ ID NO: 1 from the genome of the cell. In an exemplified embodiment, the removed nucleotide sequence is replaced by a nucleotide sequence conferring antibiotic resistance, such as the *B. subtilis* aphA gene.

The present invention also provides a method for preventing or inhibiting the growth of a *B. anthracis* cell, which comprises inhibiting the activity of a *B. anthracis* LuxS polypeptide of the cell. In certain embodiments, the activity of the *B. anthracis* LuxS polypeptide is inhibited by mutating the luxS gene. In an exemplified embodiment, the luxS gene of *B. anthracis* is mutated by removing the nucleotide sequence set forth in SEQ ID NO: 1 and replacing it with a nucleotide sequence conferring antibiotic resistance, such as the *B. subtilis* aphA gene.

The present invention is directed to a method for preventing or inhibiting the growth of a *B. anthracis* cell, which comprises inhibiting the activity of an AI-2 quorum-sensing molecule of the cell. In certain embodiments, the activity of the AI-2 quorum-sensing molecule is inhibited by exposing the *B. anthracis* cell to a furanone selected from the group consisting of (5Z)-4-bromo-5-(bromomethylene)-3-butyl-2(5H)-furanone, 3-butyl-5-(dibromomethylene)-2-(5H)-furanone, 5-(bromomethylene)-2-(5H)-furanone, 4-bromo-5-(bromomethylene)-2(5H)-furanone, and 5-(dibromomethylene)-2-(5H)-furanone. In an exemplified embodiment, the activity of the AI-2 quorum-sensing molecule is inhibited by exposing the *B. anthracis* cell to (5Z)-4-bromo-5-(bromomethylene)-3-butyl-2(5H)-furanone.

The present invention is also directed to a method for preventing or inhibiting the delivery of *B. anthracis* toxin, which comprises inhibiting the gene expression, protein expression or protein activity of the *B. anthracis* protective antigen. In certain embodiments, the expression or activity of the *B. anthracis* protective antigen is inhibited by exposing the *B. anthracis* cell to a furanone selected from the group consisting of (5Z)-4-bromo-5-(bromomethylene)-3-butyl-2(5H)-furanone, 3-butyl-5-(dibromomethylene)-2-(5H)-furanone, 5-(bromomethylene)-2-(5H)-furanone, 4-bromo-5-(bromomethylene)-2(5H)-furanone, and 5-(dibromomethylene)-2-(5H)-furanone. In an exemplified embodiment, the expression of the *B. anthracis* protective antigen is inhibited by exposing the *B. anthracis* cell to (5Z)-4-bromo-5-(bromomethylene)-3-butyl-2(5H)-furanone.

The present invention also provides a method for the treatment or prevention of *B. anthracis* infection in a subject by administering to the subject a therapeutically effective amount of a furanone selected from the group consisting of (5Z)-4-bromo-5-(bromomethylene)-3-butyl-2(5H)-furanone, 3-butyl-5-(dibromomethylene)-2-(5H)-furanone, 5-(bromomethylene)-2-(5H)-furanone, 4-bromo-5-(bromomethylene)-2(5H)-furanone, and 5-(dibromomethylene)-2(5H)-furanone. In preferred embodiments the subject of the method is a human.

The present invention further provides methods for preventing *B. anthracis* infection in a subject, and for enhancing an immune response to *B. anthracis* infection in a subject, by administering to a subject a vaccine comprising *B. anthracis* cells having a mutated luxS gene. In an exemplified embodiment, the luxS gene of *B. anthracis* is mutated by removing the nucleotide sequence set forth in SEQ ID NO: 1 and replacing it with a nucleotide sequence conferring antibiotic resistance, such as the *B. subtilis* aphA gene.

The present invention is further directed to pharmaceutical compositions and vaccines. The pharmaceutical compositions of the invention comprise a *B. anthracis* LuxS polypeptide inhibitor, an AI-2 quorum-sensing molecule inhibitor, or a protective antigen protein inhibitor and a pharmaceutically acceptable carrier. In preferred embodiments the AI-2 quorum-sensing molecule inhibitor or protective antigen protein inhibitor is a furanone selected from the group consisting of (5Z)-4-bromo-5-(bromomethylene)-3-butyl-2(5H)-furanone, 3-butyl-5-(dibromomethylene)-2-(5H)-furanone, 5-(bromomethylene)-2-(5H)-furanone, 4-bromo-5-(bromomethylene)-2(5H)-furanone, and 5-(dibromomethylene)-2(5H)-furanone. The invention is also directed to a vaccine comprising *B. anthracis* cells having a mutated luxS gene and a pharmaceutically acceptable carrier. In an exemplified embodiment, the luxS gene of *B. anthracis* is mutated by removing the nucleotide sequence set forth in SEQ ID NO: 1 and replacing it with a nucleotide sequence conferring antibiotic resistance, such as the *B. subtilis* aphA gene. The vaccine can be administered to human subjects to prevent or treat infection with *B. anthracis*.

DESCRIPTION OF THE DRAWINGS

FIG. 1 depicts the nucleotide sequence of the *B. anthracis* luxS gene (SEQ ID NO: 1). Nucleic acid residues are indicated by standard one letter abbreviation.

FIG. 2 depicts the translated amino acid sequence of the *B. anthracis* LuxS gene (SEQ ID NO: 2). Amino acid residues are indicated by standard one letter abbreviation.

FIG. 15 depicts the nucleotide sequence of the *B. subtilis* luxS gene (SEQ ID NO: 20). Nucleic acid residues are indicated by standard one letter abbreviation.

FIG. 19 is a table summarizing the genes which were identified by microarray analysis to be up- and down-regulated in furanone 1-treated *B. anthracis* compared to untreated controls.

DETAILED DESCRIPTION

Figure 3:
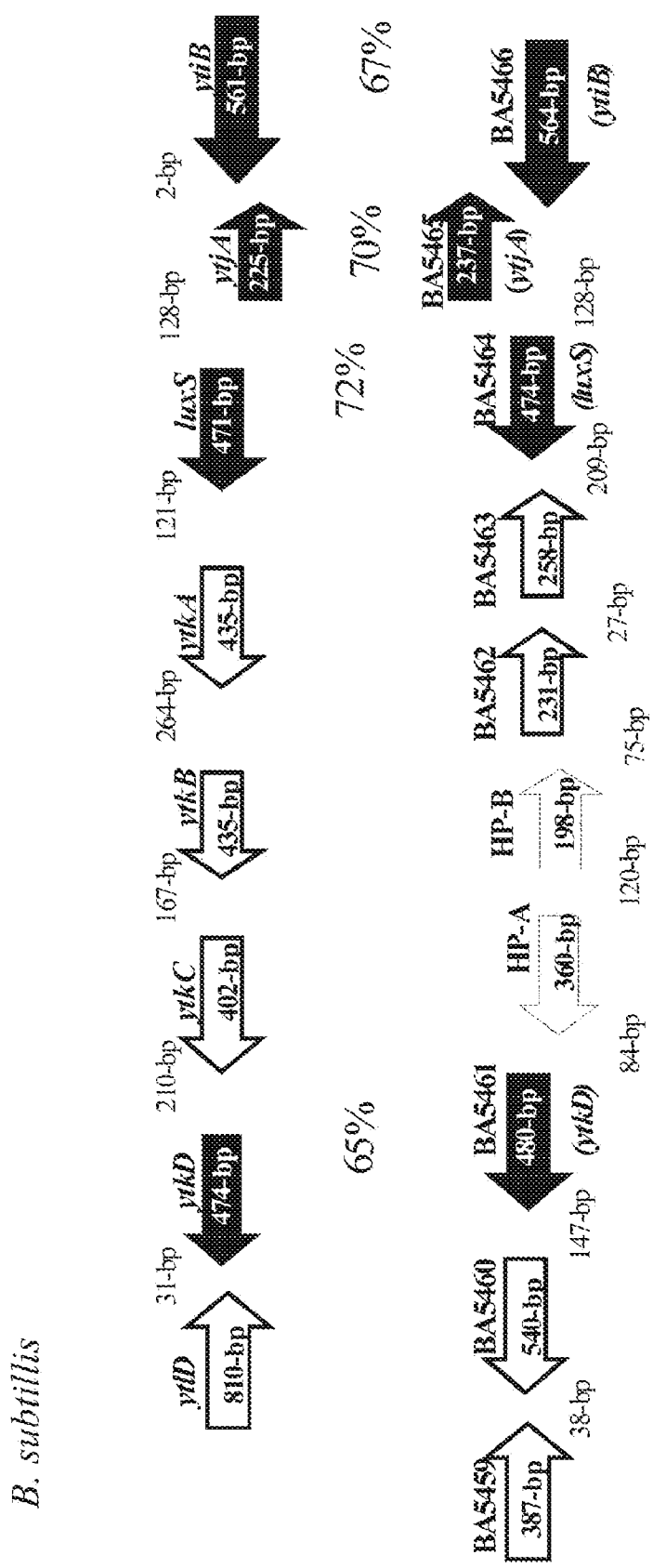
FIG. 3 is a schematic of *B. anthracis* chromosomal organization in the region of the luxS gene, ORF BA5464, and corresponding region of the *B. subtilis* chromosome. Arrows indicate direction of transcription, and shading indicates pairs of homologous genes.

The present invention involves the discovery that *B. anthracis* possesses a luxS gene that encodes a functional LuxS polypeptide, and that this luxS gene is required for production of an AI-2 molecule by, and for normal cell growth of, *B. anthracis*. In addition, the present invention involves the discovery that the growth of *B. anthracis* may be inhibited by inhibiting the activity of the *B. anthracis* LuxS polypeptide or AI-2 molecule. Furanone compounds that can be administered to treat or prevent *B. anthracis* infection are also disclosed.

Numerous references, including patents, patent applications, and various publications are cited and discussed in the description of this invention. The citation and/or discussion of such references is provided merely to clarify the description of the present invention and is not an admission that any such reference is "prior art" to the present invention. All references cited and discussed in this specification are incorporated herein by reference in their entirety and to the same extent as if each reference was individually incorporated by reference.

DEFINITIONS

In accordance with the present invention there may be employed conventional molecular biology, microbiology, protein expression and purification, antibody, and recombinant DNA techniques within the skill of the art. Such techniques are explained fully in the literature. See, e.g., Sambrook, Fritsch and Maniatis, *Molecular Cloning: A Laboratory Manual*, Second Edition (Cold Spring Harbor Laboratory Press, New York: 1989); *DNA Cloning: A Practical Approach*, Volumes I and II (Glover ed.: 1985); *Oligonucleotide Synthesis* (Gait ed.: 1984); *Nucleic Acid Hybridization* (Hames & Higgins eds.: 1985); *Transcription And Translation* (Hames & Higgins, eds.: 1984); *Animal Cell Culture* (Freshney, ed.: 1986); *Immobilized Cells And Enzymes* (IRL Press: 1986); Perbal, *A Practical Guide To Molecular Cloning* (1984); Ausubel et al., eds. *Current Protocols in Molecular Biology*, (John Wiley & Sons, Inc.: 1994); and Harlow and Lane. *Antibodies: A Laboratory Manual* (Cold Spring Harbor Laboratory Press: 1988).

The term "about" or "approximately" means within an acceptable error range for the particular value as determined by one of ordinary skill in the art, which will depend in part on how the value is measured or determined, i.e., the limitations of the measurement system, i.e., the degree of precision required for a particular purpose, such as a pharmaceutical formulation. For example, "about" can mean within 1 or more than 1 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

As used herein, the term "isolated" means that the referenced material is removed from the environment in which it is normally found. Thus, an isolated biological material can be free of cellular components, i.e., components of the cells in which the material is found or produced. Isolated nucleic acid molecules include, for example, a PCR product, an isolated mRNA, a cDNA, or a restriction fragment. Isolated nucleic acid molecules also include, for example, sequences inserted into plasmids, cosmids, artificial chromosomes, and the like. An isolated nucleic acid molecule is preferably excised from the genome in which it may be found, and more preferably is no longer joined to non-regulatory sequences, non-coding sequences, or to other genes located upstream or downstream of the nucleic acid molecule when found within the genome. An isolated protein may be associated with other proteins or nucleic acids, or both, with which it associates in the cell, or with cellular membranes if it is a membrane-associated protein.

By "substantially identical" is meant a polypeptide or nucleic acid molecule exhibiting at least 80%, more preferably at least 90%, and most preferably at least 95% identity in comparison to a reference amino acid or nucleic acid sequence. For polypeptides, the length of sequence comparison will generally be at least 20 amino acids, preferably at least 30 amino acids, more preferably at least 40 amino acids, and most preferably at least 50 amino acids. For nucleic acid molecules, the length of sequence comparison will generally be at least 60 nucleotides, preferably at least 90 nucleotides, and more preferably at least 120 nucleotides.

The degree of sequence identity between any two nucleic acid molecules or two polypeptides may be determined by sequence comparison and alignment algorithms known in the art, including but not limited to BLAST, FASTA, DNA Strider, and the GCG Package (Madison, Wis.) pileup program (see, for example, Gribskov and Devereux *Sequence Analysis Primer* (Stockton Press: 1991) and references cited therein). The percent similarity between two nucleotide sequences may be determined, for example, using the Smith-Waterman algorithm as implemented in the BESTFIT software program using default parameters.

By "expression construct" is meant a nucleic acid sequence comprising a target nucleic acid sequence or sequences whose expression is desired, operatively associated with expression control sequence elements which provide for the proper transcription and translation of the target nucleic acid sequence(s) within the chosen host cells. Such sequence elements may include a promoter and a polyadenylation signal. The "expression construct" may further comprise "vector sequences". By "vector sequences" is meant any of several nucleic acid sequences established in the art which have utility in the recombinant DNA technologies of the invention to facilitate the cloning and propagation of the expression constructs including (but not limited to) plasmids, cosmids, phage vectors, viral vectors, and yeast artificial chromosomes.

By "operatively associated with" is meant that a target nucleic acid sequence and one or more expression control sequences (e.g., promoters) are physically linked so as to permit expression of the polypeptide encoded by the target nucleic acid sequence within a host cell.

By "host cell" is meant a cell which has been transfected with one or more expression constructs of the invention. Exemplary host cells include various strains of *E. coli*.

By "transfection" is meant the process of introducing one or more of the expression constructs of the invention into a host cell by any of the methods well established in the art, including (but not limited to) microinjection, electroporation, liposome-mediated transfection, calcium phosphate-mediated transfection, or virus-mediated transfection.

As used herein, the term "gene" refers to a DNA sequence that codes for or corresponds to a particular sequence of amino acids which comprise all or part of one or more polypeptides, e.g., LuxS, and may or may not include regulatory DNA sequences (e.g., promoter sequences), which determine, for example, the conditions under which the gene is expressed.

As used herein, the terms "mutant" and "mutation" refer to any detectable change in genetic material (e.g., DNA) or any process, mechanism, or result of such a change. This includes gene mutations, in which the structure (e.g., DNA sequence) of a gene is altered, any gene or DNA arising from any mutation process, and any expression product (e.g., protein or enzyme) expressed by a modified gene or DNA sequence. As used herein, the term "mutating" refers to a process of creating a mutant or mutation.

As used herein, the term "furanone" encompasses (5Z)-4-bromo-5-(bromomethylene)-3-butyl-2(5H)-furanone ("furanone 1"), 3-butyl-5-(dibromomethylene)-2-(5H)-furanone ("furanone 2"), 5-(bromomethylene)-2-(5H)-furanone ("furanone 3"), 4-bromo-5-(bromomethylene)-2(5H)-furanone ("furanone 4"), and 5-(dibromomethylene)-2(5H)-furanone ("furanone 5"). The chemical structure these furanones are described further below.

The phrase "therapeutically effective amount" is used herein to mean an amount sufficient to reduce by at least about 15 percent, preferably by at least 50 percent, more preferably by at least 90 percent, and most preferably prevent, a clinically significant deficit in the activity, function and response of the host. Alternatively, a therapeutically effective amount is sufficient to cause an improvement in a clinically significant condition in the host. The host may be a mammal, preferably a human.

According to the present invention, a therapeutically effective amount of a LuxS inhibitor, furanone compound will be an amount that is effective treat or prevent the pathological conditions associated with $B.$ $anthracis$ infection in a subject. A therapeutically effective amount of a vaccine comprising $B.$ $anthracis$ cells containing mutated LuxS will be the amount of cells required to induce an immune response sufficient to protect an animal against disease As used herein, the term "subject" refers to a mammal, preferably a human, who has been exposed to or infected with, or is at risk of being exposed to or infected with, $B.$ $anthracis$ or $B.$ $antracis$ spores.

As used herein, the phrase "pharmaceutically acceptable" refers to molecular entities and compositions that are "generally regarded as safe", e.g., that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans.

The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Alternatively, the carrier can be a solid dosage form carrier, including but not limited to one or more of a binder (for compressed pills), a glidant, an encapsulating agent, a flavorant, and a colorant. Suitable pharmaceutical carriers are described in "Remington's Pharmaceutical Sciences" by E. W. Martin.

As used herein, the term "vaccine" refers to a composition comprising a cell or a cellular antigen, and optionally other pharmaceutically acceptable carriers, administered to stimulate an immune response in an animal, preferably a mammal, most preferably a human, specifically against the antigen and preferably to engender immunological memory that leads to mounting of a protective immune response should the subject encounter that antigen at some future time. In the vaccines of the present invention, the vaccine comprises $B.$ $anthracis$ bacteria that have been attenuated by loss of luxS gene function. These attenuated $B.$ $anthracis$ bacteria have been manipulated to lose some or all of their ability to grow in a host. Vaccines often comprise an adjuvant.

An "immune response" refers to the development in the host of a cellular and/or antibody-mediated immune response to a composition or vaccine of interest. Such a response usually consists of the subject producing antibodies, B cells, helper T cells, suppressor T cells, and/or cytotoxic T cells directed specifically to an antigen or antigens included in the composition or vaccine of interest.

As used herein, the term "adjuvant" refers to a compound or mixture that enhances the immune response to an antigen. An adjuvant can serve as a tissue depot that slowly releases the antigen and also as a lymphoid system activator that non-specifically enhances the immune response (Hood et al., Immunology, Second Ed., 1984, Benjamin/Cummings: Menlo Park, Calif., p. 384). Often, a primary challenge with an antigen alone, in the absence of an adjuvant, will fail to elicit a humoral or cellular immune response. Adjuvants include, but are not limited to, complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions, keyhole limpet hemocyanins, and potentially useful human adjuvants such as N-acetyl-muramyl-L-threonyl-D-isoglutamine (thr-MDP), N-acetyl-nor-muramyl-L-alanyl-D-isoglutamine, N-acetylmuramyl-L-alanyl-D-isoglutaminyl-L-alanine-2-(1'-2'-dipalmitoyl-sn-glycero-3-hydroxyphosphoryloxy)-ethylamine, BCG (bacille Calmette-Guerin) and $Corynebacterium$ $parvum$. Preferably, the adjuvant is pharmaceutically acceptable.

The present invention provides isolated nucleic acid molecules encoding a $B.$ $anthracis$ LuxS polypeptide. As used herein, the term "LuxS polypeptide" means a polypeptide capable of converting S-ribosylhomocysteine to 4,5-dihydroxyl-2,3-pentanedione (DPD). In preferred embodiments, the primary amino acid sequence of the LuxS polypeptide is substantially identical to that of the native $B.$ $anthracis$ LuxS polypeptide (as shown in SEQ ID NO: 2). Such a LuxS polypeptide may be encoded by a nucleic acid sequence that is substantially identical to that of the native $B.$ $anthracis$ luxS sequence (as shown in SEQ ID NO: 1).

LuxS Nucleic Acids and Polypeptides

The ability of a nucleic acid molecule to encode a $B.$ $anthracis$ LuxS polypeptide may be determined, for example, using $V.$ $harveyi$ strain BB170 in the $V.$ $harveyi$ bioluminescence assay (see, e.g. Surette and Bassler. Proc. Natl. Acad. Sci. USA 1998; 95:7046-7050; and Example 3). $V.$ $harveyi$ strain BB170 up-regulates expression of the lux operon, and therefore only exhibits bioluminescence, when AI-2 or AI-2-like molecules are present in its milieu (Bassler, Wright and Silverman. Mol. Microbiol. 1994; 13:273-286). Thus, for this assay, *V. harveyi* strain BB170 cells are cultured in the presence of a test sample (e.g., cell free medium prepared from a bacterial culture), and the degree of bioluminescence induced is measured by standard techniques. Samples which contain a functional LuxS polypeptide, and hence, an AI-2 molecule will induce bioluminescence. This assay can also be used to test the efficacy of inhibitors of AI-1 or AI-2 molecule synthesis.

For this assay, an expression vector comprising the nucleic acid molecule is expressed in host cells of *E. coli* strain DH5α® strain, a commonly used laboratory strain of *E. coli* that contains a frameshift mutation in the 3' portion of the *E. coli* luxS gene open reading frame, and therefore fails to produce measurable amounts of AI-2 (Surrette, Miller and Bassler. Proc. Natl. Acad. Sci. USA 1999; 96:1639-1644). As a result, conditioned cell free medium (CFM) prepared from cultures of *E. coli* strain DH5α® strain normally fails to induce bioluminescence in the *V. harveyi* bioluminescence assay. A nucleic acid sequence that encodes a *B. anthracis* LuxS polypeptide will complement the luxS gene mutation of *E. coli* strain DH5α® strain and restore synthesis of the AI-2 molecule. As a result, CFM prepared from cultures of such *E. coli* host cells will induce bioluminescence in the *V. harveyi* bioluminescence assay.

The *B. anthracis* LuxS encoding nucleic acid molecules of the invention may be produced by any of a number of techniques well established in the art, including (but not limited to) amplification using the PCR reaction, cDNA cloning, genomic DNA cloning, or synthetic means.

The present invention also provides expression vectors comprising nucleic acid molecules encoding a *B. anthracis* LuxS polypeptide. The expression constructs of the invention comprise elements necessary for proper transcription and translation of a *B. anthracis* LuxS-encoding sequence within the chosen host cells, including a promoter, a polyadenylation signal, and optionally internal ribosome entry sites (IRES) and other ribosome binding site sequences, enhancers, response elements, suppressors, signal sequences, and the like. Codon selection, where the target nucleic acid sequence of the construct is engineered or chosen so as to contain codons preferentially used within the desired host call, may be used to minimize premature translation termination and thereby maximize expression.

The inserted nucleic acid sequence may also encode a polypeptide tag for easy identification and purification of the translated LuxS polypeptide. Preferred polypeptide tags include GST, myc, His, and FLAG tags. The encoded polypeptide tag may include recognition sites for site-specific proteolysis or chemical agent cleavage to facilitate removal of the polypeptide tag following protein purification. For example a thrombin cleavage site could be incorporated between the LuxS polypeptide and its polypeptide tag.

The inserted nucleic acid sequence may also encode a signal peptide to provide for secretion of the translated LuxS polypeptide from the host cell. Suitable signal peptides are known in the art and include, but are not limited to, PhoA, OmpA, PelP signal peptides.

The promoter sequences may be endogenous or heterologous to the host cell to be modified, and may provide ubiquitous (i.e., expression occurs in the absence of an apparent external stimulus) or inducible (i.e., expression only occurs in presence of particular stimuli) expression. Promoters which may be used to control gene expression include, but are not limited to, cytomegalovirus (CMV) promoter (U.S. Pat. No. 5,385,839 and No. 5,168,062), the SV40 early promoter region (Benoist and Chambon, Nature 1981; 290:304-310), the promoter contained in the 3' long terminal repeat of Rous sarcoma virus (Yamamoto, et al., Cell 1980; 22:787-797), the herpes thymidine kinase promoter (Wagner et al., Proc. Natl. Acad. Sci. USA 1981; 78:1441-1445), the regulatory sequences of the metallothionein gene (Brinster et al., Nature 1982; 296:39-42); prokaryotic promoters such as the alkaline phosphatase promoter, the trp-lac promoter, the bacteriophage lamba $P_L$ promoter, the T7 promoter, the beta-lactamase promoter (VIIIa-Komaroff, et al., Proc. Natl. Acad. Sci. USA 1978; 75:3727-3731), or the tac promoter (DeBoer, et al., Proc. Natl. Acad. Sci. USA 1983; 80:21-25); see also "Useful proteins from recombinant bacteria" in Scientific American 1980; 242:74-94; promoter elements from yeast or other fungi such as the Gal4 promoter, the ADC (alcohol dehydrogenase) promoter, and the PGK (phosphoglycerol kinase) promoter.

The expression constructs may further comprise vector sequences that facilitate the cloning and propagation of the expression constructs. A large number of vectors, including plasmid and fungal vectors, have been described for replication and/or expression in a variety of eukaryotic and prokaryotic host cells. Standard vectors useful in the current invention are well known in the art and include (but are not limited to) plasmids, cosmids, phage vectors, viral vectors, and yeast artificial chromosomes. The vector sequences may contain a replication origin for propagation in *E. coli*; the SV40 origin of replication; an ampicillin, neomycin, or puromycin resistance gene for selection in host cells; and/or genes (e.g., dihydrofolate reductase gene) that amplify the dominant selectable marker plus the gene of interest.

For example, a plasmid is a common type of vector. A plasmid is generally a self-contained molecule of double-stranded DNA, usually of bacterial origin, that can readily accept additional foreign DNA and that can readily be introduced into a suitable host cell. A plasmid vector generally has one or more unique restriction sites suitable for inserting foreign DNA. Examples of plasmids that may be used for expression in prokaryotic cells include, but are not limited to, pBR322-derived plasmids, pEMBL-derived plasmids, pEX-derived plasmids, pBTac-derived plasmids, and pUC-derived plasmids.

The present invention also provides host cells comprising the expression vectors of the invention. Exemplary host cells include various strains of *E. coli*. Techniques for introduction of nucleic acids to host cells are well established in the art, including, but not limited to, electroporation, microinjection, liposome-mediated transfection, calcium phosphate-mediated transfection, or virus-mediated transfection (see, for example, *Artificial self-assembling systems for gene delivery*. Felgner, et al., eds. (Oxford University Press: 1996); Lebkowski, et al. Mol Cell Biol 1988; 8:3988-3996; Sambrook, et al. *Molecular Cloning: A Laboratory Manual.* $2^{nd}$ Edition (Cold Spring Harbor Laboratory: 1989); and Ausubel, et al., eds. *Current Protocols in Molecular Biology* (John Wiley & Sons: 1989)).

The present invention also provides an isolated *B. anthracis* LuxS polypeptide. The isolated LuxS polypeptides of the invention may be purified to reduce or eliminate the presence of unrelated materials (i.e., contaminants) including native materials from which the material is obtained. For example, a purified polypeptide is preferably substantially free of other polypeptides or nucleic acids with which it is associated in a cell. As used herein, the term "substantially free" is used operationally, in the context of analytical testing of the material. Preferably, purified material substantially free of contaminants is at least 50% pure; more preferably, at least 90% pure, and more preferably still at least 99% pure. Purity can be evaluated by chromatography, gel electrophoresis, immunoassay, composition analysis, biological assay, and other methods known in the art.

Methods for polypeptide purification are well-known in the art, including, without limitation, preparative disc-gel electrophoresis and isoelectric focusing; affinity, HPLC, reversed-phase HPLC, gel filtration or size exclusion, ion exchange and partition chromatography; precipitation and salting-out chromatography; extraction; and countercurrent distribution.

For example, a LuxS polypeptide may be produced in an in vitro translation reaction using a LuxS encoding nucleic acid molecule of the invention. Alternatively, the LuxS polypeptide may be produced by expression within a host cell of an expression construct of the invention, followed by isolation of the produced LuxS polypeptide. In such embodiments, it may be preferable to produce the polypeptide in a host cell using an expression construct in which the LuxS encoding sequences are linked to a polypeptide tag that facilitates purification, such as, but not limited to, a His, FLAG or GST tag. The encoded polypeptide tag may include recognition sites for site-specific proteolysis or chemical agent cleavage to facilitate removal of the polypeptide tag following protein purification. For example a thrombin cleavage site could be incorporated between the LuxS polypeptide and its polypeptide tag. Following expression within a host cell, a LuxS polypeptide can then be purified from a crude lysate of the host cell, for example, by chromatography on an appropriate solid-phase matrix, or using antibodies produced against the LuxS polypeptide or against the polypeptide tag.

LuxS Antibodies

The present invention also pertains to an antibody which binds to a B. anthracis LuxS polypeptide. Said antibodies are immunospecific for antigenic determinants of the B. anthracis LuxS polypeptides of the present invention. For instance, a favored anti-LuxS antibody of the present invention does not recognize a polypeptide whose amino acid sequence is less than 90 percent identical to that shown in SEQ ID NO: 2.

According to the invention, an isolated B. anthracis LuxS polypeptide produced recombinantly or by chemical synthesis, and fragments or other derivatives or analogs thereof, including fusion proteins, may be used as an immunogen to generate antibodies that recognize the B. anthracis LuxS polypeptide. Such antibodies include but are not limited to polyclonal, monoclonal, chimeric, single chain, Fab fragments, and a Fab expression library.

Various procedures known in the art may be used for the production of polyclonal antibodies to a B. anthracis LuxS polypeptide or derivative or analog thereof. For the production of antibody, various host animals can be immunized by injection with the a B. anthracis LuxS polypeptide, or a derivative (e.g., fragment or fusion protein) thereof, including but not limited to rabbits, hamsters, mice, rats, sheep, goats, etc. In one embodiment, the B. anthracis LuxS polypeptide or fragment thereof can be conjugated to an immunogenic carrier, e.g., bovine serum albumin (BSA) or keyhole limpet hemocyanin (KLH). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and Corynebacterium parvum. Following immunization, anti-LuxS antisera can be obtained and, if desired, polyclonal anti-LuxS antibodies isolated from the serum.

For preparation of monoclonal antibodies directed toward the B. anthracis LuxS polypeptide, or fragment, analog, or derivative thereof, any technique that provides for the production of antibody molecules by continuous cell lines in culture may be used. These include but are not limited to the hybridoma technique originally developed by Kohler and Milstein (Nature 1975; 256:495-497), as well as the trioma technique, the human B-cell hybridoma technique (Kozbor et al., Immunology Today 1983; 4:72; Cote et al., Proc. Natl. Acad. Sci. U.S.A. 1983; 80:2026-2030), and the EBV-hybridoma technique to produce human monoclonal antibodies (Cole et al., in Monoclonal Antibodies and Cancer Therapy, Alan R. Liss, Inc., pp. 77-96, 1985). Hybridoma cells can be screened immunochemically for production of antibodies specifically reactive with a LuxS polypeptide of the present invention, and monoclonal antibodies isolated from a culture comprising such hybridoma cells.

In an additional embodiment of the invention, monoclonal antibodies can be produced in germ-free animals (International Patent Publication No. WO 89/12690, published 28 Dec. 1989). In anther embodiment, techniques developed for the production of "chimeric antibodies" (Morrison et al., J. Bacteriol. 1984; 159:870; Neuberger et al., Nature 1984; 312:604-608; Takeda et al., Nature 1985; 314:452-454,) by splicing the genes from a mouse antibody molecule specific for an B. anthracis LuxS polypeptide together with genes from a human antibody molecule of appropriate biological activity can be used. Such human or humanized chimeric antibodies are preferred for use in therapy of human diseases or disorders related to B. anthracis infection, since the human or humanized antibodies are much less likely than xenogenic antibodies to induce an immune response, in particular an allergic response, themselves.

According to the invention, techniques described for the production of single chain antibodies (U.S. Pat. Nos. 5,476, 786 and 5,132,405 to Huston; U.S. Pat. No. 4,946,778) can be adapted to produce B. anthracis LuxS polypeptide-specific single chain antibodies. Indeed, these sequences encoding single chain antibodies can be delivered for expression in vivo. An additional embodiment of the invention utilizes the techniques described for the construction of Fab expression libraries (Huse et al., Science 1989; 246:1275-1281) to allow rapid and easy identification of monoclonal Fab fragments with the desired specificity for a B. anthracis LuxS polypeptide, or its derivatives, or analogs.

In the production of antibodies, screening for the desired antibody can be accomplished by techniques known in the art, e.g., radioimmunoassay, ELISA (enzyme-linked immunosorbant assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. For example, to select antibodies which recognize a specific epitope of a B. anthracis LuxS polypeptide, one may assay generated hybridomas for a product which binds to a B. anthracis LuxS polypeptide fragment containing such epitope.

The term antibody as used herein is intended to include fragments thereof which are also reactive with one of the subject B. anthracis LuxS polypeptides. For example, such fragments include but are not limited to: the F(ab)$_2$ fragment which can be produced by pepsin digestion of the antibody molecule; the Fab fragments which can be generated by reducing the disulfide bridges of the F(ab)$_2$ fragment, and the Fab fragments which can be generated by treating the antibody molecule with papain and a reducing agent.

The foregoing antibodies can be used in methods known in the art relating to the localization and activity of a *B. anthracis* LuxS polypeptide, e.g., for Western blotting, imaging a *B. anthracis* LuxS polypeptide in situ, measuring levels thereof in appropriate physiological samples, etc. using any of the detection techniques mentioned above or known in the art.

LuxS Mutants

The present invention also provides *B. anthracis* bacteria in which the *B. anthracis* luxS gene has been mutated. Such *B. anthracis* mutants are not capable of synthesizing the AI-2 molecule and show defects in cell growth.

In certain embodiments, *B. anthracis* luxS gene mutants may be produced by homologous recombination mediated mutation of the luxS gene. For example, the endogenous *B. anthracis* luxS gene may be removed, or disrupted by or replaced with heterologous sequences (e.g., sequences conferring resistance to an antibiotic). Alternatively, the endogenous *B. anthracis* luxS gene may be replaced with mutated luxS sequences that no longer encode a functional *B. anthracis* LuxS polypeptide.

In these embodiments, a nucleic acid molecule comprising elements A, B, and optionally C is introduced into a *B. anthracis* cell. Element A is comprises sequences substantially similar to a genomic region upstream of the intended mutation site, while Element B comprises of sequences substantially similar to a genomic region downstream of the intended mutation site. Element C comprises, for example, heterologous sequences or mutated luxS sequences. The sequences of Elements A and B mediate homologous recombination between the introduced nucleic acid molecule and the corresponding segments of genomic sequence. The extent of any deletion caused by this recombination event is determined by the extent of physical separation between the regions of genomic sequence represented by Elements A and B. Where Element C is present, homologous recombination will serve to insert the sequences of Element C into the genome, where this insertion is between the regions of genomic sequence represented by Elements A and B.

A number of methods are known in the art for introducing mutations within target nucleic acid sequences which may be applied to generate and identify mutant *B. anthracis* luxS nucleic acid sequences. The described techniques can be used to generate a wide variety of nucleic acid sequence alterations including point mutations, deletions, insertions, and inversions. Site-directed in vitro mutagenesis techniques include linker-insertion, nested deletion, linker-scanning, and oligonucleotide-mediated mutagenesis (as described, for example, Sambrook, et al. *Molecular Cloning: A Laboratory Manual.* 2$^{nd}$ Edition (Cold Spring Harbor Laboratory: 1989) and Ausubel, et al., eds. *Current Protocols in Molecular Biology* (John Wiley & Sons: 1989)). Error-prone polymerase chain reaction (PCR) can be used to generate libraries of mutated nucleic acid sequences Ausubel, et al., eds. *Current Protocols in Molecular Biology* (John Wiley & Sons: 1989 and Cadwell, et al. PCR Methods and Applications 1992; 2:28-33). Mutated nucleic acid sequences can also be produced according to the methods of U.S. Pat. No. 5,248,604 to Fischer. Cassette mutagenesis, in which the specific region to be altered is replaced with a synthetically mutagenized oligonucleotide, may also be used (Arkin, et al. Proc. Natl. Acad. Sci. USA 1992; 89:7811-7815; Oliphant, et al. Gene 1986; 44:177-183; and Hermes, et al. Proc. Natl. Acad. Sci. USA 1990; 87:696-700]. Alternatively, mutator strains of host cells can be employed to increase the mutation frequency of an introduced *B. anthracis* LuxS encoding nucleic acid sequence (Greener, et al. Strategies in Mol. Biol. (1995) 7:32).

Mutated *B. anthracis* luxS nucleic acid sequences which no longer encode a functional *B. anthracis* LuxS polypeptide may be identified using the *E. coli* DH5α® strain-based *V. harveyi* strain BB170 bioluminescence assay described above. Expression vectors comprising the mutated luxS sequences are expressed in *E. coli* strain DH5α® strain host cells. Expression of a mutated *B. anthracis* luxS nucleic acid sequence that no longer encodes a functional *B. anthracis* LuxS polypeptide will fail to complement the luxS gene mutation of *E. coli* strain DH5α® strain and will not restore synthesis of the AI-2 molecule. As a result, CFM prepared from cultures of such *E. coli* host cells will not induce bioluminescence in the *V. harveyi* strain BB170 bioluminescence assay.

In alternate embodiments, *B. anthracis* luxS gene mutants may be generated by direct mutagenesis of *B. anthracis* using, for example, any of the mutagens well known in the art, including (but not limited to) nitrosoguanidine, ionizing radiation, ultraviolet light, ethidium bromide, and ethyl methane sulfonate. Mutagenized bacteria are then screened for luxS gene function, for example, by using the *V. harveyi* strain BB170 bioluminescence assay. CFM prepared from cultures of *B. anthracis* luxS gene mutants will not induce bioluminescence in the *V. harveyi* bioluminescence assay. As a control for specificity (i.e., to be sure that the phenotype is due to an alteration in the luxS gene), these *B. anthracis* mutants are then transfected with expression constructs comprising nucleic acid sequences encoding a functional *B. anthracis* LuxS polypeptide. If the mutation is in the endogenous luxS gene, then the expressed LuxS polypeptide will rescue the defect such that CFM prepared from cultures of these cells will induce bioluminescence in the *V. harveyi* bioluminescence assay. If the mutation is not in the endogenous luxS gene, then the expressed LuxS polypeptide will not rescue the defect, such that CFM prepared from cultures of these cells will not induce bioluminescence in the *V. harveyi* bioluminescence assay.

The *B. anthracis* luxS gene mutants of the invention display a defect in cell growth. This defect may be observed, for example, by quantification of changes in bacterial cell density in culture over time, where the rate of change in cell density reflects the rate of cell division. Bacterial cell density may be conveniently quantitated, for example, by spectrophotometric measurement of optical density of the bacterial culture at various time points, where optical density is directly proportional to bacterial cell number. Preferably, optical density is measured at 600 nanometers transmission wavelength (OD$_{600}$). Growth curves may then be generated by plotting these OD$_{600}$ values (Y-axis) against length of time in culture (X-axis). *B. anthracis* luxS gene mutants will show a delay in the transition from the lag phase to the exponential phase of bacterial growth and/or reduced maximal levels of bacterial growth.

Inhibition of *B. Anthracis*

The present invention also provides a method for inhibiting the growth of *B. anthracis* by inhibiting the activity of a *B. anthracis* LuxS polypeptide. The effect of inhibiting the activity of a *B. anthracis* LuxS polypeptide on *B. anthracis* cell growth may be evaluated, for example, by culturing *B. anthracis* in which the activity of a *B. anthracis* LuxS polypeptide is inhibited and analyzing growth curves of such cultures as described above.

In one embodiment, the method comprises inhibiting the activity of the *B. anthracis* LuxS polypeptide by introducing anti-LuxS antibodies into a culture or host, e.g., a human, infected with the *B. anthracis* bacteria. In other embodiments, the method comprises inhibiting the activity of a *B. anthracis* LuxS polypeptide by mutating the luxS gene of *B. anthracis* (e.g., as described above). In an exemplified embodiment, the luxS gene of *B. anthracis* is mutated by replacing the LuxS encoding sequences with a *B. subtilis* aphA gene conferring kanamycin resistance.

In a specific embodiment, antibodies that agonize or antagonize the activity of a *B. anthracis* LuxS polypeptide can be generated according to the methods described above. Such antibodies can be tested using the assays described infra for identifying ligands. Monoclonal and polyclonal antibodies that antagonize the activity of a *B. anthracis* LuxS polypeptide can be introduced (e.g., by microinjection) into *B. anthracis* cells to inhibit AI-2 molecule production and cell growth of the bacteria.

AI-2 molecule production of *B. anthracis* cells that have been treated with antibodies that antagonize the activity of a *B. anthracis* LuxS polypeptide may be assessed using the *V. harveyi* strain BB170 bioluminescence assay as described above. CFM prepared from cultures of *B. anthracis* that have been treated with antibodies that antagonize the activity of a *B. anthracis* LuxS polypeptide will fail to induce luminescence in the assay.

Similarly, the effect of antibodies that antagonize the activity of a *B. anthracis* LuxS polypeptide on *B. anthracis* cell growth may be observed, for example, by quantitation of changes in bacterial cell density in culture over time, where the rate of change in cell density reflects the rate of cell division. Bacterial cell density may be conveniently quantitated, for example, by spectrophotometric measurement of optical density of the bacterial culture at various time points, where optical density is directly proportional to bacterial cell density. Preferably, optical density is measured at 600 nanometers transmission wavelength ($OD_{600}$). Growth curves may then be generated by plotting these $OD_{600}$ values (Y-axis) against length of time in culture (X-axis). Antibodies that antagonize the activity of a *B. anthracis* LuxS polypeptide will inhibit *B. anthracis* growth.

In other embodiments, the method comprises inhibiting the activity of a *B. anthracis* LuxS polypeptide by reducing the expression of the *B. anthracis* luxS gene. This inhibition may be accomplished, for example, by introduction into a *B. anthracis* cell of an antisense nucleic acid comprising a sequence that is complementary to the *B. anthracis* luxS gene.

An "antisense nucleic acid" is a single stranded nucleic acid molecule which, on hybridizing under cytoplasmic conditions with complementary bases in an RNA or DNA molecule, inhibits the latter's role (for example, by inhibiting transcription and/or translation). If the RNA is a messenger RNA transcript, the antisense nucleic acid is a counter transcript or mRNA-interfering complementary nucleic acid. As presently used, "antisense" broadly includes RNA-RNA interactions, RNA-DNA interactions, ribozymes and RNase-H mediated arrest. Antisense nucleic acid molecules can be encoded by a recombinant gene for expression in a cell (e.g., U.S. Pat. No. 5,814,500; U.S. Pat. No. 5,811,234), or alternatively they can be prepared synthetically (e.g., U.S. Pat. No. 5,780,607).

Specific non-limiting examples of synthetic antisense nucleic acids envisioned for use in accordance with this invention include, but are not limited to, antisense nucleic acids that contain phosphorothioates, phosphotriesters, methyl phosphonates, short chain alkyl, or cycloalkl intersugar linkages or short chain heteroatomic or heterocyclic intersugar linkages. Nitrogen linkers or groups containing nitrogen can also be used to prepare antisense nucleic acid mimics (U.S. Pat. No. 5,792,844 and No. 5,783,682). U.S. Pat. No. 5,637,684 describes phosphoramidate and phosphorothioamidate oligomeric compounds. Also envisioned are antisense nucleic acids having morpholino backbone structures (U.S. Pat. No. 5,034,506). In other embodiments, such as the peptide-nucleic acid (PNA) backbone, the phosphodiester backbone of the antisense nucleic acid may be replaced with a polyamide backbone, the bases being bound directly or indirectly to the aza nitrogen atoms of the polyamide backbone (Nielsen et al., Science 1991, 254:1497). Other synthetic antisense nucleic acids may contain substituted sugar moieties comprising one of the following at the 2' position: OH, SH, $SCH_3$, F, OCN, $O(CH_2)_nNH_2$ or $O(CH_2)_nCH_3$ where n is from 1 to about 10; $C_1$ to $C_{10}$ lower alkyl, substituted lower alkyl, alkaryl or aralkyl; Cl; Br; CN; $CF_3$; $OCF_3$; O-; S-, or N-alkyl; O-, S-, or N-alkenyl; $SOCH_3$; $SO_2CH_3$; $ONO_2$; $NO_2$; $N_3$; $NH_2$; heterocycloalkyl; heterocycloalkaryl; aminoalkylamino; polyalkylamino; substituted silyl; a fluorescein moiety; an RNA cleaving group; a reporter group; an intercalator; a group for improving the pharmacokinetic properties of an oligonucleotide; or a group for improving the pharmacodynamic properties of an antisense nucleic acid, and other substituents having similar properties. Antisense nucleic acids may also have sugar mimetics such as cyclobutyls or other carbocyclics in place of the pentofuranosyl group. Nucleotide units having nucleosides other than adenosine, cytidine, guanosine, thymidine and uridine, such as inosine, may be used in an antisense nucleic acid molecule.

The methods described above are also contemplated for inhibiting the activity or expression of PA in *B. anthracis*.

Furanones

The present invention also provides a method for inhibiting the growth and toxin production of *B. anthracis* by the use of furanones. In one embodiment, furanone treatment of *B. anthracis* inhibits growth by inhibiting the activity of the AI-2 quorum-sensing molecule. In another embodiment, furanone treatment of *B. anthracis* inhibits toxin production, specifically the expression of protective antigen. Furanones to be used in accordance with the present invention include (5Z)-4-bromo-5-(bromomethylene)-3-butyl-2(5H)-furanone ("furanone 1"), 3-butyl-5-(dibromomethylene)-2-(5H)-furanone ("furanone 2"), 5-(bromomethylene)-2-(5H)-furanone ("furanone 3"), 4-bromo-5-(bromomethylene)-2(5H)-furanone ("furanone 4"), and 5-(dibromomethylene)-2(5H)-furanone ("furanone 5"). The chemical structure these furanones are as follows:

(5Z)-4-bromo-5-(bromomethylene)-3-butyl-2(5H)-furanone ("furanone 1")

3-butyl-5-(dibromomethylene)-2-(5H)-furanon ("furanone 2")

5-(bromomethylene)-2-(5H)-furanone ("furanone 3")

4-bromo-5-(bromomethylene)-2(5H)-furanone ("furanone 4")

5-(dibromomethylene)-2(5H)-furanone ("furanone 5")

The furanones to be used in accordance with the present invention may be obtained from natural sources or chemically synthesized. For example, (5Z)-4-bromo-5-(bromomethylene)-3-butyl-2(5H)-furanone and 3-butyl-5-(dibromomethylene)-2-(5H)-furanone may be extracted and purified from seaweed (e.g., the marine algae *Delisea pulchra*) as previously described (see, e.g., de Nys et al. Tetrahedron 1993; 49:11213-11220). Alternatively, (5Z)-4-bromo-5-(bromomethylene)-3-butyl-2(5H)-furanone, 3-butyl-5-(dibromomethylene)-2-(5H)-furanone, 5-(bromomethylene)-2-(5H)-furanone, 4-bromo-5-(bromomethylene)-2(5H)-furanone, and/or 5-(dibromomethylene)-2(5H)-furanone may be chemically synthesized as previously described (see, e.g.: Beechan and Sims. Tetrahedron Letters 1979; 19:1649-1652; Manny et al. Tetrahedron. 1997; 53:15813-15826; and Ren, Sims and Wood. Let. Appl. Microbiol. 2002; 34-293-299).

The effect of furanone treatment on cell growth of *B. anthracis* may be evaluated, for example, by culturing *B. anthracis* cells in liquid culture media containing various concentrations of furanone. The effect of furanone on growth may then be observed, for example, by quantification of changes in bacterial cell density in culture over time, where the rate of change in cell density reflects the rate of cell division. Bacterial cell density may be conveniently quantitated, for example, by spectrophotometric measurement of optical density of the bacterial culture at various time points, where optical density is directly proportional to bacterial cell density. Preferably, optical density is measured at 600 nanometers transmission wavelength ($OD_{600}$). Growth curves may then be generated by plotting these $OD_{600}$ values (Y-axis) against length of time in culture (X-axis). *B. anthracis* cells exposed to effective concentrations furanone will show reduced levels of bacterial growth.

Methods of Treatment

The invention encompasses a method for the treatment or prevention of *B. anthracis* infection in a subject in need thereof, by administering to the subject a therapeutically effective amount of furanone and a pharmaceutically acceptable carrier.

The effect of furanone treatment on pagA expression of *B. anthracis* may be evaluated, for example, by the use of the strain RBAF140 containing pag-lacZ, the regulatory region for the pagA protective antigen gene fused to the gene coding for LacZ, inserted as a single copy at the corresponding pagA gene locus on pXO1 (Sirard, Mock, and Fouet. J. Bacteriol. 1994; 176(16):5188-92). Transcription of the pag-lacZ reporter construct in RBAF 140 can be used to assess pagA transcriptional activity under various experimental conditions by using Optical Density measurements to determine the β-galactosidase activity corresponding to pag-lacZ transcription. Likewise, the effect of various furanone treatments on PA expression may be assessed by Western blot or ELISA of *B. anthracis* total proteins.

In one embodiment of the present invention, the furanone inhibits the expression or activity of PA.

The present invention further provides methods for preventing *B. anthracis* infection in a subject, and for enhancing an immune response to *B. anthracis* infection in a subject, by administering a vaccine comprising *B. anthracis* cells containing a mutated luxS gene. In a preferred embodiment, the luxS gene of *B. anthracis* is mutated by removing the nucleotide sequence set forth in SEQ ID NO: 1 and replacing it with a nucleotide sequence conferring antibiotic resistance, such as the *B. subtilis* aphA gene.

Enhancement of an immune response in a subject can be measured by standard tests including, but not limited to, the following: direct measurement of peripheral blood lymphocytes by means known to the art; circulating antibody levels, natural killer cell cytotoxicity assays (Provinciali et al. (1992) J. Immunol. Meth. 155: 19-24), cell proliferation assays (Vollenweider et al. (1992) J. Immunol. Meth. 149: 133-135), immunoassays of immune cells and subsets (Loeffler et al. (1992) Cytom. 13: 169-174; Rivoltini et al. (1992) Can. Immunol. Immunother. 34: 241-251); and skin tests for cell mediated immunity (Chang et al. (1993) Cancer Res. 53: 1043-1050). For an excellent text on methods and analyses for measuring the strength of the immune system, see, for example, Coligan et al. (Ed.) (2000) Current Protocals in Immunology, Vol. 1, Wiley & Sons.

Formulations, Dosage, and Administration

The invention also encompasses pharmaceutical compositions and vaccines. The pharmaceutical compositions of the invention comprise a *B. anthracis* LuxS polypeptide inhibitor (e.g., an antisense nucleic acid), or a *B. anthracis* AI-2 quorum-sensing molecule inhibitor (e.g., furanone), or a PA inhibitor (e.g., furanone), and a pharmaceutically acceptable carrier. The vaccines of the invention comprise a *B. anthracis* cell in which the luxS gene is mutated and a pharmaceutically acceptable carrier. Methods of formulating pharmaceutical compositions and vaccines are well-known to those of ordinary skill in the art (see, e.g., Remington's Pharmaceutical Sciences, 18th Edition, Gennaro, ed. (Mack Publishing Company: 1990)).

Formulations. The compositions of the present invention may comprise pharmaceutically acceptable diluents, preservatives, solubilizers, emulsifiers, adjuvants and/or carriers. Such compositions include diluents of various buffer content (e.g., Tris-HCl, acetate, phosphate), pH and ionic strength; additives such as detergents and solubilizing agents (e.g., TWEEN 80, Polysorbate 80), anti-oxidants (e.g., ascorbic acid, sodium metabisulfite), preservatives (e.g., Thimersol, benzyl alcohol) and bulking substances (e.g., lactose, mannitol); incorporation of the material into particulate preparations of polymeric compounds such as polylactic acid, polyglycolic acid, etc. or into liposomes. Hylauronic acid may also be used. See, e.g., Remington's Pharmaceutical Sciences, 18th Ed. (1990, Mack Publishing Co., Easton, Pa. 18042) pages 1435-1712 which are herein incorporated by reference.

Contemplated for use herein are oral solid dosage forms, which are described generally in Remington's Pharmaceutical Sciences, 18th Ed. 1990 (Mack Publishing Co. Easton Pa. 18042) at Chapter 89, which is herein incorporated by reference. Solid dosage forms include tablets, capsules, pills, troches or lozenges, cachets, pellets, powders, or granules. Also, liposomal or proteinoid encapsulation may be used to formulate the present compositions (as, for example, proteinoid microspheres reported in U.S. Pat. No. 4,925,673). Liposomal encapsulation may be used and the liposomes may be derivatized with various polymers (e.g., U.S. Pat. No. 5,013,556). A description of possible solid dosage forms for the therapeutic is given by Marshall, K. In: *Modern Pharmaceutics* Edited by G. S. Banker and C. T. Rhodes Chapter 10, 1979, herein incorporated by reference. In general, the formulation will include the therapeutic agent and inert ingredients which allow for protection against the stomach environment, and release of the biologically active material in the intestine.

Also contemplated for use herein are liquid dosage forms for oral administration, including pharmaceutically acceptable emulsions, solutions, suspensions, and syrups, which may contain other components including inert diluents; adjuvants, wetting agents, emulsifying and suspending agents; and sweetening, flavoring, coloring, and perfuming agents.

For oral formulations, the location of release may be the stomach, the small intestine (the duodenum, the jejunem, or the ileum), or the large intestine. One skilled in the art has available formulations which will not dissolve in the stomach, yet will release the material in the duodenum or elsewhere in the intestine, e.g., by the use of an enteric coating. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit® L30D polymer, Aquateric® aqueous enteric coating, cellulose acetate phthalate (CAP), Eudragit® L polymer, Eudragit® S polymer, and Shellac. These coatings may be used as mixed films.

A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic (i.e. powder), for liquid forms a soft gelatin shell may be used. The shell material of cachets could be thick starch or other edible paper. For pills, lozenges, molded tablets or tablet triturates, moist massing techniques can be used. The formulation of the material for capsule administration could also be as a powder, lightly compressed plugs, or even as tablets. These therapeutics could be prepared by compression.

One may dilute or increase the volume of the therapeutic agent with an inert material. These diluents could include carbohydrates, especially mannitol, α-lactose, anhydrous lactose, cellulose, sucrose, modified dextrans and starch. Certain inorganic salts may be also be used as fillers including calcium triphosphate, magnesium carbonate and sodium chloride. Some commercially available diluents are Fast-Flo® lactose, Emdex® diluent, STA-Rx 1500® diluent, Emcompress® diluent and Avicell™ diluent.

Disintegrants may be included in the formulation of the therapeutic agent into a solid dosage form. Materials used as disintegrates include but are not limited to starch, including the commercial disintegrant based on starch, Explotab® disintegrant, Sodium starch glycolate, Amberlite™ disintegrant, sodium carboxymethylcellulose, ultramylopectin, sodium alginate, gelatin, orange peel, acid carboxymethyl cellulose, natural sponge and bentonite may all be used. The disintegrants may also be insoluble cationic exchange resins. Powdered gums may be used as disintegrants and as binders, and can include powdered gums such as agar, Karaya or tragacanth. Alginic acid and its sodium salt are also useful as disintegrants.

Binders may be used to hold the therapeutic agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the peptide (or derivative).

An antifrictional agent may be included in the formulation to prevent sticking during the formulation process. Lubricants may be used as a layer between the peptide (or derivative) and the die wall, and these can include but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax™ 4000 and 6000 polyethylene glycol.

Glidants that might improve the flow properties drug during formulation and to aid rearrangement during compression might be added. The glidants may include starch, talc, pyrogenic silica and hydrated silicoaluminate.

To aid dissolution of the therapeutic agent into the aqueous environment a surfactant might be added as a wetting agent. Surfactants may include anionic detergents such as sodium lauryl sulfate, dioctyl sodium sulfosuccinate and dioctyl sodium sulfonate. Cationic detergents might be used and could include benzalkonium chloride or benzethomium chloride. The list of potential nonionic detergents that could be included in the formulation as surfactants are lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the protein or derivative either alone or as a mixture in different ratios.

Controlled release oral formulations may used in practicing the present invention. The therapeutic agent could be incorporated into an inert matrix which permits release by either diffusion or leaching mechanisms, e.g., gums. Slowly degenerating matrices may also be incorporated into the formulation. Some enteric coatings also have a delayed release effect. Another form of a controlled release is by a method based on the Oros® therapeutic system (Alza Corp.), i.e. the therapeutic agent is enclosed in a semipermeable membrane which allows water to enter and push agent out through a single small opening due to osmotic effects.

Other coatings may be used for the formulation. These include a variety of sugars which could be applied in a coating pan. The therapeutic agent could also be given in a film coated tablet and the materials used in this instance are divided into 2 groups. The first are the nonenteric materials and include methyl cellulose, ethyl cellulose, hydroxyethyl cellulose, methylhydroxy-ethyl cellulose, hydroxypropyl cellulose, hydroxypropyl-methyl cellulose, sodium carboxy-methyl cellulose, providone and the polyethylene glycols. The second group consists of the enteric materials that are commonly esters of phthalic acid. A mix of materials might be used to provide the optimum film coating. Film coating may be carried out in a pan coater or in a fluidized bed or by compression coating.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants, preserving, wetting, emulsifying, and dispersing agents. The pharmaceutical compositions may be sterilized by, for example, filtration through a bacteria retaining filter, by incorporating sterilizing agents into the compositions, by irradiating the compositions, or by heating the compositions. They can also be manufactured using sterile water, or some other sterile injectable medium, immediately before use.

Vaccines. In the case of vaccines, it is often observed that a primary challenge with an antigen alone, in the absence of an adjuvant, will fail to elicit a humoral or cellular immune response. Therefore the vaccines of the invention may contain adjuvants including, but not limited to, complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions, keyhole limpet hemocyanins, and potentially useful human adjuvants such as N-acetyl-muramyl-L-threonyl-D-isoglutamine (thr-MDP), N-acetyl-nor-muramyl-L-alanyl-D-isoglutamine, N-acetylmuramyl-L-alanyl-D-isoglutaminyl-L-alanine-2-(1'-2'-dipalmitoyl-sn-glycero-3-hydroxyphosphoryloxy)-ethylamine, BCG (bacille Calmette-Guerin) and *Corynebacterium parvum*. An adjuvant can serve as a tissue depot that slowly releases the antigen and also as a lymphoid system activator that non-specifically enhances the immune response (Hood et al., *Immunology, Second Ed.,* 1984, Benjamin/Cummings: Menlo Park, Calif., p. 384). Where the vaccine is intended for use in human subjects, the adjuvant should be pharmaceutically acceptable.

Administration. Such pharmaceutical compositions or vaccines may be for administration by oral (solid or liquid), parenteral (intramuscular, intraperitoneal, intravenous (IV) or subcutaneous injection), transdermal (either passively or using iontophoresis or electroporation), transmucosal (nasal, vaginal, rectal, or sublingual), or inhalation routes of administration, or using bioerodible inserts and can be formulated in dosage forms appropriate for each route of administration.

In a preferred embodiment, the compositions or vaccines are administered by pulmonary delivery. The composition or vaccine is delivered to the lungs of a mammal while inhaling and traverses across the lung epithelial lining to the blood stream [see, e.g., Adjei, et al. Pharmaceutical Research 1990; 7:565-569; Adjei, et al. Int. J. Pharmaceutics 1990; 63:135-144 (leuprolide acetate); Braquet, et al. J. Cardiovascular Pharmacology 1989; 13 (sup5): 143-146 (endothelin-1); Hubbard, et al. (1989) Annals of Internal Medicine, Vol. III, pp. 206-212 ($\alpha$1-antitrypsin); Smith, et al. J. Clin. Invest. 1989; 84:1145-1146 ($\alpha$-1-proteinase); Oswein, et al. "Aerosolization of Proteins", 1990; Proceedings of Symposium on Respiratory Drug Delivery II Keystone, Colo. (recombinant human growth hormone); Debs, et al. J. Immunol. 1988; 140:3482-3488 (interferon-$\gamma$ and tumor necrosis factor $\alpha$); and U.S. Pat. No. 5,284,656 to Platz, et al. (granulocyte colony stimulating factor). A method and composition for pulmonary delivery of drugs for systemic effect is described in U.S. Pat. No. 5,451,569 to Wong, et al. See also U.S. Pat. No. 6,651,655 to Licalsi et al.

Contemplated for use in the practice of this invention are a wide range of mechanical devices designed for pulmonary delivery of therapeutic products, including but not limited to nebulizers, metered dose inhalers, and powder inhalers, all of which are familiar to those skilled in the art. Some specific examples of commercially available devices suitable for the practice of this invention are the Ultravent™ nebulizer (Mallinckrodt Inc., St. Louis, Mo.); the Acorn II® nebulizer (Marquest Medical Products, Englewood, Colo.); the Ventolin® metered dose inhaler (Glaxo Inc., Research Triangle Park, N.C.); and the Spinhaler® powder inhaler (Fisons Corp., Bedford, Mass.). All such devices require the use of formulations suitable for the dispensing of the therapeutic agent. Typically, each formulation is specific to the type of device employed and may involve the use of an appropriate propellant material, in addition to the usual diluents, adjuvants, surfactants and/or carriers useful in therapy. Also, the use of liposomes, microcapsules or microspheres, inclusion complexes, or other types of carriers is contemplated.

Formulations for use with a metered-dose inhaler device will generally comprise a finely divided powder containing the therapeutic agent suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant.

Formulations for dispensing from a powder inhaler device will comprise a finely divided dry powder containing the therapeutic agent, and may also include a bulking agent, such as lactose, sorbitol, sucrose, or mannitol in amounts which facilitate dispersal of the powder from the device, e.g., 50 to 90% by weight of the formulation. The therapeutic agent should most advantageously be prepared in particulate form with an average particle size of less than 10 mm (or microns), most preferably 0.5 to 5 mm, for most effective delivery to the distal lung.

Nasal or other mucosal delivery of the therapeutic agent is also contemplated. Nasal delivery allows the passage to the blood stream directly after administering the composition to the nose, without the necessity for deposition of the product in the lung. Formulations for nasal delivery include those with dextran or cyclodextran and saponin as an adjuvant.

The composition or vaccine of the present invention may be administered in conjunction with one or more additional active ingredients, pharmaceutical compositions, or vaccines. The therapeutic agents of the present invention may be administered to an animal, preferably a mammal, most preferably a human.

Dosages

Following methodologies which are well-established in the art, effective doses and toxicity of the compounds and compositions of the instant invention, which performed well in in vitro tests, are then determined in preclinical studies using small animal models (e.g., mice or rats) in which the furanones or LuxS or PA inhibitors have been found to be therapeutically effective and in which these drugs can be administered by the same route proposed for the human clinical trials.

For any pharmaceutical composition used in the methods of the invention, the therapeutically effective dose can be estimated initially from animal models to achieve a circulating plasma concentration range that includes the $IC_{50}$ (i.e., the concentration of the test compound which achieves a half-maximal inhibition of LuxS or PA activity, or which reduces the production of AI-2 by about half). Dose-response curves derived from animal systems are then used to determine testing doses for the initial clinical studies in humans. In safety determinations for each composition, the dose and frequency of administration should meet or exceed those anticipated for use in the clinical trial.

As disclosed herein, the dose of the components in the compositions of the present invention is determined to ensure that the dose administered continuously or intermittently will not exceed an amount determined after consideration of the results in test animals and the individual conditions of a patient. A specific dose naturally varies depending on the dosage procedure, the conditions of a patient or a subject animal such as age, body weight, sex, sensitivity, feed, dosage period, drugs used in combination, and seriousness of the disease. The appropriate dose and dosage times under certain conditions can be determined by the test based on the above-described indices but may be refined and ultimately decided according to the judgment of the practitioner and each patient's circumstances (age, general condition, severity of symptoms, sex, etc.) according to standard clinical techniques.

Toxicity and therapeutic efficacy of the compositions of the invention can be determined by standard pharmaceutical procedures in experimental animals, e.g., by determining the $LD_{50}$ (the dose lethal to 50% of the population) and the $ED_{50}$ (the dose therapeutically effective in 50% of the population). The dose ratio between therapeutic and toxic effects is the therapeutic index and it can be expressed as the ratio $ED_{50}/LD_{50}$. Compositions that exhibit large therapeutic indices are preferred.

The data obtained from animal studies can be used in formulating a range of doses for use in humans. The therapeutically effective doses of in humans lay preferably within a range of circulating concentrations that include the $ED_{50}$ with little or no toxicity. The dosage can vary within this range depending upon the dosage form employed and the route of administration utilized. Ideally, a single dose of each drug should be used daily.

Compounds. According to the present invention, the furanone compounds, or compounds that inhibit LuxS or PA expression or activity, will be administered to a subject in a range from about 0.5-100 mg/kg/day, preferably, from about 5.0-75.0 mg/kg/day, and more preferably, from about 10-50 mg/kg/day. For example, for administration for evaluation in a mouse model, about 50-100 µg/ml, up to about 200 ug/mouse, may be administered.

Antibodies and antisense molecules. In the embodiment of the invention where antibodies are administered (which specifically bind to e.g., LuxS or PA), typical doses are in the range from about 1-500 mg/m$^2$, depending on the binding properties of the antibody. For antisense molecules, administration is contemplated in a range from about 5-250 mg/kg/day, preferably from about 10-100 mg/kg/day, and more preferably from about 20-50 mg/kd/day.

Vaccines. The dosage of the vaccine (number of bacteria, number of administrations) will depend on route of administration and will vary according to the species to be protected. The LuxS mutant strain should be able to persist in the host for extended periods of time, usually weeks, to enhance the effectiveness of the immunizing effect by continuous stimulation of the host immune system until the host immune system has cleared all the organisms. In view of the fact that the non-virulence does not depend on any host cellular function, the strain is expected to be non-virulent even in immunodeficient hosts.

In one embodiment of the present invention where mutated B. anthracis cells are administered to a subject to treat or prevent B. anthracis, infection following exposure, the amount will be determined based e.g., on the in vitro colony forming units (CFU) of the bacterial strain infecting, or at risk of infecting, and the route of infection of the host. Alternatively, the $LD_{50}$ can be used. Published $LD_{50}$ for anthrax by the parenteral route range from less than 10 spores for a guinea pig through $3 \times 10^3$ for the rhesus monkey, $10^6$ for the rat, $10^9$ for the pig and $5 \times 10^{10}$ for the dog (Watson and Keir, 1994). Minimum infectious dose (MID) estimates are only rarely available, but an aerosol MID for sheep of 35,000 spores has been recorded (Fildes, 1943).

In one embodiment, the B. anthracis vaccine of the present invention is administered parenterally in a range from about $1 \times 10^6$ to $1 \times 10^{10}$, preferably within a range from about $1 \times 10^7$ to about $2-6 \times 10^9$ cells. In a preferred embodiment, the cells are administered parenterally, optionally in conjunction with an adjuvant, e.g., saponin.

For further guidance, see the description of non-reverting Shigella live vaccines prepared by producing auxotrophic mutants of a pathogenic strain are disclosed in U.S. Pat. No. 5,077,044. In addition, live vaccines using mutant non-pathogenic strains of E. coli have also been disclosed. See U.S. Pat. No. 4,404,186. A temperature sensitive mutant E. coli produced using a chemical mutagen has been administered intravenously and orally (PCT WO 92/12732)

EXAMPLES

The present invention is next described by means of the following examples. However, the use of these and other examples anywhere in the specification is illustrative only, and in no way limits the scope and meaning of the invention or of any exemplified form. Likewise, the invention is not limited to any particular preferred embodiments described herein. Indeed, many modifications and variations of the invention may be apparent to those skilled in the art upon reading this specification, and can be made without departing from its spirit and scope. The invention is therefore to be

Example 1

Identification, Organization, and Characterization of a Putative B. anthracis luxS Gene

Results

The unfinished genomic sequence of the Ames strain of *B. anthracis* has been made publicly available, and partially annotated, by The Institute for Genomic Research (www.TIGR.org). Using the 471-bp *B. subtilis* luxS gene sequence (via Genbank Accession # CAB 15045.1; SEQ ID NO: 20, FIG. 15) as a template, the partially annotated *B. anthracis* genome was subjected to BLASTN search under standard parameters using the search interface and algorithm available at tigrblast.tigr.org/ufmg/. This search identified a 474-bp predicted open reading frame (ORF), BA5464, with 72% sequence identity to luxS (also known as ytjB) from *B. subtilis* (see FIG. 3). The nucleotide sequence of this putative *B. anthracis* luxS gene (SEQ ID NO: 1) is depicted in FIG. 1. The transcriptional orientations of the flanking predicted ORFs BA5465 and BA5463 indicate that BA5464 is in a monocistronic operon (FIG. 3).

To further characterize the putative *B. anthracis* luxS gene, flanking genomic nucleotide sequences were submitted for BLASTN analysis versus the *B. subtilis* genomic sequence using the same interface. The genomic region upstream of the *B. anthracis* luxS ortholog showed a high level of conservation with the genomic region upstream of the putative *B. anthracis* luxS gene: the *B. subtilis* genes ytjA and ytiB were 70% and 67% identical, respectively, to the nucleotide sequences of *B. subtilis* predicted ORFs BA5465 and BA5466 (FIG. 3). The genomic region downstream of the putative *B. anthracis* luxS gene showed substantial variation compared to the genomic region downstream of the *B. subtilis* luxS gene. Only one proximate downstream *B. subtilis* gene, ytkD, had a homolog in *B. anthracis*: the *B. subtilis* ytkD gene is 65% identical to *B. anthracis* predicted ORF BA5461 (FIG. 3). Immediately downstream of *B. anthracis* BA5464 are two predicted ORFs (BA5462 and BA5463) of 258- and 231-bp, respectively, which show no significant homologies to sequences listed in the Genbank database, as determined by BLAST search. Further downstream of BA5464, two other predicted ORFs (HP-A and HP-B) that had not been identified in the TIGR partial annotation were detected. By BLAST search, HP-A was identified as having homology to a hypothetical protein in *O. iheyensis* (p-value=$10^{-17}$), however no significant homology to any Genbank deposited sequence was detected for HP-B. The distal downstream predicted ORF BA5459 was found to have strong homology to a hydrolase in *O. iheyensis* (FIG. 3).

Figure 4:
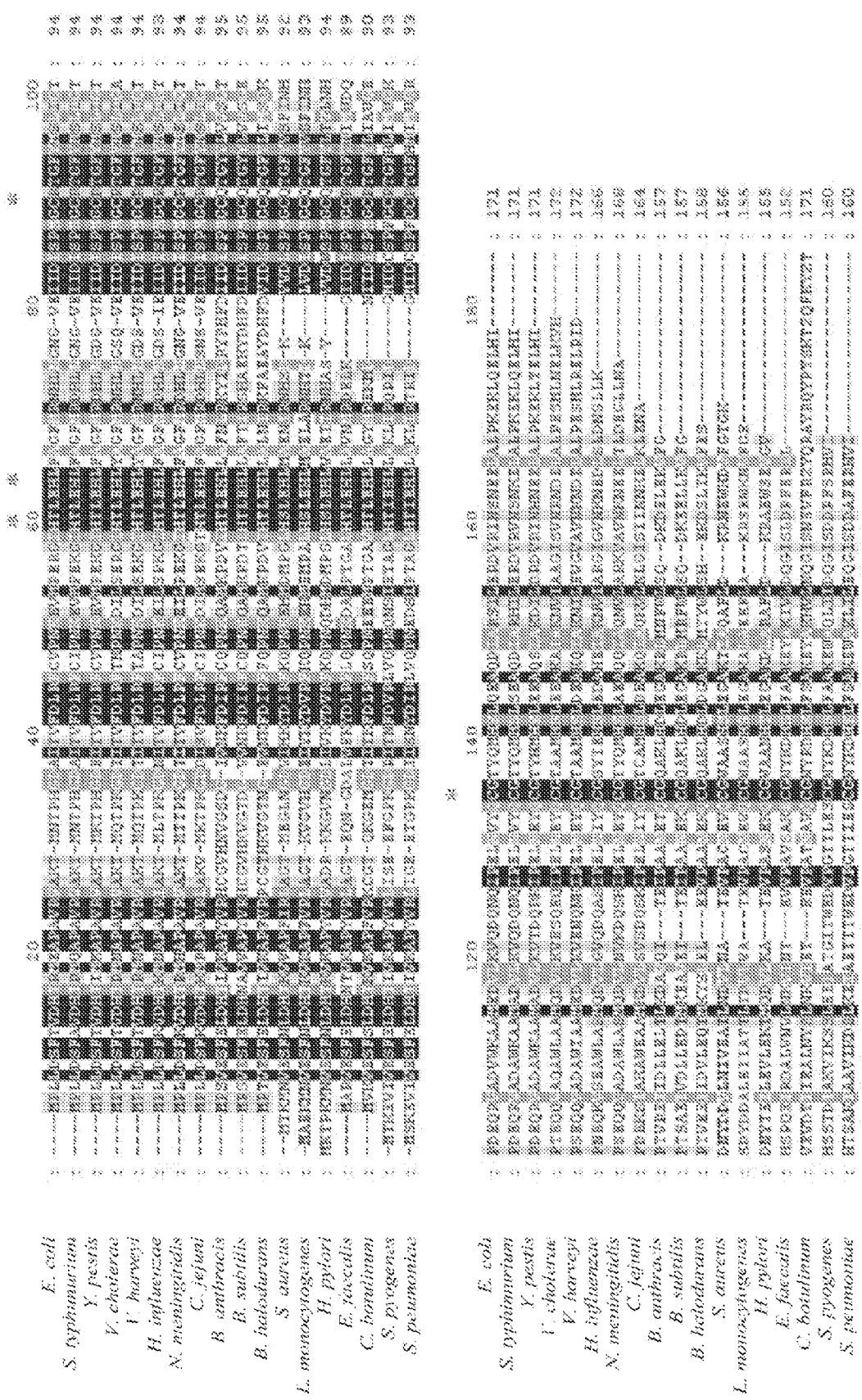
FIG. 4 is an alignment of the amino acid sequence of 17 bacterial LuxS polypeptides with the predicted translated amino acid sequence of *B. anthracis* ORF BA5464 (SEQ ID NO: 2). The 17 bacterial LuxS polypeptides that are shown are: *E. coli* (SEQ ID NO: 3), *S. typhimurium* (SEQ ID NO: 19), *Y. pestis* (SEQ ID NO: 6), *V. cholerae* (SEQ ID NO: 5), *V. harveyi* (SEQ ID NO: 4), *H. influenzae* (SEQ ID NO: 7), *N. meningitidis* (SEQ ID NO: 8), *C. jejuni* (SEQ ID NO: 9), *B. subtilis* (SEQ ID NO: 13), *B. halodurans* (SEQ ID NO: 14), *S. aureus* (SEQ ID NO: 11), *L. monocytogenes* (SEQ ID NO: 15), *H. pylori* (SEQ ID NO: 12), *E. faecalis* (SEQ ID NO: 10), *C. botulinum* (SEQ ID NO: 16), *S. pyogenes* (SEQ ID NO: 17), and *S. peumoniae* (SEQ ID NO: 18). Amino acid residues are indicated by standard one letter abbreviation. Black shading indicates amino acids that are conserved in all (18 of 18) sequences (100% conservation across bacterial species), dark grey shading indicates amino acids conserved in ≧14 of 18 sequences (≧77% conservation across bacterial species), and light grey shading indicates amino acids conserved ≧11 of 18 sequences (≧61% conservation across bacterial species). Asterisks denote residues predicted to be involved in LuxS enzymatic activity (Hilgers and Ludwig. Proc. Natl. Acad. Sci. USA. 2001; 98:11169-11174).

An alignment of the predicted translated sequence of *B. anthracis* predicted ORF BA5464 with the amino acid sequence of LuxS polypeptide amino acid sequences from 17 other bacteria, suggests that BA5464 encodes a functional LuxS polypeptide (FIG. 4). This alignment was generated from LuxS protein sequences retrieved from the N.C.B.I. and T.I.G.R. databases using the ClustalW algorithm (Thompson, Higgins and Gibson. Nucleic Acids Res. 1994; 22:4673-4680) available, for example, at www.ebi.ac.uk/clustalw/. Although size variation exists between the LuxS polypeptides, conserved regions essential for function across prokaryotic genera have been defined (Miller and Bassler. Annu. Rev. Microbiol. 2001; 55:165-169). Alignment of protein sequences from 17 known bacterial LuxS polypeptides with the predicted amino acid sequence of ORF BA5464 reveals a number of conserved amino acids, including those hypothesized to be essential for LuxS enzymatic activity (Hilgers and Ludwig. Proc. Natl. Acad. Sci. USA. 2001; 98:11169-11174). Conservation of the amino acid residues thought to be essential for enzymatic activity of LuxS suggests that *B. anthracis* ORF BA6454 encodes a functional LuxS polypeptide with function.

The aligned LuxS polypeptides are from *E. coli* (Genbank Accession # BAB36972.1; SEQ ID NO: 3), *V. harveyi* (Genbank Accession # Q9Z5X1; SEQ ID NO: 4), *V. cholerae* (Genbank Accession # AAF93725.1; SEQ ID NO: 5), *Y. pestis* (Genbank Accession # CAC92532.1; SEQ ID NO: 6), *H. influenzae* (Genbank Accession # AAC22149.1; SEQ ID NO: 7), *N. meningitidis* (Genbank Accession # CAB83759.1; SEQ ID NO: 8), *C. jejuni* (Genbank Accession # CAB73452.1; SEQ ID NO: 9), *E. faecalis* (T.I.G.R. Accession # EF1182; SEQ ID NO: 10), *S. aureus* (Genbank Accession # 13701928; SEQ ID NO: 11), *H. pylori* (Genbank Accession # AAD07175.1; SEQ ID NO: 12), *B. anthracis* (SEQ ID NO: 2), *B. subtilis* (Genbank Accession # CAB15045.1; SEQ ID NO: 13), *B. halodurans* (Genbank Accession # BAB07072.1; SEQ ID NO: 14), *L. monocytogenes* (Genbank Accession # CAC99366.1; SEQ ID NO: 15), *C. botulinum* (SEQ ID NO: 16), *S. pyogenes* (Genbank Accession # AAK34410.1; SEQ ID NO: 17), *S. pneumoniae* (Genbank Accession # AAK99112.1 SEQ ID NO: 18), and *S. typhimurium* (Genbank Accession # AAL21702.1; SEQ ID NO: 19).

Discussion

These results show that a predicted open reading frame (ORF BA5464) in the partially annotated *B. anthracis* genome possesses extensive homology to the luxS gene (ytjB) of *B. subtilis*. The orientations of other predicted ORFs flanking BA5464 indicate that BA5464 is in a monocistronic operon, which facilitates examination of its function and regulation. In other organisms, the luxS gene appears to be essential for the synthesis of the quorum-sensing molecule AI-2, first identified in the marine bacterium *Vibrio* harveyi (Bassler, Wright and Silverman. Mol. Microbiol. 1994; 13:273-286). Alignment of the amino acid sequences of known LuxS polypeptides (FIG. 4) with that predicted for *B. anthracis* ORF BA5464 confirmed the conservation of amino acids thought to be crucial to LuxS polypeptide function, suggesting that BA5464 encodes a functional luxS gene.

Example 2

Bacterial Strains and Culture Conditions

The bacterial strains used throughout the subsequent examples are summarized in Table 1.

*B. anthracis* vaccine strain 34F$_2$ (Colorado Serum Company, Denver, Colo.), a derivative of the Sterne strain (Stern, Robinson and Nicol. J. Vet. Sci. An. Ind. 1939; 12:279-302), was routinely grown at 37° C. with aeration in Brain Heart Infusion (BHI) broth (BHI powder is available from Becton Dickinson and reconsituted in water as per the manufacturer's instructions). In some cases, *B. anthracis* strains were plated and cultured on solid BHI media supplemented with bactoagar (BHI broth plus 15 g bactoagar per liter).

*V. harveyi* strain BB170 (Bassler, Wright and Silverman. Mol. Microbiol. 1994; 13:273-286), (Kindly provided by Bonnie Bassler from Princeton University; also available from Quorex, Inc.), was routinely grown at 30° C. with aeration in Auto-inducer Bioassay medium (AB). The AB medium was made as previously described (Greenberg, Hastings and Ulitzur. Arch. Microbiol. 1979; 120:87-91). For AB medium: (1) add 17.53 g sodium chloride, 6.02 g magnesium chloride, and 2 g casamino acids (vitamin free) to 960 mL of water; (2) adjust the pH to 7.5 with KOH; (3) autoclave at 121° C. for 15 minutes then cool to room temperature; and (4) aseptically add 10 mL of 1M potassium phosphate (pH7), 10 mL of 0.1M L-arginine, and 20 mL of 50% glycerol.

E. coli strains DH5α® strain (Promega) and SCS110 (Stratagene) were routinely grown at 37° C. with aeration in Luria-Bertani broth (LB: 10 g bacto-tryptone (Difco), 5 g yeast extract (Difco), and 5 g NaCl). Ampicillin (50 μg/ml) was added to LB broth in cases for selection of E. coli strains harboring recombinant plasmids.

TABLE 1

Bacterial strains used in this study

| Strain | Relevant characteristics | Source |
|---|---|---|
| E. coli DH5α ® strain | F-,080dlacZDM15, D(lacZYA-argF)U169, deoR, recA1 endA1, hsdR17(rk−, mk+), phoA, supE44, 1-, thi-1, gyrA96, relA1 | Promega |
| E. coli SCS110 | rpsL (Str$^R$) thr leu thi-1 lacY galK galT ara tonA tsx dam dcm sup44 D(lac-proAB) [F' traD36 proAB lacIqZDM15] | Stratagene |
| B. anthracis 34F$_2$ | pXO1$^+$/pXO2$^-$ | Colorado Serum Co. |
| V. harveyi BB170 | Sensor AI-1$^-$/Sensor AI-2$^+$ | Quorex, Inc. |

Example 3

Synthesis of a Functional AI-2 Molecule by B. anthracis Cells

Materials and Methods

Generation of cell-free culture medium. B. anthracis strain 34F$_2$ cells were grown in BHI broth overnight with aeration at 37° C. V. harveyi strain BB170 cells were grown in AB medium overnight with aeration at 30° C. Cell-free conditioned culture medium (CFM) was prepared from aliquots of each culture at various time points by centrifuging the cultures at 8000×g for 5 min, and passing the supernatant through a 0.2 μm pore-size Acrodisc syringe filter (Gelman Laboratory). CFM preparations were stored at −20° C. until studied.

V. harveyi bioluminescence assays. V. harveyi bioluminescence assays were performed essentially as previously described (Surette and Bassler. Proc. Natl. Acad. Sci. USA 1998; 95:7046-7050). Briefly, V. harveyi strain BB170 was grown at 30° C. in AB medium with aeration for 16 h, cultures were diluted 1:10,000 in fresh AB broth, and then CFM from the bacterial cells to be tested was added to the culture (10% by volume CFM final concentration IN culture). Aliquots of 1.0 ml were taken 2 and 4 hours after CFM was added, and bioluminescence measured using a luminometer (Lumat® LB9507 from EG&G Berthold).

Cell density of the V. harveyi BB170 reporter culture used in the assay was measured by diluting the same aliquots of cells used for measuring luminescence, spreading the dilutions onto solid Luria-Marine medium (10 g tryptone, 5 g yeast extract, and 20 g sodium chloride per liter in water), incubating the plates overnight at 30° C., and counting the resulting colonies the next day. Luminescence values were then expressed as relative light units (RLU), where RLU was calculated by dividing absolute light units by V. harveyi cell density. Experiments were performed in triplicate, and the mean (±standard deviation, SD) RLU calculated for each CFM sample at each time point.

Results and Discussion

Utilizing the V. harveyi AI-2 reporter assay, liquid cultures of B. anthracis vaccine (Sterne) strain 34F$_2$ were examined to determine whether B. anthracis cells synthesize an AI-2 or AI-2-like molecule. For wildtype V. harveyi cells, exposure to AI-1 or AI-2 can induce expression of the bioluminescence-generating luxCDABE operon. The AI-2 assay is based upon a deficiency in the AI-1 sensor pathway in the mutant V. harveyi strain BB170 (Bassler et al. Mol. Microbiol. 1993; 9:773-786), which lacks a functional luxN gene. Without the luxN encoded AI-1 sensor, strain BB170 can only exhibit bioluminescence in response to AI-2 or an AI-2-like molecule. In the assay, cell free medium (CFM) obtained from AI-2-synthesizing bacteria grown to high density (including the V. harveyi strain BB170, in which the AI-2-regulated system is intact) induces expression of the bioluminescence-generating luxCDABE operon in V. harveyi strain BB170.

Growing a culture of V. harveyi strain BB170 overnight, then diluting 1:10,000 (to yield low cell density), reduces the level of endogenous AI-2 below the threshold required to activate luminescence. In this experimental system, the addition of exogenous AI-2 from bacteria possessing luxS gene function can restore the bioluminescence phenotype of the BB170 cells (see, e.g., Surette and Bassler, supra).

Figure 5:
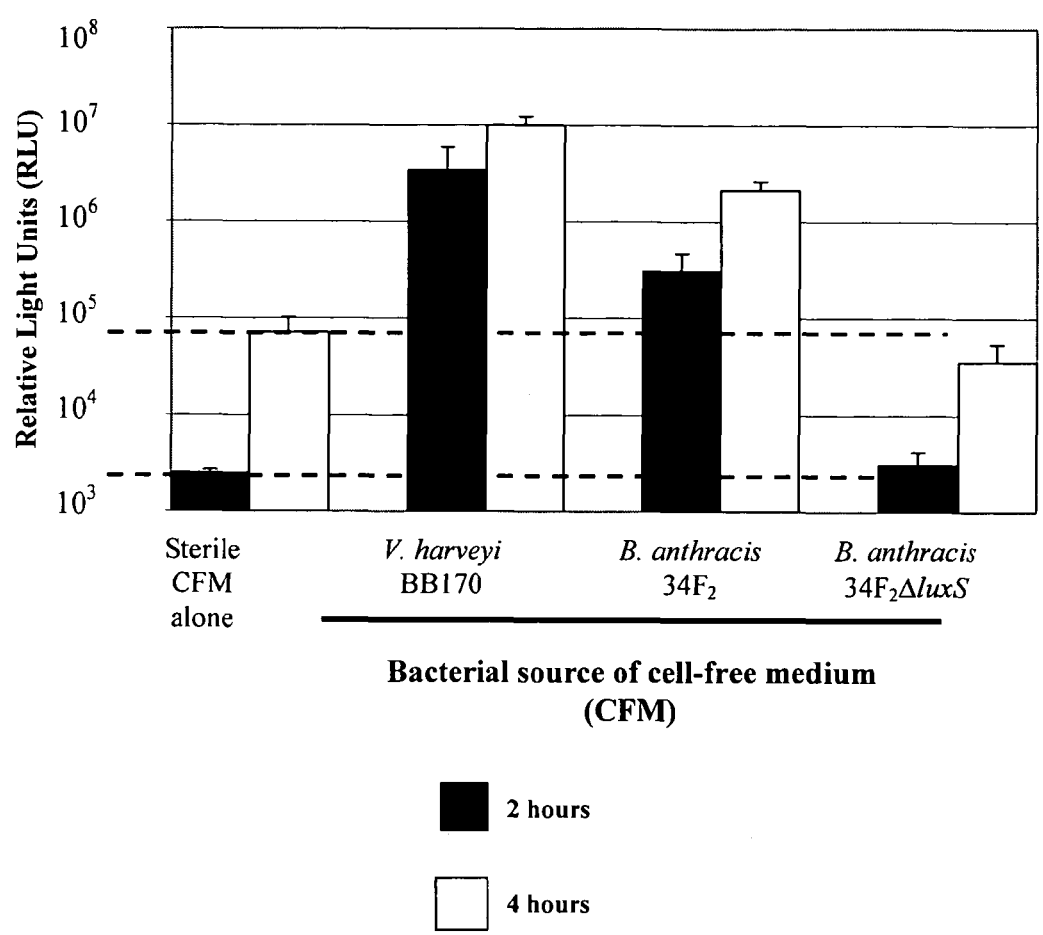
FIG. 5 depicts induction of bioluminescence in *V. harveyi* reporter strain BB170 by cell free medium (CFM) from *B. anthracis* culture. Each bar represents the mean (plus or minus the standard deviation) of triplicate experiments.

In this assay, the V. harveyi reporter strain BB170 was incubated for 2 (black boxes) or 4 (white boxes) hours with sterile cell-free medium (CFM) prepared from the indicated bacterial cultures, and Relative Light Units (RLU) of reporter strain bioluminescence was quantitated (FIG. 5). The dashed lines indicate the endogenous RLU observed for the negative control ("Sterile CFM alone") 2- and 4-hour cultures. Sterile cell-free medium (CFM) alone (i.e., medium that had not been exposed to bacterial cells) served as the negative control. The amount of luminescence observed (in RLU) upon addition of sterile CFM indicates the baseline level of in luminescence caused by production of AI-2 by the reporter strain bacteria. By 4 hours, the endogenous AI-2 activity in V. harveyi reporter strain BB170 culture was substantially higher than at 2 hours (FIG. 5, "Sterile CFM alone"). CFM from a high-density culture of V. harveyi strain BB170 served as the positive control. As expected, addition of CFM from the high-density BB170 culture induced greater than 100-fold increases in luminescence.

In multiple experiments, CFM from B. anthracis strain 34F$_2$ had similar activity to the positive control, with substantial increases in luminescence compared to the negative control (FIG. 5). The results of these experiments indicate that *B. anthracis* synthesizes AI-2 or an AI-2-like molecule that is involved in the lux quorum-sensing system.

Example 4

*B. anthracis* Predicted ORF BA5464 Encodes a Functional LuxS Protein

Materials and Methods

Construction of pMJ501. Chromosomal DNA of *B. anthracis* strain 34F$_2$ was purified using the Wizard® Genomic DNA Purification Kit according to manufacturer's instructions (Promega, Madison, Wis.). Purified genomic DNA was then used as template for PCR amplification of ORF BA5464. The PCR primers used were designated BAluxSF1 (5'-ATG CCA TCA GTA GAA AGC TTT G-3'; SEQ ID NO: 21) and BAluxSR2 (5'-CCA AAT ACT TTC TCA AGT TCA TC-3'; SEQ ID NO: 22). PCR was performed under standard conditions using the following cycling parameters: 30 cycles of denaturation for 1 min at 94° C., annealing for 1 min at 51° C., and extension for 1 min at 72° C. In the normal course of this reaction, the Taq polymerase adds single adenine nucleotides to the 3' ends of the PCR product, to generate 1 nucleotide 3' overhangs.

This amplified PCR product was ligated with linear pGEM®-T Easy vector as per manufacturer's instructions (Promega) to produce pMJ501. pGEM®-T easy vector is a linear vector with single nucleotide 3' thymine overhangs, enabling ligation to the amplified product without the need for restriction sites.

Plasmid DNA was transfected into *E. coli* strain DH5α® strain, and transfected bacteria selected by ampicillin resistance. pMJ501 plasmid DNA was purified from ampicillin-resistant transfected bacteria, and subjected to sequence analysis using vector primers T7F and SP6R to ensure that no nucleotide errors had been introduced in the cloning process.

Expression of ORF BA5464 in *E. coli* DH5α® strain *E. coli* DH5α® strain cells transfected with pMJ501, or with empty pGEM-T Easy vector. Transfected bacteria were cultured at 37° C. with aeration in LB broth plus 50 µg/ml ampicillin for approximately 2-2.5 hours to (mid-log phase, OD$_{600}$≈0.6) in either the presence or absence of 0.5 mM IPTG.

Cell free medium (CFM) was then prepared from each culture, and the *V. harveyi* bioluminescence assay performed, as described in Example 3 supra. In such assays, the following served as negative controls: incubation of the reporter strain BB170 with sterile CFM alone (i.e., CFM never exposed to bacteria), with CFM from high density IPTG-induced cell cultures of *E. coli* strain DH5α® strain without vector, or with CFM from high density IPTG-induced cell cultures of *E. coli* strain DH5α® strain containing pGEM-T with no insert. Incubation of the reporter strain BB170 with CFM from high-density cultures of *V. harveyi* strain BB170 or *B. anthracis* strain 34F$_2$ served as positive controls.

Results and Discussion

To determine whether *B. anthracis* ORF BA5464 encodes a functional LuxS polypeptide that can direct synthesis of AI-2 or an AI-2-like molecule, we took advantage of the inability of *E. coli* strain DH5α® strain to synthesize a functional AI-2 molecule. This commonly used laboratory strain of *E. coli* fails to produce measurable amounts of AI-2 due to a frameshift mutation in the 3' portion of the luxS open reading frame (Surrette, Miller and Bassler. Proc. Natl. Acad. Sci. USA 1999; 96: 1639-1644).

Figure 6:
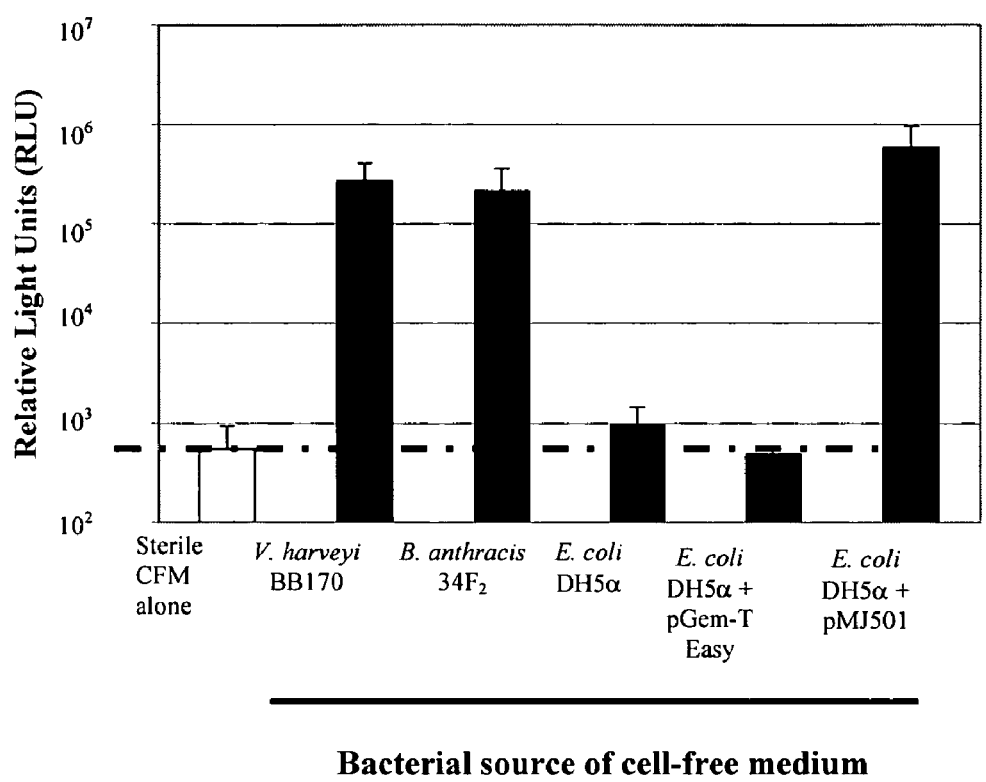
FIG. 6 depicts induction of bioluminescence in *V. harveyi* reporter strain BB170 by cell free medium (CFM) from a culture of *E. coli* expressing the *B. anthracis* ORF BA5464. The dashed line indicates the endogenous RLU observed for the negative control ("Sterile CFM alone") cultures.

The *B. anthracis* luxS ORF BA5464 was amplified by PCR and cloned into the *E. coli* shuttle vector pGEM®-T Easy vector to create pMJ501, in which expression of ORF BA5464 is under the control of an IPTG-inducible promoter. Cell free medium was prepared from high-density cultures of DH5α® strain containing vector pMJ501 that had been induced with IPTG. The prepared CFM was then screened for the presence of synthesized of AI-2 using the *V. harveyi* bioluminescence assay (FIG. 6). As previously shown, compared to baseline luminescence seen with sterile CFM alone, CFM from high-density cultures of strain BB170 and *B. anthracis* 34F$_2$ induced substantial bioluminescence (FIG. 6). As expected, no bioluminescence was induced by CFM from cultures of DH5α® strain, or from DH5α® strain containing pGEM-T Easy without an insert. In contrast, CFM from DH5α® strain containing pMJ501 induced a high level of bioluminescence, greater than that induced by CFM from the positive controls. Compared to the control *E. coli* DH5α® strain CFMs, there was a 300-fold to a 1000-fold mean increase in induction of bioluminescence by pMJ501. This result confirms that expression of *B. anthracis* ORF BA5464 can complement the *E. coli* DH5α® strain luxS mutation and restore synthesis of AI-2, indicating that ORF BA5464 encodes a functional *B. anthracis* LuxS polypeptide.

Example 5

Construction of *B. anthracis* 34F$_2$ΔluxS Strain

A *B. anthracis* strain in which the luxS gene is mutated was constructed as follows (see FIG. 7):

Chromosomal DNA of *B. anthracis* strain 34F$_2$ was purified using the Wizard® Genomic DNA Purification Kit according to manufacturer's instructions (Promega, Madison, Wis.). Purified genomic DNA was then used as template for PCR amplification of 1.18-kb and 989-bp genomic DNA fragments flanking the *B. anthracis* luxS gene (see FIG. 7A). The 1.18 kb downstream fragment (F1/R1) was amplified using primers BAluxSKOF1 (5'-GAC TCA GTA ACA GAA CGT CGG-3'; SEQ ID NO: 23) and BAluxSKOR1 (5'-CGC AAT CTC TTA CAT AAG GTG-3'; SEQ ID NO: 24). The 989 bp upstream fragment (F2/R2) was amplified using primers BAluxSKOF2 (5'-CAC ATG TGG TCA AGC GAA G-3'; SEQ ID NO: 25), and BAluxSKOR2 (5'-GCC ACA TCA TAT CCA GTA TTC G-3'; SEQ ID NO: 26). PCR was performed under standard conditions using the following cycling parameters: 30 cycles of denaturation for 1 min at 94° C., annealing for 1 min at 52° C., and extension for 1 min 30 sec at 72° C. for 30 cycles.

The PCR products were purified using a Qiagen® PCR purification kit according to manufacturer's instructions (Qiagen). The purified fragments were then digested with HindIII, to generate fragments with a HindIII half site on one end and a 3' adenine overhand on the other end (the adenine was introduced as a natural consequence of Taq polymerase activity). The two HindIII digested PCR fragments were then ligated to the linear pGEM®-T vector, which contains 5' thymine overhangs.

Figure 7A:
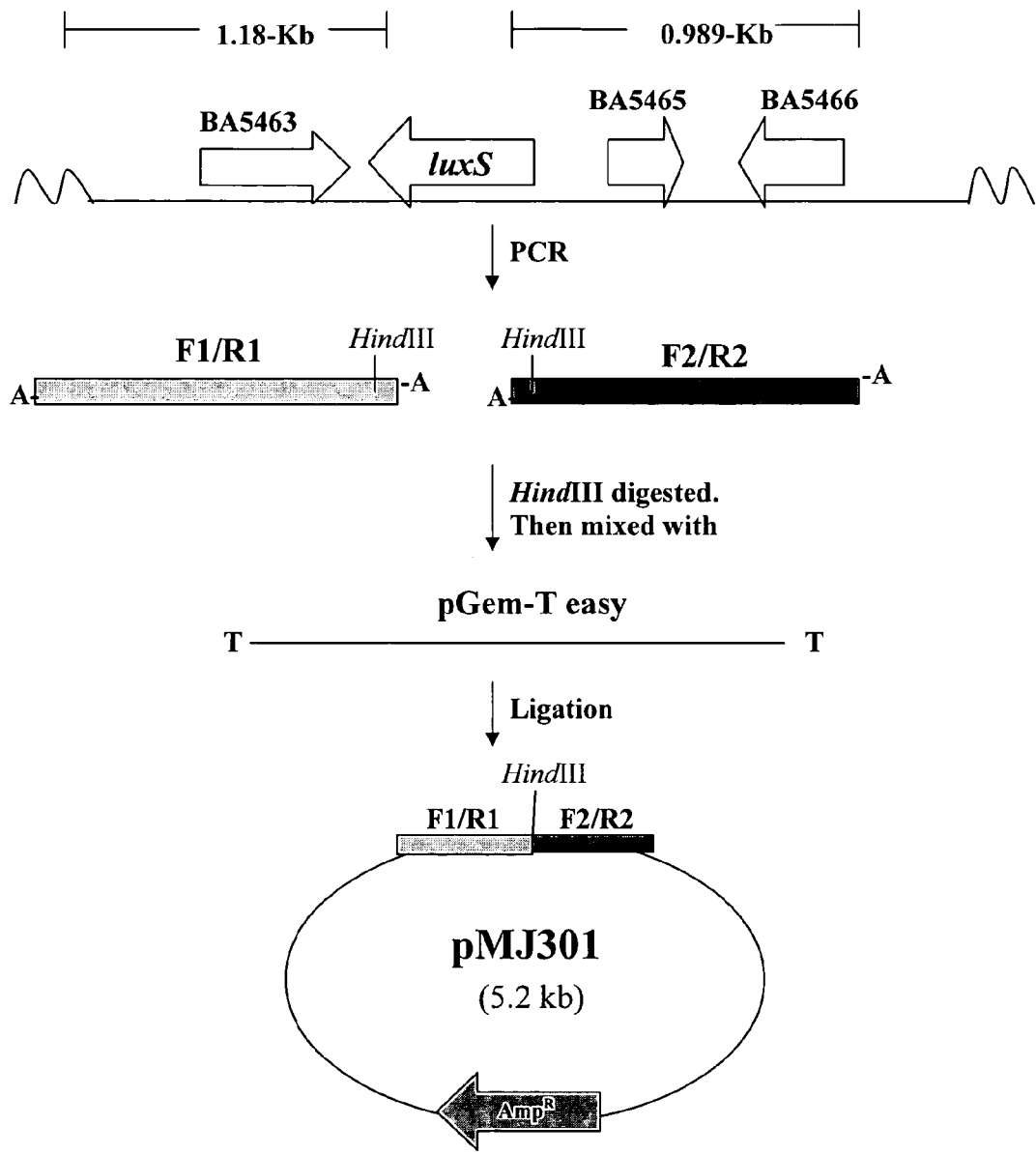
FIG. 7 depicts the assembly of the pMJ301KS construct used to generate *B. anthracis* strain 34F$_2$ΔluxS. A. Assembly of the pMJ301 construct. B. Assembly of the pMJ301K construct from pMJ301. C. Assembly of the MJ301KS construct from mMJ301K.

PCR using primers BAluxSKOF1 (SEQ ID NO: 23) and BAluxSKOR2 (SEQ ID NO: 26) was used to identify a plasmid with an ~2.1 kb insert in which the constituent fragments were joined in the proper orientation. PCR was performed using standard conditions and the following cycling parameters: 30 cycles of denaturation for 1 min at 94° C., annealing for 1 min at 52° C., and extension for 2 min 30 sec at 72° C. This plasmid is designated pMJ301 (FIG. 7A).

Figure 7B:
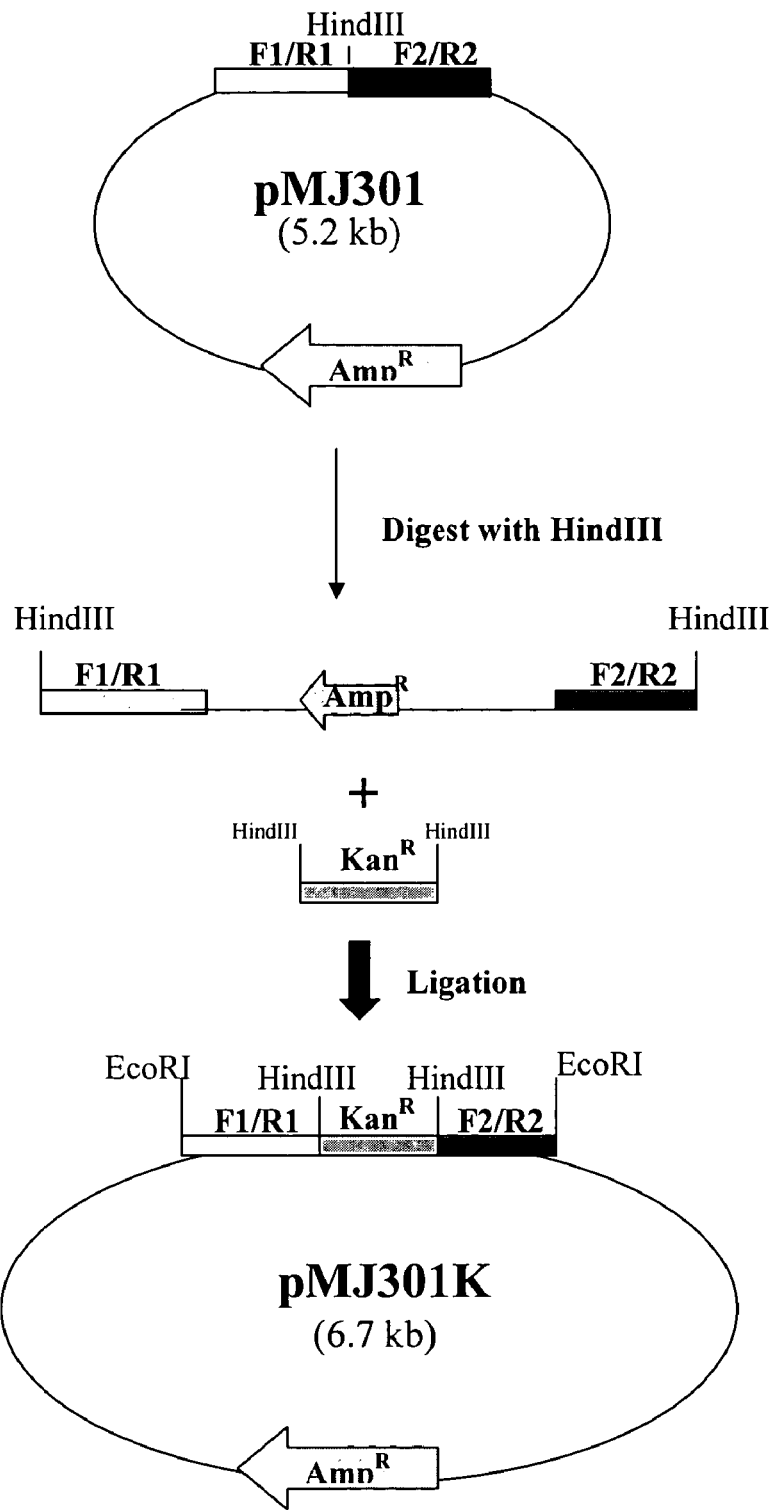
Figure 7C:
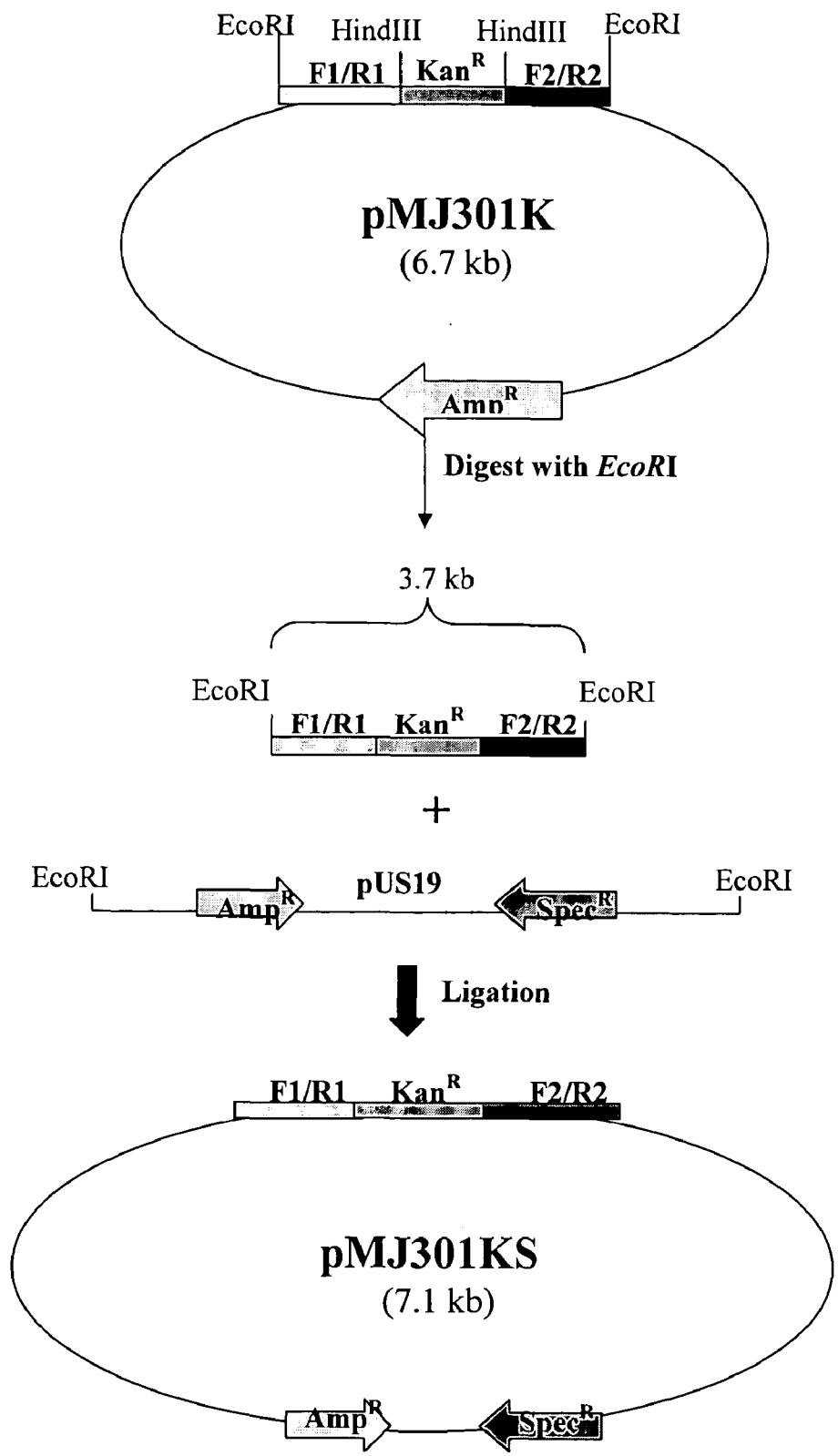

Plasmid pMJ301 was digested with HindIII (FIG. 7B). Then aphA, a *B. subtilis* derived gene that confers kanamycin-resistance (Guerot-Fleury et al. Gene. 1995; 167:335-336), was cloned into the HindIII site of pMJ301, to create pMJ301K. The aphA sequences (Genbank # V01547) were isolated by HindIII digestion of plasmid pDG780 (available from the B. Genetic Stock Center, Ohio State University).

pMJ301K was digested with EcoRI, releasing the insert region, which was cloned into EcoRI digested pUS19 vector (FIG. 7C). pUS19 is a pUC19 (New England Biolabs) derivative with a spectinomycin-resistance cassette (available from the B. Genetic Stock Center, Ohio State University). This plasmid was designated pMJ301KS. Since methylation inhibits transfection into *B. anthracis*, pMJ301KS was cloned into dam⁻ *E. coli* strain SCS110 (Stratagene).

Purified pMJ301KS from SCS110 was electroporated into *B. anthracis* strain $34F_2$. The transfected bacteria were then plated onto solid BHI medium containing 50 µg/ml of kanamycin and 100 µg/ml of spectinomycin and cultured overnight at 37° C. The resultant $Kan^R$ and $Spec^R$ colonies were cultured overday at 37° with aeration in BHI medium 50 µg/ml of kanamycin, and then subcultured daily for 15 days. After 15 days of subculture, individual bacterial colonies were screened to identify clones that were $Kan^R$ but $Spec^S$. These $Kan^R$ and $Spec^S$ bacteria were intended to represent those in which the *B. anthracis* genomic sequences of pMJ301KS had facilitated homologous recombination to remove the ORF BA5464 sequences and replace them with the aphA sequences. Such bacteria are referred to as *B. anthracis* $34F_2\Delta luxS$.

Figure 8:
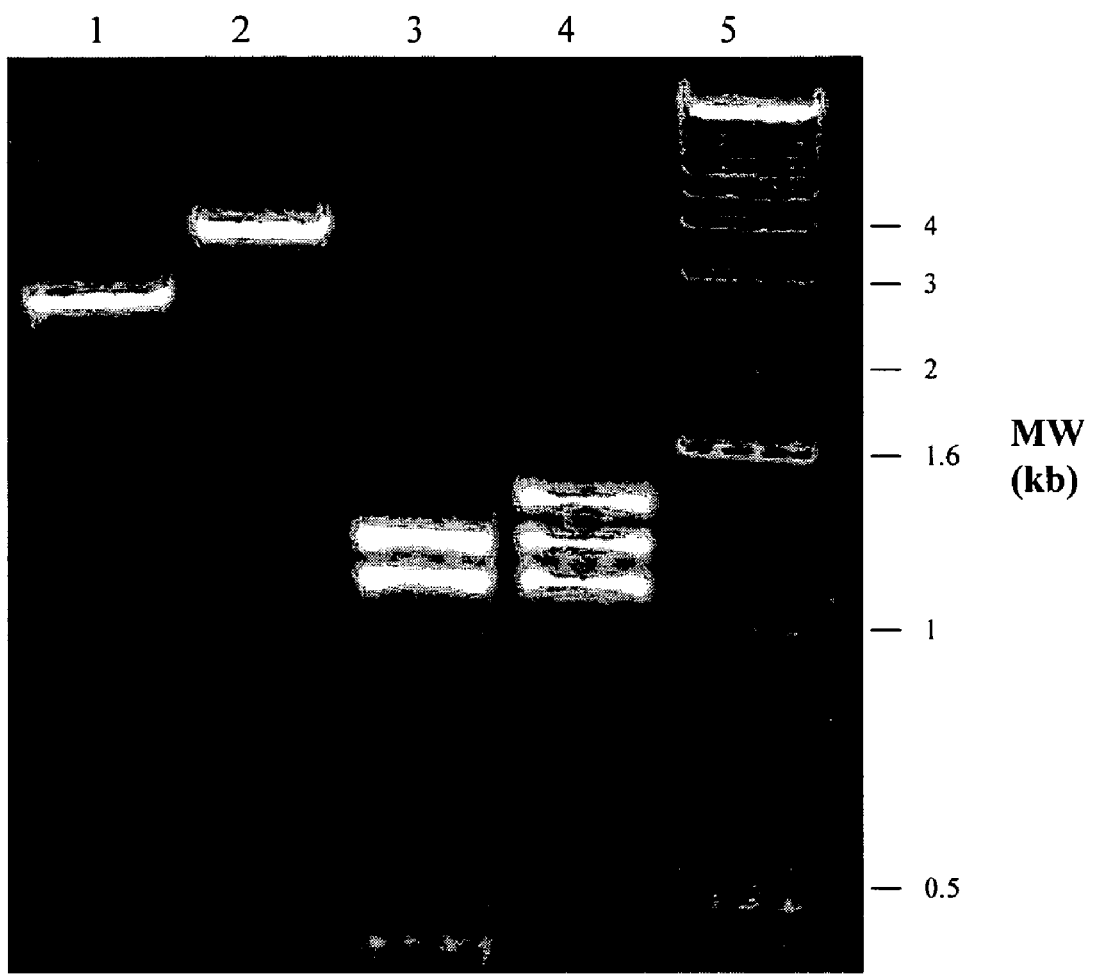
FIG. 8 depicts confirmation of the creation of *B. anthracis* 34F$_2$ΔluxS by PCR on bacterial genomic DNA. Lane 1=PCR product from wild-type strain 34F$_2$. Lane 2=PCR product from a 34F$_2$ΔluxS strain. Lane 3=PCR product from wild-type strain 34F$_2$ digested with HindIII. Lane 4=PCR product from a 34F$_2$ΔluxS strain 34F$_2$ digested with HindIII. Lane 5=molecular weight markers (1 kb ladder from Promega, Madison, Wis.) of the indicated size.

Allelic exchange of aphA for ORF BA5464 at the luxS locus was confirmed in bacterial clones with the correct antibiotic phenotype by PCR using primers that flank the region of recombination. Primers SterneF (5'-GCA AAT TGA AAA CGA CTC AG-3'; SEQ ID NO: 27) and SterneR (5'-GTA TGC TTA TAA ACA TTC CGT CG-3'; SEQ ID NO: 28) were used to PCR amplify genomic DNA from wild-type *B. anthracis* strain $34F_2$ and putative $34F_2\Delta luxS$ strains (FIG. 8). In some cases, the PCR products were purified and digested with HindIII. Wildtype bacteria show the expected size band (FIG. 8, Lane 1). $34F_2\Delta luxS$ bacteria show a larger band due to the replacement of the ~500 bp ORF BA5464 with the ~1.4 kb aphA sequence (Lane 2). Upon HindIII digestion of purified PCR product, wildtype bacteria show the expected bands (Lane 3). Upon HindIII digestion of purified PCR product, $34F_2\Delta luxS$ bacteria show an additional ~1.4 kb band, representing the inserted aphA sequences (Lane 4).

Example 6

The *B. anthracis* $34F_2\Delta luxS$ has a Defect in AI-2 Activity and a Growth Defect Results AI-2 activity defect. The effect of the $34F_2\Delta luxS$ mutation on AI-2 synthesis was analyzed by testing the activity of filtered cell free medium (CFM) from cultures of $34F_2\Delta luxS$ bacteria in the *V. harveyi* bioassay (described above in Example 3).

*B. anthracis* strains $34F_2$ and $34F_2\Delta luxS$ were cultured in BHI broth overnight at 37° C. with aeration. Cell free medium (CFM) was prepared from these cultures, and tested for ability to stimulate *V. harveyi* strain BB170 luminescence (as described in Example 3, supra). In such assays, incubation of the reporter strain BB170 with sterile CFM alone (i.e., CFM never exposed to bacteria) served as the negative control. Incubation of the reporter strain BB170 with CFM from high-density cultures of *V. harveyi* strain BB170 served as the positive control.

Compared to the baseline level of luminescence seen upon treatment with sterile CFM alone, CFM from a high-density culture of $34F_2\Delta luxS$ had no additional AI-2 activity (FIG. 5). This result indicates that the *B. anthracis* luxS gene is required for luminescence-inducing AI-2 synthesis by *B. anthracis*.

Growth defect. *B. anthracis* strains $34F_2$ and $34F_2\Delta luxS$ were cultured in BHI broth overnight at 37° C. with aeration. These overnight cultures were used to inoculate 50 mL of fresh BHI medium, such that the new cultures had an optical density ($OD_{600}$) of 0.03 at the beginning of the culture period. These cultures were grown at 37° C. with aeration for 24 hrs and the optical density ($OD_{600}$) of the cultures measured at regular intervals. Optical densities at 600 nm ($OD_{600}$) of the bacterial cultures were measured by reading 1-ml aliquots, using a Beckman DU7400 spectrophotometer, where optical density is directly proportional to bacterial cell density in culture.

Figure 9:
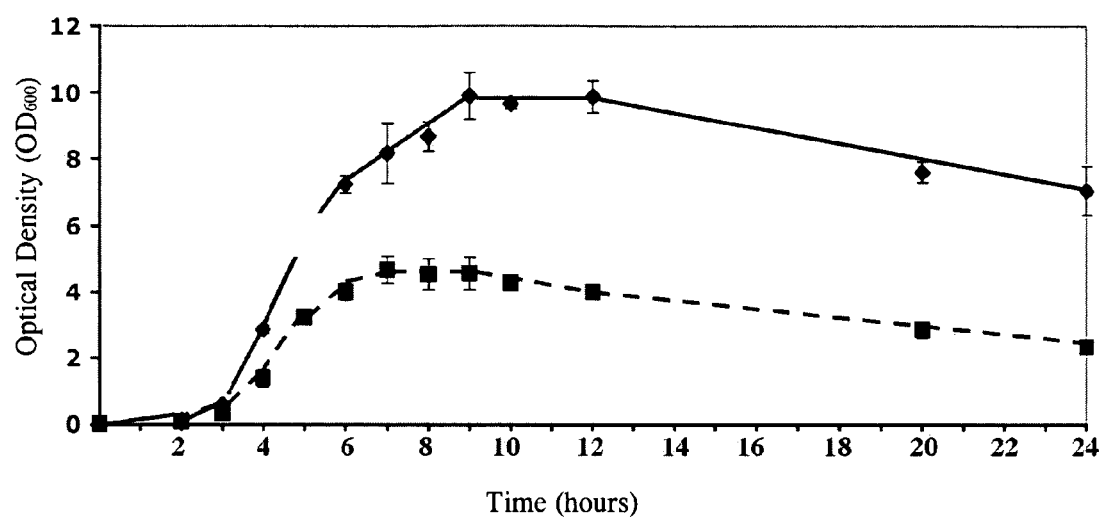
FIG. 9 depicts the growth rate of *B. anthracis* strains 34F$_2$ and 34F$_2$ΔluxS. Optical density (OD$_{600}$) of liquid cultures of *B. anthracis* 34F$_2$ΔluxS (■) and *B. anthracis* 34F$_2$ wild-type (♦) was measured at various time points. Bacterial growth curves are shown by plotting optical density (OD$_{600}$) measurements (Y-axis) versus time (X-axis).

When cultured in liquid medium, *B. anthracis* strain $34F_2\Delta luxS$ (■) exhibits noticeable growth defects compared to *B. anthracis* strain $34F_2$ (♦) (FIG. 9). Furthermore, the $34F_2\Delta luxS$ strain has a brief delay (approximately 30-60 minutes) in the transition between lag and early exponential phase, compared to the $34F_2$ wild-type strain. Subsequently, exponential growths for the wild-type and mutant strains are parallel, but the mutant enters into stationary phase at a much lower cell density. This result indicates that the *B. anthracis* luxS gene, and AI-2 synthesis, is required for robust *B. anthracis* growth.

Growth phase regulation of AI-2 synthesis in wildtype *B. anthracis*. To determine whether *B. anthracis* synthesis of AI-2 is growth phase-dependent, CFMs were collected from $34F_2$ cells at various time points in the growth cycle, and used in the *V. harveyi* bioluminescence assay (as described in Example 3, supra).

*B. anthracis* strain $34F_2$ was cultured overnight in BHI broth at 37° C. with aeration. These overnight cultures were used to inoculate 50 mL of fresh BHI medium, such that the new cultures had an optical density ($OD_{600}$) of 0.03 at the beginning of the culture period. These cultures were grown at 37° C. with aeration for 24 hrs and the optical density ($OD_{600}$) of the cultures measured at regular intervals, using a Beckman DU7400 spectrophotometer. From these same aliquots, CFMs were prepared for use in the *V. harveyi* bioluminescence assay. All assays were repeated in triplicate. In order to standardize CFM samples relative to $34F_2$ bacterial cell numbers, CFM samples were diluted in sterile medium such that the amount of CFM applied to *V. harveyi* reporter bacteria was equivalent to CFM derived from a $34F_2$ culture with $OD_{600}$=0.6. In such assays, incubation of the reporter strain BB170 with sterile CFM alone (i.e., CFM never exposed to bacteria) and with CFM from high-density cultures of $34F_2\Delta luxS$ served as negative controls. Incubation of the reporter strain BB170 with CFM from high-density cultures of *V. harveyi* strain BB170 served as the positive control.

Figure 10:
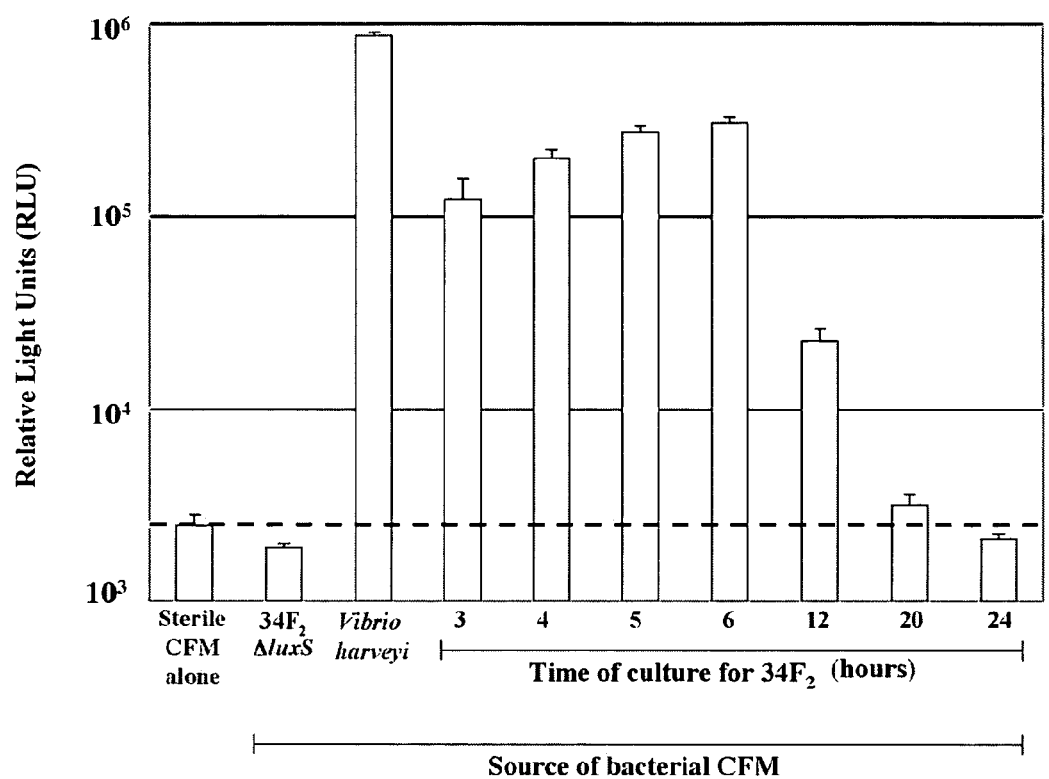
FIG. 10 depicts the induction of bioluminescence in *V. harveyi* reporter strain BB170 by cell free medium (CFM) collected at various time points from cultures of *B. anthracis* strain 34F$_2$. Sterile CFM alone and CFM from high-density culture of 34F$_2$ΔluxS were negative controls. The dashed line indicates the endogenous RLU observed for the "Sterile CFM alone" negative control. CFM from high-density culture of *V. harveyi* strain BB170 was the positive control.

This analysis of CFM collected from *B. anthracis* $34F_2$ (FIG. 10) showed that AI-2 is maximally synthesized during mid-exponential phase of growth (3 to 6 hours, see also FIG. 9), and diminishes during stationary phase (12 to 24 hours, see also FIG. 9).

Discussion

That CFM from *B. anthracis* strain $34F_2$ was able to stimulate luminescence in *V. harveyi* strain BB170 (FIGS. 5 and 9)

indicates that *B. anthracis* produces AI-2 or an AI-2-like molecule. Complementation of the *E. coli* strain DH5α® strain luxS gene mutation by expression of *B. anthracis* ORF BA5464, as revealed by the *V. harveyi* bioassay (FIG. 6) demonstrates that *B. anthracis* ORF BA5464 encodes a functional LuxS polypeptide that is involved in synthesis of AI-2 or an AI-2-like molecule. That *B. anthracis* synthesizes an AI-2 molecule suggests that *B. anthracis* conducts density-dependent gene expression.

Mutation of the *B. anthracis* luxS gene resulted in an inability of the *B. anthracis* mutant 34F$_2$ΔluxS to produce AI-2 or an AI-2-like molecule (FIGS. 5 and 9). In addition, compared to the wild-type 34F$_2$ strain, *B. anthracis* 34F$_2$ΔluxS showed a delay in the transition from lag to exponential growth phase, and entered stationary phase early (FIG. 9). Overall, the 34F$_2$ΔluxS culture grew more slowly and produced fewer cells compared to wild-type *B. anthracis*. This result establishes that synthesis of AI-2 or an AI-2-like molecule mediated by the luxS gene plays an important role in the regulation of *B. anthracis* growth.

Example 7

Figure 11:
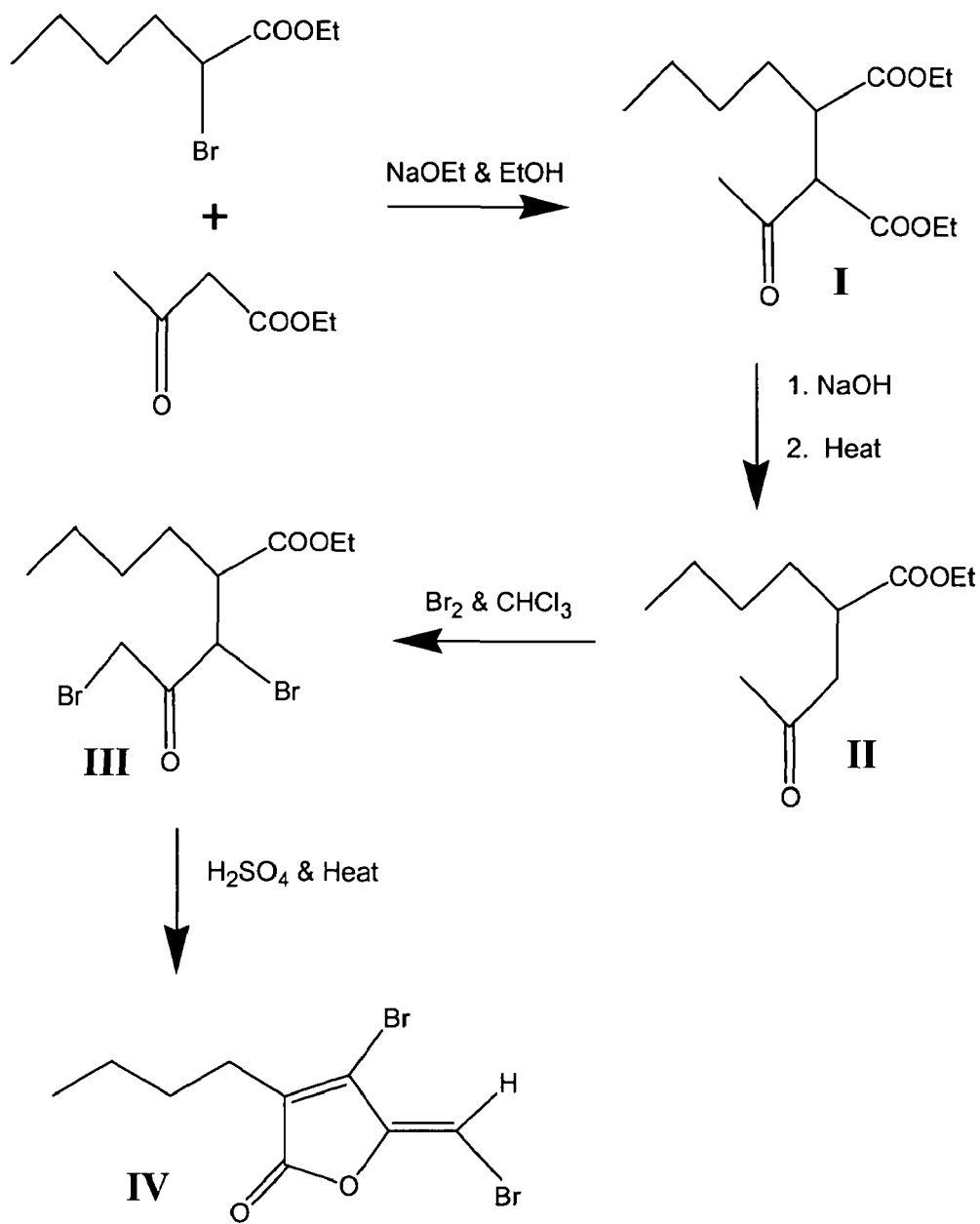
FIG. 11 depicts the chemical synthesis of (5Z)-4-bromo-5-(bromomethylene)-3-butyl-2(5H)-furanone.

Synthesis of (5Z)-4-bromo-5-(bromomethylene)-3-butyl-2(5H)-furanone (5Z)-4-bromo-5-(bromomethylene)-3-butyl-2(5H)-furanone was chemically synthesized as previously described (Beechan and Sims. Tetrahedron Letters 1979; 19:1649-1652). The synthetic reaction was performed as follows (see FIG. 11). Ethyl-2-bromohexate was reacted with ethyl acetoacetate in NaOEt and ethanol by heating under reflux until the mixture was of neutral pH to yield intermediate reaction product I. Intermediate reaction product I was hydrolyzed with NaOH at room temperature, and then refluxed in benzene for 30 minutes to yield intermediate reaction product II. Intermediate reaction product II was brominated in CHCl$_3$ to form intermediate reaction product III. Intermediate reaction product III was then treated with 100% H$_2$SO$_4$ at 100° C. for 20 min to produce crude (5Z)-4-bromo-5-(bromomethylene)-3-butyl-2(5H)-furanone, product IV.

The crude (5Z)-4-bromo-5-(bromomethylene)-3-butyl-2(5H)-furanone was then purified by column chromatography with hexane and ethyl acetate at a ratio of 100:1 (2.5×60 column, Spectra Chromatography, Houston, Tex.). The structure of the purified furanone was verified by nuclear magnetic resonance ($^1$H-NMR) (Druker DRX-400 MHz, Billerica, Mass.: 6.24 single peak, vinylidene; 2.39 triple peaks, coupling constant J7.2 Hz, allylic methylene; 0.93 triple peaks, coupling constant J 7.2 Hz, terminal methyl); by mass spectroscopy (Series II 5890, Hewlet Packard, San Fernando, Calif.: molecular ion peaks M$^+$ 308, 310, 312); and infrared spectroscopy (Nicolet-Magna-IR 560, Madison, Wis.: reciprocal absorbing wavelength 2958, 1793, 1610, 1276, 1108, 1030 cm$^{-1}$). Purified (5Z)-4-bromo-5-(bromomethylene)-3-butyl-2(5H)-furanone was dissolved in 95% EtOH.

Example 8

(5Z)-4-bromo-5-(bromomethylene)-3-butyl-2(5H)-furanone Inhibits *B. anthracis* Growth Furanone-1 inhibits *B. anthracis* growth. *B. anthracis* strain 34F$_2$ was cultured overnight in BHI broth at 37° C. with aeration. These overnight cultures were used to inoculate 50 mL of fresh BHI medium, such that the new cultures had an optical density (OD$_{600}$) of 0.03 at the beginning of the culture period. Prior to inoculation, the fresh BHI medium was supplemented with various concentrations of (5Z)-4-bromo-5-(bromomethylene)-3-butyl-2(5H)-furanone ("furanone 1") dissolved in 95% ethanol such that the final concentration of furanone 1 in the media was from 0-40 μg/ml (final ethanol concentration=0.12%). Cells cultured with 0 μg/ml furanone 1 served as the negative control. These cultures were grown at 37° C. with aeration for 24 hrs and the optical density (OD$_{600}$) of the cultures measured at regular intervals. Optical densities at 600 nm (OD$_{600}$) of the cultures were measured by reading 1-ml aliquots, using a Beckman DU7400 spectrophotometer.

Figure 12:
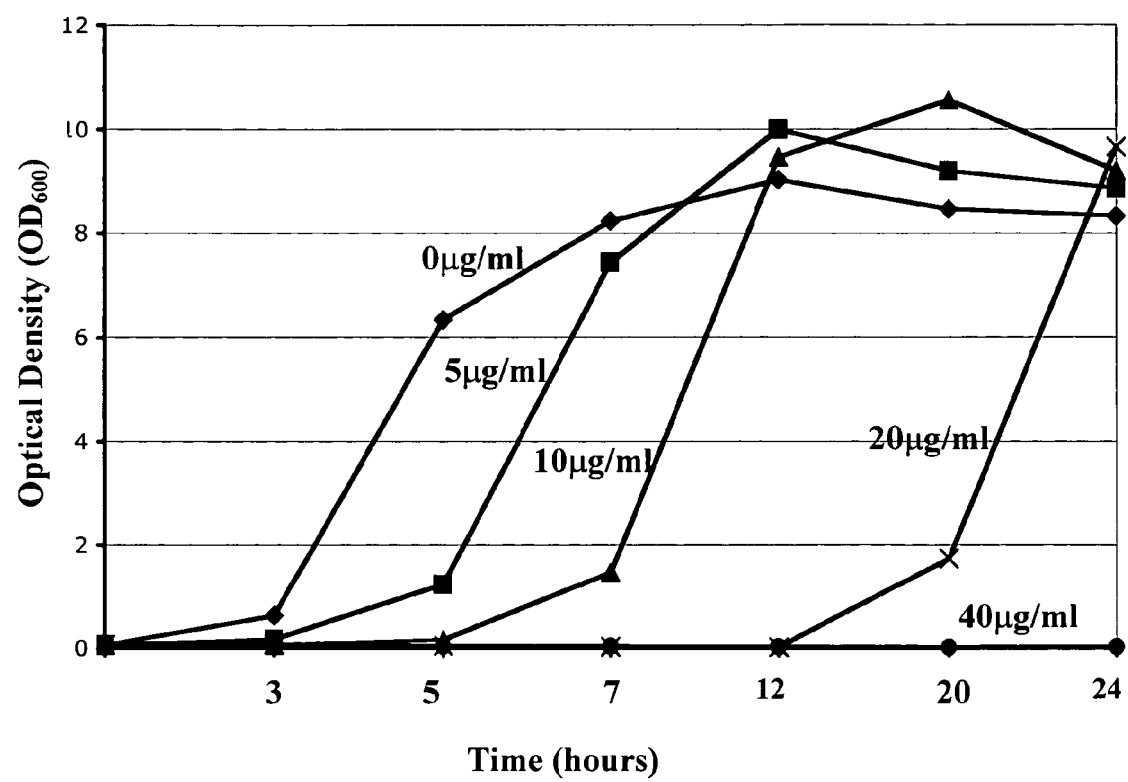
FIG. 12 depicts the effect of furanone on *B. anthracis* growth. *B. anthracis* strain 34F$_2$ was incubated with 0 μg/ml (♦); 5 μg/ml (■); 10 μg/ml (▲); 20 μg/ml (X); or 40 μg/ml (●) furanone. Bacterial growth curves are shown by plotting optical density (OD$_{600}$) measurements (Y-axis) versus time (X-axis).

FIG. 12 depicts the growth curves of *B. anthracis* cells incubated with 0 μg/ml (♦); 5 μg/ml (■); 10 μg/ml (▲); 20 μg/ml (X); or 40 μg/ml (●) furanone 1. With increasing concentration of the furanone 1, bacterial growth was increasingly retarded. Bacterial growth was completely inhibited for a 24-hour period by 40 μg/ml furanone 1.

Exposure to furanone does not select for furanone resistant bacteria. *B. anthracis* strain 34F$_2$ was cultured overnight at 37° C. with aeration in liquid BHI medium containing either 0 μg/ml or 20 μg/ml (5Z)-4-bromo-5-(bromomethylene)-3-butyl-2(5H)-furanone ("furanone 1") (final ethanol concentration=0.12%). This overnight culture period represents the pre-incubation period.

The overnight pre-incubation cultures were used to inoculate 50 mL of fresh BHI medium, such that the new cultures had an optical density (OD$_{600}$) of 0.03 at the beginning of the culture period. The fresh BHI medium contained either 0 μg/ml or 20 μg/ml furanone 1 (final ethanol concentration=0.12%). These cultures were grown at 37° C. with aeration for 24 hrs. This culture period represents the incubation period. The optical density (OD$_{600}$) of the incubation period cultures was measured at regular intervals. Optical densities at 600 nm (OD$_{600}$) of the cultures were measured by reading 1-ml aliquots, using a Beckman DU®$^-$7400 spectrophotometer.

Figure 13:
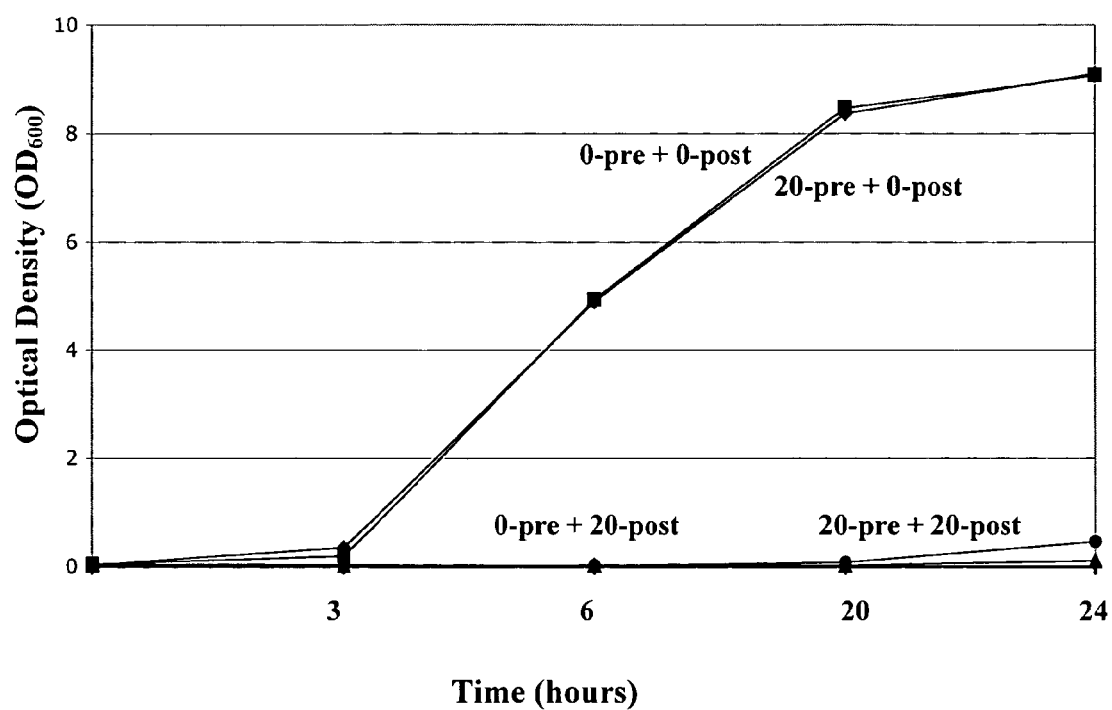
FIG. 13 depicts the effect of furanone pre-incubation on *B. anthracis* growth during the incubation period. "O-pre"=cells were pre-incubated without furanone. "20-pre"=cells were pre-incubated with 20 μg/ml of furanone. "0-post"=cells were incubated without furanone. "20-post"=cells were incubated with 20 μg/ml of furanone. Cell incubation conditions were "0-pre+0-post" (■); "0-pre+20-post" (♦); "20-pre+0-post" (▲); and "20-pre+20-post" (●). Bacterial growth curves are shown by plotting optical density (OD$_{600}$) measurements (Y-axis) versus time (X-axis).

The pre-incubation status (0 μg/ml or 20 μg/ml furanone 1) of the cells had no effect on bacterial growth during the incubation period (FIG. 13). As shown previously (FIG. 12), incubation with 20 μg/ml of furanone 1 dramatically inhibited *B. anthracis* growth (FIG. 13). These results indicate that pre-treatment of *B. anthracis* bacteria with 20 μg/ml furanone 1 does not select for furanone 1-resistant organisms.

A luxS gene mutation sensitizes *B. anthracis* to growth inhibition by furanone 1. *B. anthracis* strains 34F$_2$ and 34F$_2$ΔluxS were cultured overnight at 37° C. with aeration in liquid BHI medium. These overnight cultures were used to inoculate 50 mL of fresh BHI medium, such that the new cultures had an optical density (OD$_{600}$) of 0.03 at the beginning of the culture period. The fresh BHI medium contained either 0 μg/ml or 20 μg/ml furanone 1 (final ethanol concentration=0.12%). Cells cultured with 0 μg/ml furanone 1 served as the negative controls. These cultures were grown at 37° C. with aeration for 30 hrs and the optical density (OD$_{600}$) of the cultures measured at regular intervals. Optical densities at 600 nm (OD$_{600}$) of the cultures were measured by reading 1-ml aliquots, using a Beckman DU®$^-$7400 spectrophotometer.

Figure 14:
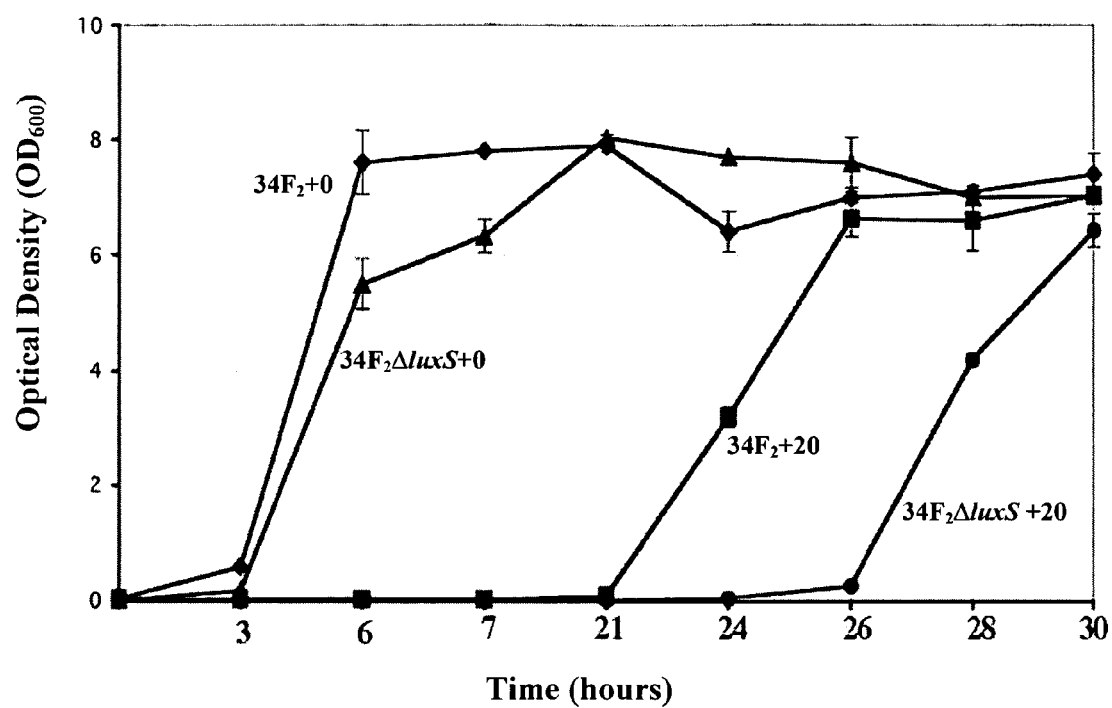
FIG. 14 depicts the effect of furanone treatment on growth of 34F$_2$ wild-type and 34F$_2$ΔluxS mutant *B. anthracis* strains. "34F$_2$+O"=34F$_2$ cultured with 0 μg/ml furanone (♦). "34F$_2$+20"=34F$_2$ cultured with 20 μg/ml furanone (■). "34F$_2$ΔluxS+O"=34F$_2$ΔluxS cultured with 0 μg/ml furanone (▲). "34F$_2$ΔluxS+20"=34F$_2$ΔluxS cultured with 20 μg/ml furanone (●). Bacterial growth curves are shown by plotting optical density (OD$_{600}$) measurements (Y-axis) versus time (X-axis).

As expected, the negative control 34F$_2$ΔluxS culture (0 μg/ml furanone 1) showed retarded growth relative to the negative control 34F$_2$ culture (0 μg/ml furanone 1) (FIG. 14). As shown previously (FIGS. 12 and 13), culture with 20 μg/ml furanone 1 dramatically inhibited growth of the wild-type 34F$_2$ strain (FIG. 14). Culture with 20 μg/ml furanone 1 also dramatically inhibited growth of the 34F$_2$ΔluxS strain. Notably, the growth inhibitory effect of furanone 1 was prolonged for the 34F$_2$ΔluxS strain relative to the wild-type 34F$_2$ strain, indicating that a luxS gene mutation sensitizes *B. anthracis* to growth inhibition by furanone 1.

Comparison of *B. anthracis* growth inhibition by different furanone analogs *B. anthracis* strain 34F$_2$ was cultured overnight as above. These overnight cultures were used to inoculate 50 mL of fresh BHI medium, such that the new cultures had an optical density (OD$_{600}$) of approximately 0.03 to 0.05 at the beginning of the culture period. Prior to inoculation, the fresh BHI medium was supplemented with (5Z)-4-bromo-5-(bromomethylene)-3-butyl-2(5H)-furanone ("furanone 1") dissolved in 95% ethanol, 3-butyl-5-(dibromomethylene)-2-(5H)-furanone ("furanone 2"), or 4-bromo-5-(bromomethylene)-2(5H)-furanone ("furanone 4") dissolved in methanol such that the final concentration of furanone in the media was 10 µg/ml (final ethanol concentration=0.0637%). Cells cultured alone or in the presence of 0.0637% ethanol or 0.05% methanol served as the negative control. These cultures were grown at 37° C. with aeration for 25 hrs and the optical density (OD$_{600}$) of the cultures measured at regular intervals. Optical densities at 600 nm (OD$_{600}$) of the cultures were measured by reading 1-ml aliquots, using a Beckman DU7400 spectrophotometer.

Figure 16:
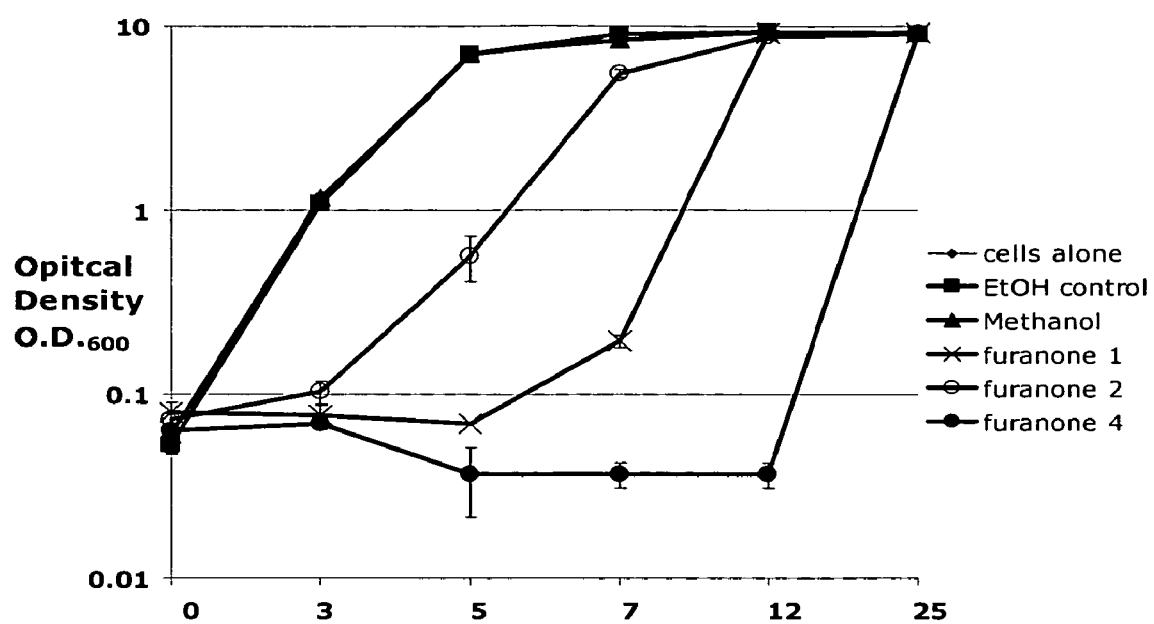
FIG. 16 depicts the effect of the addition of different analogs of furanone to *B. anthracis* growth. Growth curves corresponding to cells grown in media alone "cells alone" (♦) or with the addition of ethanol, "EtOH (■); "methanol" (▲); and "furanone 1" (X), furanone 2 (o), or furanone 4 (●). Bacterial growth curves are shown by plotting optical density (OD$_{600}$) measurements (Y-axis) versus time (X-axis).

FIG. 16 depicts the growth curves of *B. anthracis* cells incubated alone (♦), with ethanol (■); methanol (▲); or with 10 µg/ml of furanone 1 (X); furanone 2 (o) or furanone 4 (●). Ethanol or methanol alone had no deleterious effect on *B. anthracis* growth, as the growth curve matched that of the cells alone. All three furanones tested exhibited growth inhibition of *B. anthracis*. Furanone 4 displayed the most potent inhibitory effect, and furanone 2 the least. The differences between the inhibitory effects are likely attributable to the structural variations between the three furanone analogs tested.

Furanone 1 inhibits growth of *B. anthracis* log phase cells *B. anthracis* strain 34F$_2$ was cultured overnight as described above. These overnight cultures were used to inoculate 50 mL of fresh, sterile BHI medium, such that the new cultures had an optical density (OD$_{600}$) of approximately 0.03 at the beginning of the culture period. At four hours, when the cells were at log phase, *B. anthracis* cells were treated with various concentrations of furanone 1 dissolved as above. Cells cultured with 0 µg/ml furanone 1 served as the negative control. These cultures were grown at 37° C. with aeration for 5 hrs and the optical density (OD$_{600}$) of the cultures measured at regular intervals. Optical densities at 600 nm (OD$_{600}$) of the cultures were measured by reading 1-ml aliquots as above.

Figure 17:
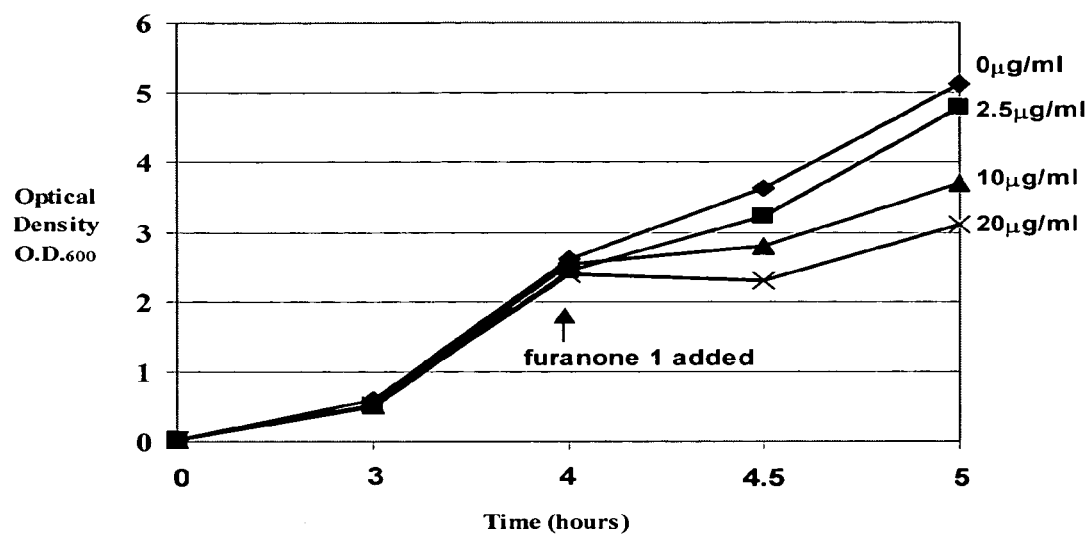
FIG. 17 depicts the effect on *B. anthracis* growth of different concentrations of furanone 1 added to cells during mid-log phase. Growth curves corresponding to additions of furanone 1 added are: "0 μg/ml" (♦); "2.5 μg/ml" (■); "10 μg/ml" (▲); and "20 μg/ml" (X). Bacterial growth curves are shown by plotting optical density (OD$_{600}$) measurements (Y-axis) versus time (X-axis).

FIG. 17 depicts the growth curves of *B. anthracis* cells incubated with 0 µg/ml (♦); 2.5 µg/ml (■); 10 µg/ml (▲); or 20 µg/ml (X) furanone 1. With increasing concentration of the furanone, bacterial growth was increasingly retarded. Thus, both treatment of *B. anthracis* cell at lag and log phases of growth with furanone 1.

Example 9

Expression and Purification of an Isolated LuxS Polypeptide

An expression construct for expression of a GST tagged *B. anthracis* LuxS polypeptide is made as follows: Plasmid pMJ501 (see Example 4) is digested with EcoRI to release the luxS sequences. This luxS fragment is then ligated to EcoRI digested pGEX-6P-3 (Amersham-Pharmcia) to generate pGST/LUXS. This choice of restriction enzyme maintains the translational frame across the GST tag and LuxS polypeptide encoding sequences. The proper orientation of the luxS fragment within the vector is confirmed by successful PCR using primer BAluxSF1 (SEQ ID NO: 21) or BAluxSR2 (SEQ ID NO: 22) and a pGEX-6P-3 vector primer.

Then, pGST/LUXS is transfected into *E. coli* XL1Blue host cells. Using a GST Purification Module (Amersham-Pharmacia), according to the manufacturer's instructions, expression of the GST-LuxS fusion polypeptide in a culture of *E. coli* host cells is induced with Isopropyl βD-thiogalactoside (IPTG) and the expressed GST-LuxS fusion polypeptide is purified. The GST tag of the purified GST-LuxS fusion polypeptide is removed by cleavage of the polypeptide with PreScission™ Protease (Amersham-Pharmacia) (dependent on pGEX vector used) according to the manufacture's instructions.

Example 10

Furanone-1 Treatment of *B. anthracis* Strain RBAF140 Inhibits Cell Growth and pag-lacZ Synthesis Materials and Methods

*B. anthracis* strain "RBAF140" is a strain containing pag-lacZ, the regulatory region for the pagA protective antigen gene fused to the gene coding for LacZ, inserted as a single copy at the corresponding pagA gene locus on pXO1 (Sirard, Mock, and Fouet. J. Bacteriol. 1994; 176:5188-92). In the presence of bicarbonate, transcription of the pag-lacZ reporter construct can be used to assess the pagA transcriptional activity. PA is key component of the *B. anthracis* toxin system: if PA protein is not produced, the toxins cannot get into cells.

R-medium is a minimal medium that is widely used to express the toxins of *B. anthracis* (Ristroph and Ivins. Infection and Immunity. 1983; 39:483-86)

Furanone 1 is described in Example 7, supra. The final concentrations in the flask are 40 µg/ml, 20 µg/ml, 10 µg/ml, or 2.5 µg/ml.

β-galactosidase assay for pag-lacZ expression: 1 ml aliquots were collected from RBAF140 cultures, pelleted, and pellets were snap frozen in an ethanol and dry ice bath. Cell pellets were resuspended in 500 µl of enriched Z-buffer (Z-buffer+freshly added β-mercaptoethanol at a volume of 2.7 µl per 1-liter of Z-buffer); 10 µl of toluene was added; the sample was vortexed for 1 min and incubated on ice for at least 1 hour. Meanwhile, 800 µl of fresh enriched Z-buffer was aliquoted into small tubes. 200 µl of the vortexed cell suspension was added to the fresh enriched Z-buffer and incubated for 15 minutes. 200-µl of ONPG (2-nitrophenyl-beta-D-galactopyranoside, 4 mg/ml in H$_2$O) was added to each sample and vortexed. When the sample turned yellow, the reaction was stopped with 1M Na$_2$CO$_3$. The start time (the time of ONPG addition), and the stop time (the time the reaction turned yellow) were recorded. Measurements at OD$_{420}$ (β-galactosidase absorbance) and OD$_{550}$ were taken. Finally, Miller Units (MU) were calculated to compare the β-galactosidase activities in each treatment condition: MU=1000×{[(OD$_{420}$−(1.75*OD$_{550}$)]/[(time in minutes)* (volume in ml)*(OD$_{600}$)]}

Z-buffer (500 ml): 28.85 ml 1M NaHPO$_4$; 21.15 ml 1M NaH$_2$PO$_4$; 5 ml 1M-KCl; 0.5 ml 1M MgSO4; water to 500 ml.

*B. anthracis* strain RBAF140 cells were grown overnight on TSA blood agar plates at 37° C. in 5% CO$_2$. Overnight cultures were diluted in fresh, sterile R-medium containing sodium bicarbonate, and cell densities were adjusted to an OD$_{600}$≈0.05. A set of control cells was grown in BHI media, which does not contain sodium bicarbonate. Cultures were grown at 37° C. with $CO_2$. Furanone 1 was added to log phase cells 3-hrs post-inoculation at concentrations of 40 μg/ml. Control *B. anthracis* cells were grown alone and in the presence of 0.25% EtOH to control for furanone 1 diluent. Cell densities were monitored by measuring $OD_{600}$, and 1-ml aliquots of cells from hours 0, 2, 3, 4, 5, 6, and 7 were frozen for β-gal analysis. Cells collected were thawed on ice and resuspended in buffer for analysis of β-gal activity. β-gal activity was measured in Miller Units.

Results and Discussion

To determine if furanone treatment of *B. anthracis* can inhibit toxin production, strain RBAF140 was grown in R-medium and treated with 40 μg/ml of furanone 1 (fur-1). pagA (protective antigen gene) is one of the three genes encoding the protein components of anthrax toxin. RBAF 140 is a *B. anthracis* strain that contains pag-lacZ: the promoter for the pagA gene linked to lacZ; a β-galactosidase assay performed on RBAF 140 (pag-lacZ) cells can demonstrate the efficacy of a potential inhibitor of pagA gene transcription and anthrax toxin production.

Figure 18A:
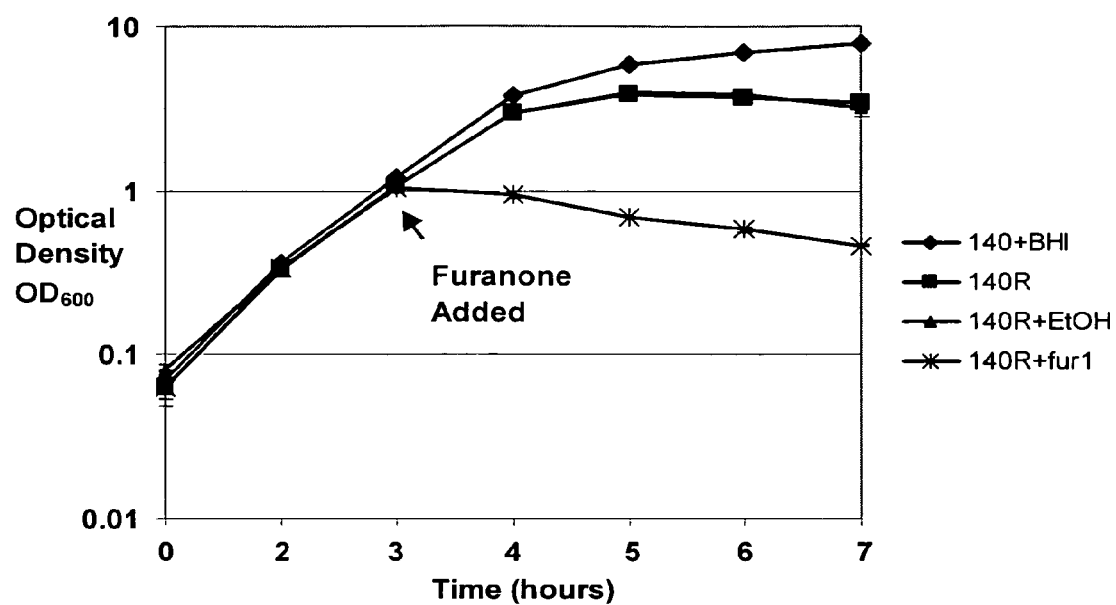
FIG. 18 depicts the effects on cell growth and pag-lacZ expression of adding furanone 1 to *B. anthracis* strain RBAF140 cells in log phase grown in R medium. A. Depicts the growth of *B. anthracis* strain RBAF140 grown in BHI medium alone, "140+BHI" (♦), or R medium alone "140R" (■); containing ethanol, "140R+EtOH" (▲); or containing furanone 1, "140R+fur1" (*). B. Depicts the expression of the reporter gene pag-lacZ in *B. anthracis* strain RBAF140 grown in BHI medium alone, "140+BHI" (♦), or R medium alone "140R" (■); containing ethanol, "140R+EtOH" (▲); or containing furanone 1, "140R+fur1" (●).
Figure 18B:
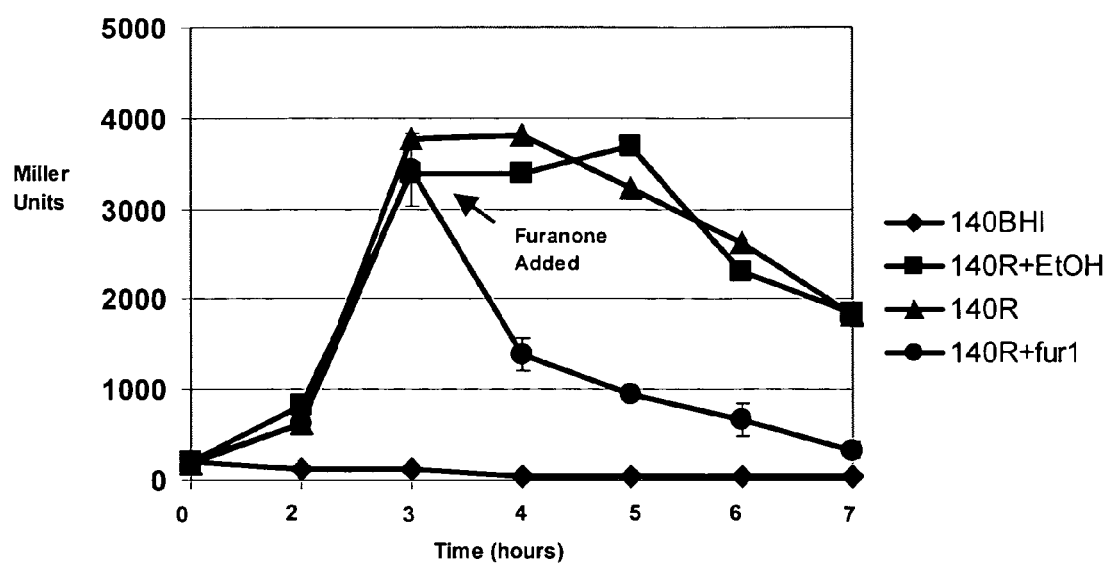

As demonstrated in FIG. 18A, the addition of furanone 1 had a growth inhibitory effect on RBAF 140 (pag-lacZ) cells grown in R medium with sodium bicarbonate: "140R+fur1" (*) vs. the controls grown in BHI medium alone, "140+BHI" (♦), or R medium alone "140R" (■); containing ethanol, "140R+EtOH". pag-lacZ expression was activated in the presence of sodium bicarbonate in the growth media, as demonstrated in FIG. 18B. *B. anthracis* strain RBAF140 grown in BHI lacking sodium bicarbonate had no noticeable or significant expression of pag-lacZ "140+BHI" (♦). Cells grown in R-medium with sodium bicarbonate had a significant increase in measurable β-gal expression that was sustained till five hours post inoculation, "140R" (■). Cells grown in the presence of the diluent, ethanol (EtOH), had no noticeable effect on RBAF140 pag-lacZ expression, "140R+EtOH" (▲). Cells exposed to 40 μg/ml of furanone 1 "140R+fur1" (●) had a significant inhibition of growth, compared to RBAF140 not exposed, and furanone 1 treatment also significantly reduced the expression of pag-lacZ. These data demonstrate that furanone 1 treatment of *B. anthracis* strain RBAF140 can inhibit bacteria growth and suppress pag-lacZ expression. These results suggest that furanone analog treatment of *B. anthracis* may potentially inhibit the expression of *B. anthracis* protective antigen expression in vivo.

Example 11

Effect of Furanone 1 on *B. anthracis* Gene Expression in Mid Log Phase

Materials and Methods

*B. anthracis* 34F$_2$ cells were grown overnight in Brain Heart Infusion (BHI) broth at 37° C. with aeration. Overnight cultures were diluted in fresh, sterile BHI, and cell densities were adjusted to an $OD_{600}$ of approximately 0.03. Cultures were grown at 37° C. with aeration. *B. anthracis* cells were treated 4-hrs post-inoculation with various concentrations of (5Z)-4-bromo-5-(bromomethylene)-3-butyl-2(5H)-furanone ("furanone 1") dissolved in 95% ethanol such that the final concentration of furanone in the media was 0, 2.5, 10, or 20 μg/ml (final ethanol concentration=0.12%). *B. anthracis* were also grown in the presence of EtOH to control for diluent. Cell densities were monitored by measuring $OD_{600}$.

Cells were collected 15- and 30-minutes post-exposure to furanone 1. RNA was extracted, converted into cDNA, and labeled according to TIGR (The Institute for Genomic Research, Rockville, Md.) protocols for the preparation of labeled cDNA for microarray assays Briefly, cells were treated with RNA protect (Qiagen, Valencia, Calif.) and frozen to −70° C. RNA was extracted from samples using the Ambion bacterial RiboPure® kit according to Manufacturer's standard protocols (Ambion, Austin, Tex.). 2-μg of RNA was converted to cDNA and coupled to the fluorescent dyes cy3 and cyc-5. Labeled cDNA was hybridized to array slides containing the full genome of *B. anthracis*. Slides were scanned and spots analyzed by utilizing TIGR Spotfinder software (The Institute for Genomic Research, Rockville, Md.). The array data was normalized for global intensity with TIGR MIDA (Microarray Data Analysis system) software. Genes were identified utilizing the TIGR TMEV (MultiExperiment Viewer) software. Genes that were considered significantly down- or up-regulated after furanone treatment had a $\log_2$ ratio $\geq 1.5$ after normalization.

Results and Discussion

The genes identified from the microarray experiments to identify genes up- and down-regulated by furanone 1 treatment of *B. anthracis* are summarized in the table in FIG. 19. The genes considered significantly up- or down-regulated by furanone 1 treatment of *B. anthracis* had a $\log_2$ ratio of greater than or equal to 1.5, and were either down or upregulated at 15 and 30 minutes post-stimulation with all concentrations of furanone 1 indicated.

Example 12

Effect of *B. anthracis* Furanone Treatment on PA Protein Expression (Prophetic)

To determine whether furanone 1 can inhibit expression of the *B. anthracis* protective antigen (PA), *B. anthracis* cells will be grown in R-medium containing sodium bicarbonate as described in Example 9, supra. Furanone 1 will be added 3-4 hours post inoculation. Cells will be collected at 2, 3, 4 and 5-hours post inoculation for analysis. To control for diluent, cells will be treated with the diluent alone (EtOH). *B. anthracis* cells will also be grown in BHI as a negative control for pagA expression. Cells will be lysed in 6× protein loading dye and boiled to extract protein for Western blot analysis. An antibody specific to PA (polyclonal, laboratory of MJ Blaser) will be used at a dilution of 1:5000 or 1:10,000 to determine the expression of PA in the presence or absence of furanone 1. Commercial antibodies to protective antigen are also widely available. β-galactosidase studies of pag-lacZ expression in RBAF140 indicate that *B. anthracis* cells treated with furanone 1 may show a significant reduction in PA expression.

Example 13

Evaluation of the Protective Effects of Mutated *B. anthracis*

To evaluate the safety and efficacy of the mutated 34F$_2$ΔluxS *B. anthracis* cells of the invention, mice will first be injected with various amounts of strain 34F$_2$ Sterne (which lacks a capsule) or a wild-type, virulent strain such as the Ames strain, in order to determine a lethal doses. The lethal dose for humans is estimated to be in a range from about $10^8$-$10^9$ spores for strain 34F$_2$ and about 5000 spores of the wild-type strain, for mice, $10^5$-$10^6$ spores for strain 34F$_2$ and about 10-100 spores of the wild-type strain.

Plasmid retention of the vaccine of the present invention will be evaluated, e.g., by intramuscularly inoculating animals with about $10^9$ cells, sacrificing the animals at several time points post-inoculation, and evaluating the plasma retention in vivo by culturing muscle homogenates in agar.

Various amounts of LuxS-mutated *B. anthracis* of the present invention will be administered to naïve mice. For example, 5 groups of 10 mice will be administered $1\times10^3$; $1\times10^5$, $5\times10^5$, $1\times10^6$ and $1\times10^7$ cells (depending on the CFU from above) intramuscularly in PBS with or without an adjuvant, and 0.1% gelatin. Vehicle treated mice will be used as a control. Mice will then be challenged 4-6 weeks after vaccination with a virulent strain of *B. anthracis* in a dose range from 1 to 100 times.

Results of vaccination can be evaluated by determining serological presence of antibodies, to e.g., PA or another antigen to the mutated vaccine, in addition to monitoring for protection from the challenge with virulent *B. anthracis* infection monitoring for fever and death.

Results

It is anticipated that the mutated 34F$_2$ΔluxS strain will elicit an effective immune response in vaccinated mice compared with unvaccinated control mice (in which certain death is expected with sufficiently high challenge doses). Accordingly, the vaccinated mice will have reduced, non-fatal symptoms of infection, or a complete absence of any symptoms of *B. anthracis* infection.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all values are approximate, and are provided for description.

The invention claimed is:

1. An isolated *Bacillus anthracis* cell in which the luxS gene of said *B. anthracis* cell is mutated by removal of the nucleotide sequence set forth in SEQ ID NO: 1 from the genome of said *B. anthracis* cell.

2. The *B. anthracis* cell of claim 1, wherein the removed nucleotide sequence is replaced by a nucleotide sequence conferring antibiotic resistance.

3. The *B. anthracis* cell of claim 2, wherein the nucleotide sequence conferring antibiotic resistance is a *B. subtilis* aphA gene.

4. A formulation comprising a pharmaceutically acceptable carrier and an isolated *Bacillus anthracis* cell in which the luxS gene of said *B. anthracis* cell is mutated by removal of the nucleotide sequence set forth in SEQ ID NO: 1 from the genome of said *B. anthracis* cell, wherein the mutated *B. anthracis* cell does not produce a functional LuxS polypeptide and shows reduced growth when grown in a cell-free culture medium compared to the growth of its wild-type cell.

5. The formulation of claim 4, wherein the removed nucleotide sequence is replaced by a nucleotide sequence conferring antibiotic resistance.

6. The formulation of claim 5, wherein the nucleotide sequence conferring antibiotic resistance is a *B. subtilis* aphA gene.

7. The formulation of claim 4 comprising an adjuvant.

8. The formulation of claim 7, wherein the adjuvant is aluminum hydroxide.

9. A method of inhibiting the growth of a *Bacillus anthracis* cell in a cell-free culture medium comprising inhibiting the functional activity of LuxS polypeptide of said *B. anthracis* cell by mutating the luxS gene of said *B. anthracis* cell by removal of the nucleotide sequence set forth in SEQ ID NO: 1 from the genome of said *B. anthracis* cell.

10. The method of claim 9, wherein the removed nucleotide sequence is replaced by a nucleotide sequence conferring antibiotic resistance.

11. The method of claim 10, wherein the nucleotide sequence conferring antibiotic resistance is a *B. subtilis* aphA gene.

* * * * *